(12) United States Patent
Harrison et al.

(10) Patent No.: US 7,759,514 B2
(45) Date of Patent: Jul. 20, 2010

(54) MU OPIOID RECEPTOR LIGANDS: METHODS OF USE AND SYNTHESIS

(76) Inventors: Bryce A. Harrison, 124a Wert Ave., Hamilton, NJ (US) 08610; Tiffany Malinky Gierasch, 100 Conestoga Rd. #A303, Bryn Mawr, PA (US) 19010; Gregory L. Verdine, 52 Hyde Ave., Newton, MA (US) 02458; Zhangjie Shi, 5110 S. Kenwood Ave., Chicago, IL (US) 60615

( * ) Notice: Subject to any disclaimer, the term of this patent is extended or adjusted under 35 U.S.C. 154(b) by 266 days.

(21) Appl. No.: 11/807,927

(22) Filed: May 29, 2007

(65) Prior Publication Data
US 2009/0093534 A1    Apr. 9, 2009

Related U.S. Application Data

(63) Continuation of application No. 10/683,756, filed on Oct. 10, 2003, now Pat. No. 7,223,888.

(60) Provisional application No. 60/417,925, filed on Oct. 11, 2002, provisional application No. 60/443,428, filed on Jan. 29, 2003.

(51) Int. Cl.
*C07C 327/22* (2006.01)
*C07C 229/34* (2006.01)

(52) U.S. Cl. .................. 560/38; 558/252; 514/529; 514/646

(58) Field of Classification Search ............. None
See application file for complete search history.

(56) References Cited

FOREIGN PATENT DOCUMENTS

WO    WO 99/65932    * 12/1999

* cited by examiner

*Primary Examiner*—Daniel M Sullivan
*Assistant Examiner*—Yevegeny Valenrod
(74) *Attorney, Agent, or Firm*—Edwards Angell Palmer & Dodge LLP; Jeffrey D. Hsi; Weiying Yang

(57) ABSTRACT

Novel compounds and compositions including those compounds, as well as methods of using and making the compounds are herein described. The compounds are useful in therapeutic applications, including modulation of disease or disease symptoms in a subject (e.g., mammal, human, dog, cat, horse). The compounds are useful as modulators of the mu opioid receptor (MOR) through their binding affinity with that receptor.

31 Claims, 4 Drawing Sheets

MU OPIOID RECEPTOR LIGANDS: METHODS OF USE AND SYNTHESIS

CROSS-REFERENCE TO RELATED APPLICATIONS

This application is a continuation of U.S. patent application Ser. No. 10/683,756, filed Oct. 10, 2003, pending, which claims benefit of U.S. patent application Ser. No. 60/417,924, filed Oct. 11, 2002 and U.S. patent application Ser. No. 60/443,428, filed Jan. 29, 2003. The contents of each of these patent applications is hereby incorporated by reference.

BACKGROUND

In the quest to address unmet needs in treatment and prevention of various diseases in humans and other subjects, one avenue is the discovery of small organic molecules having potent biological activity. This process relies, in part, on the investigation of diverse chemical compounds, or libraries of compounds. In particular, the emphasis of investigation of stereochemical variation as it relates to biological activity, for instance agonism or antagonism of various receptor targets having implications in disease mechanisms, is ever increasing.

Stereodiverse nonpeptide ligands are one approach to the discovery of new therapeutic agents. Based on known peptide ligands to a particular target, the approach involves discovery of "peptide mimics" (or peptidomimetics), compounds that structurally mimic the peptide ligand in particular functions, but that are not peptides. As such, the nonpeptides can offer therapeutic advantages, such as improved selectivity to targets, improved bioavailability, lessened adverse side effects, ease of manufacture, etc.

SUMMARY

The invention relates to novel compounds and compositions including those compounds, as well as methods of using and making the compounds. The compounds are nonpeptide compounds that are useful in therapeutic applications, including modulation of disease or disease symptoms in a subject (e.g., mammal, human, dog, cat, horse). The compounds (including stereoisomers thereof) are created either singly or in a combinatorial fashion to give structurally, and stereochemically diverse libraries of compounds. The compounds are useful as modulators of the mu opioid receptor (MOR) through their binding affinity with that receptor.

In one aspect, the invention is a compound of the formula (I):

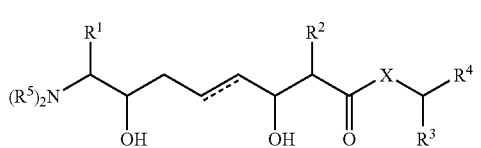

wherein, each $R^1$, $R^2$, and $R^3$ are independently alkyl substituted with aryl or heteroaryl, each of which is optionally substituted with 1-5 substituents selected from $OR^6$, CN, $NO_2$, $NHR^7$, $N(R^7)_2$, halo, $CONHR^7$, $CON(R^7)_2$, $CO_2R^8$, or $C_{1-6}$ alkyl;

X is N, O, or S;

$R^4$ is H, $CON(R^7)_2$, $CONHR^7$, $CH_2OH$, $CH(OH)CH=CH_2$, or $C(O)NHCHR^{10}CO_2H$;

each $R^5$ is independently H, alkyl, alkenyl, aryl, heteroaryl, acyl, $P^1$, or $C(O)CHR^{10}NH_2$;

each $R^6$ is independently H, alkyl, or $P^3$;

each $R^7$ is independently H, alkyl, acyl, or $P^2$;

each $R^8$ is independently H, alkyl, aralkyl, or heteroaralkyl;

each $R^{10}$ is independently an amino acid side chain;

each $P^1$ and is independently a nitrogen protecting group; and each $P^3$ is independently an oxygen protecting group;

or pharmaceutically acceptable salts thereof.

In certain aspects the invention is a compound of formula (I), wherein:

X is N or O;

$R^1$ is alkyl substituted with aryl, which is optionally substituted with 1-5 substituents selected from $OR^6$, CN, $NO_2$, $NHR^7$, $N(R^7)_2$, halo, $CONHR^7$, $CON(R^7)_2$, $CO_2R^8$, or $C_{1-6}$ alkyl;

$R^4$ is H, $CON(R^7)_2$, $C(O)NHCHR^{10}CO_2H$, or $CH_2OH$;

each $R^5$ is independently H, alkyl, acyl, $P^1$, or $C(O)CHR^{10}NH_2$;

each $R^6$ is independently H, alkyl, or $P^3$;

each $R^7$ is independently H, alkyl, acyl, or $P^2$;

each $R^8$ is independently H, alkyl, aralkyl, or heteroaralkyl;

each $R^{10}$ is independently an amino acid side chain;

each $P^1$ and $P^2$ is independently a nitrogen protecting group; and each $P^3$ is independently an oxygen protecting group.

In another aspect, the invention is a compound of formula (I), wherein:

X is N or O;

$R^1$ is alkyl substituted with aryl, which is optionally substituted with 1-5 substituents selected from $OR^6$, CN, $NO_2$, halo, or $C_{1-6}$ alkyl;

$R^4$ is H, $CONHR^7$, or $CH_2OH$;

each $R^5$ is independently H or alkyl;

each $R^6$ is independently H or alkyl;

$R^7$ is H, alkyl, or $P^2$; and $P^2$ is a nitrogen protecting group.

In another aspect, the invention is a compound of formula (I), wherein:

X is N or O;

$R^1$ is alkyl substituted with aryl, which is optionally substituted with 1-5 substituents selected from OH or $C_{1-6}$ alkyl; and $R^4$ is H, $CONH_2$, or $CH_2OH$.

In another aspect, the invention is a compound of formula (I), wherein:

X is N or O;

$R^1$ is $C_1$ alkyl substituted with phenyl, which is substituted at the 2- and 6-positions with Me and is substituted at the 4-position with OH; and $R^4$ is H, $CONH_2$, or $CH_2OH$.

In still another aspect, the invention is a compound having the formula (II):

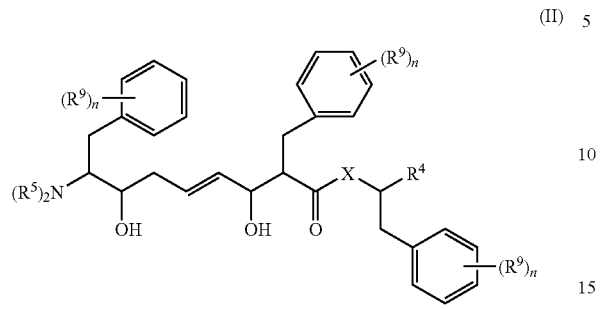

(II)

wherein,
X is N or O;
$R^4$ is H, $CON(R^7)_2$, $CONHR^7$, $CH_2OH$, or $C(O)NHCHR^{10}CO_2H$;
each $R^5$ is independently H, alkyl, acyl, $P^1$, or $C(O)CHR^{10}NH_2$;
each $R^6$ is independently H, alkyl, or $P^3$;
each $R^7$ is independently H, alkyl, acyl, or $P^2$;
each $R^8$ is independently H, alkyl, aralkyl, or heteroaralkyl;
each $R^9$ is independently $OR^6$, CN, $NO_2$, $NHR^7$, $N(R^7)_2$, halo, $CONHR^7$, $CON(R^7)_2$, $CO_2R^8$, or $C_{1-6}$ alkyl;
each $R^{10}$ is independently an amino acid side chain;
each n is independently 0, 1, 2, 3, 4, or 5;
each $P^1$ and $P^2$ is independently a nitrogen protecting group; and
each $P^3$ is independently an oxygen protecting group.

In another aspect, the invention is a compound of formula (II), wherein:
$R^4$ is H, $CON(R^7)_2$, $CONHR^7$, or $CH_2OH$;
each $R^5$ is independently H, alkyl, or acyl;
each $R^6$ is independently H or alkyl;
each $R^7$ is independently H or alkyl;
each $R^9$ is independently $OR^6$, CN, $NO_2$, halo, or $C_{1-6}$ alkyl;
each n is independently 0, 1, 2, or 3.

In another aspect, the invention is a compound of formula (II), wherein:
$P^1$ is a BOC or Fmoc;
$P^2$ is a solid support; and
$P^3$ is t-Bu, Bn, Me, or Ac.

In another aspect, the invention is a compound of formula (II), wherein:
$R^4$ is H, $CON(R^7)_2$, $CONHR^7$, or $CH_2OH$;
each $R^5$ is independently H, alkyl, acyl, or $P^1$;
each $R^6$ is independently H or $P^3$;
each $R^7$ is independently H or $P^2$;
each $R^9$ is independently $OR^6$ or $C_{1-6}$ alkyl;
each n is independently 0, 1, or 2;
$P^1$ is a BOC;
$P^2$ is a solid support; and
$P^3$ is t-Bu.

In another aspect, the invention is a compound of formula (II), wherein:
$R^4$ is H, $CONH_2$, or $CH_2OH$;
each $R^5$ is independently H, $P^1$, or $C(O)CHR^{10}NH_2$;
each $R^6$ is H or alkyl
each $R^9$ is $C_{1-6}$ alkyl or $OR^6$;
each $R^{10}$ is independently an amino acid side chain;
each n is independently 1, 2, or 3; and
$P^1$ is a nitrogen protecting group.

In yet another aspect, the invention is a compound of formula (III):

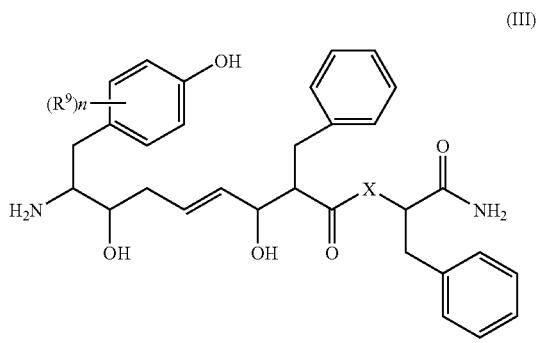

(III)

wherein,
X is O or N;
$R^9$ is $C_{1-6}$ alkyl; and
n is 2.

In still another aspect, the invention is a compound of formula (IV):

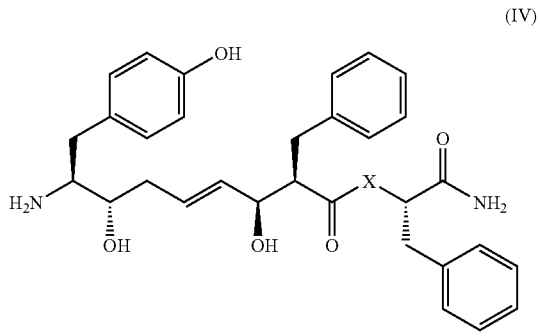

(IV)

wherein X is N or O.

In a further aspect, the invention is a compound of formula (V):

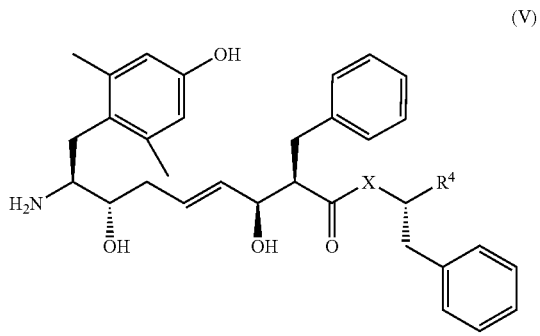

(V)

(S, S, S, R)

wherein
X is N or O; and
$R^4$ is $CONH_2$, H, or $CH_2OH$.

In another aspect, the invention is a compound having the formula (VI):

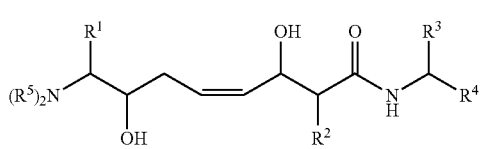

(VI)

wherein,
each $R^1$, $R^2$, and $R^3$ is independently alkyl substituted with aryl or heteroaryl, each of which is optionally substituted with 1-5 substituents selected from $OR^6$, CN, $NO_2$, $NHR^7$, $N(R^7)_2$, halo, $CONHR^7$, $CON(R^7)_2$, $CO_2R^8$, or $C_{1-6}$ alkyl;
$R^4$ is H, $CON(R^7)_2$, $CONHR^7$, $CH_2OH$, or $CH(OH)CH=CH_2$, or $C(O)NHCHR^{10}CO_2H$;
each $R^5$ is independently H, alkyl, alkene, aryl, heteroaryl, acyl, or $P^1$, or $C(O)CHR^{10}NH_2$;
each $R^6$ is independently H, alkyl, or $P^3$;
each $R^7$ is independently H, alkyl, acyl, or $P^2$;
each $R^8$ is independently H, alkyl, aralkyl, or heteroaralkyl;
each $R^{10}$ is independently an amino acid side chain;
each $P^1$ and $P^2$ is independently a nitrogen protecting group; and
each $P^3$ is independently an oxygen protecting group.

In another aspect, the invention is a compound of formula (VI), wherein:
each $R^1$, $R^2$, and $R^3$ is independently alkyl substituted with aryl, each of which is optionally substituted with 1-5 substituents selected from $OR^6$, CN, $NO_2$, halo, or $C_{1-6}$ alkyl;
$R^4$ is H, $CON(R^7)_2$, or $CONHR^7$, or $C(O)NHCHR^{10}CO_2H$;
each $R^5$ is independently H, alkyl, acyl, $P^1$, or $C(O)CHR^{10}NH_2$; and
each $R^{10}$ is independently an amino acid side chain.

In one aspect, the invention is a compound of the formula (VII):

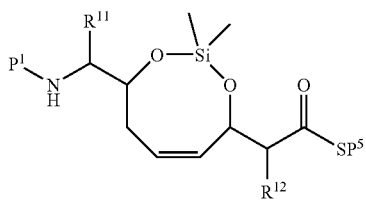

(VII)

wherein,
each $R^{11}$ and $R^{12}$ is alkyl substituted with aryl or heteroaryl, each of which is optionally substituted with 1-5 substituents selected from $OR^{16}$, CN, $NO_2$, $NHR^{17}$, $N(R^{17})_2$, halo, $CONHR^{17}$, $CON(R^{17})_2$, $CO_2R^{18}$, or $C_{1-6}$alkyl;
each $R^{16}$ is independently H, alkyl or $P^3$;
each $R^{17}$ is independently H, alkyl acyl, or $P^2$;
each $R^{18}$ is independently H, alkyl, aralkyl, or heteroaralkyl;
each $P^1$ and $P^2$ is independently a nitrogen protecting group;
each $P^3$ is independently an oxygen protecting group; and
$P^5$ is a sulfur protecting group, or pharmaceutically acceptable salts thereof.

In another aspect, the invention is a compound of formula (VII), wherein:
$R^{11}$ is alkyl substituted with aryl, which is optionally substituted with 1-5 substituents selected from $OR^{16}$ or $C_{1-6}$ alkyl; and
each $R^{16}$ is independently H, alkyl, or $P^3$.

In another aspect, the invention is a compound of formula (VII), wherein:
$R^{11}$ is alkyl substituted with aryl, which is optionally substituted with 1 $OR^{16}$;
$R^{16}$ is H or $P^3$;
$P^1$ is Boc or Fmoc; and
$P^3$ is t-Bu, Bn, Me, Ac, or TBS.

In another aspect, the invention is a compound of formula (VII), wherein:
$R^{11}$ is alkyl substituted with aryl, which is optionally substituted with 1 $OR^{16}$;
$R^{16}$ is H or $P^3$;
$P^1$ is Boc; and
$P^3$ is t-Bu.

In one aspect, the invention is a compound of formula (XXVI):

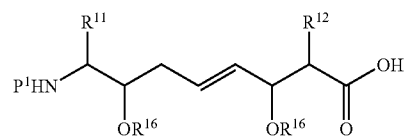

(XXVI)

wherein,
each of $R^{11}$ and $R^{12}$ is independently alkyl substituted with aryl or heteroaryl, each of which is optionally substituted with 1-5 substituents selected from $OR^{16}$, CN, $NO_2$, $NHR^{17}$, $N(R^{17})_2$, halo, $CONHR^{17}$, $CON(R^{17})_2$, $CO_2R^{18}$, or $C_{1-6}$alkyl;
each $R^{16}$ is independently H, alkyl, or $P^3$;
each $R^{17}$ is independently H, alkyl acyl, or $P^2$;
each $R^{18}$ is independently H, alkyl, aralkyl, or heteroaralkyl;
each $P^1$ and is independently a nitrogen protecting group; and
each $P^3$ is independently an oxygen protecting group;

or pharmaceutically acceptable salts thereof.

In another aspect, the invention is a compound of formula (XXVI), wherein:
each of $R^{11}$ and $R^{12}$ is independently alkyl substituted with aryl or heteroaryl, each of which is optionally substituted with 1-5 substituents selected from $OR^{16}$ or $C_{1-6}$ alkyl; and
each $R^{16}$ is independently H, or $P^3$.

In one aspect, the invention is a method of making a compound of the formula (VIII):

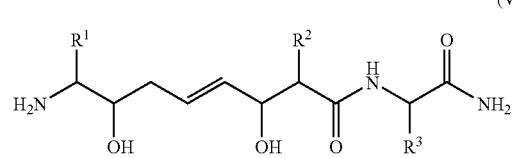

(VIII)

including reacting a compound of formula (IX)

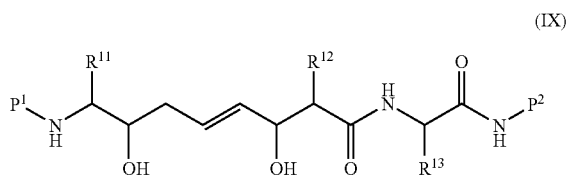

with a deprotecting agent to give a compound of formula (VIII);

wherein, each $R^1$, $R^2$, and $R^3$ are independently alkyl substituted with aryl or heteroaryl, each of which is optionally substituted with, 1-5 substituents selected from $OR^6$, CN, $NO_2$, $NHR^7$, $N(R^7)_2$, halo, $CONHR^7$, $CON(R^7)_2$, $CO_2R^8$, or $C_{1-6}$ alkyl;

each $R^6$ is independently H, alkyl, or $P^3$;

each $R^7$ is independently H, alkyl, acyl, or $P^4$;

each $R^8$ is independently H, alkyl, aralkyl, or heteroaralkyl;

each $R^{11}$, $R^{12}$, and $R^{13}$ is independently alkyl substituted with aryl or heteroaryl, which is optionally substituted with 1-5 substituents selected from $OR^{16}$, CN, $NO_2$, $NHR^{17}$, $N(R^{17})_2$, halo, $CONHR^{17}$, $CON(R^{17})_2$, $CO_2R^{18}$, or $C_{1-6}$ alkyl;

each $R^{16}$ is independently H, alkyl, or $P^3$;

each $R^{17}$ is independently H, alkyl, acyl, or $P^4$;

each $R^{18}$ is independently H, alkyl, aralkyl, or heteroaralkyl;

each $P^1$, $P^2$, and $P^4$ is independently a nitrogen protecting group; and each $P^3$ is independently an oxygen protecting group.

In certain aspects, $P^1$, $P^2$, and $P^3$ are each independently acid labile protecting groups and the deprotecting agent is an acid.

In other aspects, $P^1$ is Boc or Fmoc; $P^2$ is a solid support; and $P^3$ is t-Bu, Bn, Me, or Ac.

In one aspect, the invention is a method of making a compound of the formula (X):

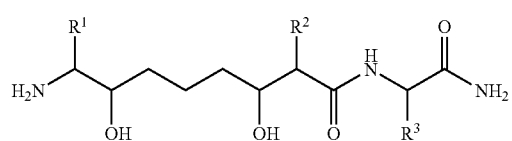

including reacting a compound of formula (IX)

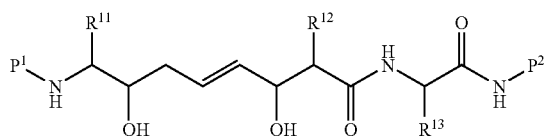

with a hydrogen transfer reagent, and reacting the resulting compound with at least one deprotecting agent under conditions sufficient to remove $P^1$ and $P^2$, to give a compound of formula (X);

wherein, each $R^1$, $R^2$, and $R^3$ is independently alkyl substituted with aryl or heteroaryl, each of which is optionally substituted with 1-5 substituents selected from $OR^6$, CN, $NO_2$, $NHR^7$, $N(R^7)_2$, halo, $CONHR^7$, $CON(R^7)_2$, $CO_2R^8$, or $C_{1-6}$alkyl;

each $R^6$ is independently H, alkyl or $P^3$;

each $R^7$ is independently H, alkyl, acyl, or $P^4$;

each $R^8$ is independently H, alkyl, aralkyl, or heteroaralkyl;

each $R^{11}$, $R^{12}$, and $R^{13}$ is independently alkyl substituted with aryl or heteroaryl, each of which is optionally substituted with 1-5 substituents selected from $OR^{16}$, CN, $NO_2$, $NHR^{17}$, $N(R^{17})_2$, halo, $CONHR^{17}$, $CON(R^{17})_2$, $CO_2R^{18}$, or $C_{1-6}$ alkyl;

each $R^{16}$ is independently H, alkyl, or $P^3$;

each $R^{17}$ is independently H, alkyl acyl, or $P^4$;

each $R^{18}$ is independently H, alkyl, aralkyl, or heteroaralkyl;

each $P^1$, $P^2$, and $P^4$ is independently a nitrogen protecting group; and each $P^3$ is independently an oxygen protecting group.

In some aspects, the deprotecting agent is an acid.

In other aspects, $P^1$ is Boc or Fmoc; $P^2$ is a solid support; and $P^3$ is t-Bu, Bn, Me, Ac, or TBS.

In one aspect, the invention is a method of making a compound of the formula (VIII):

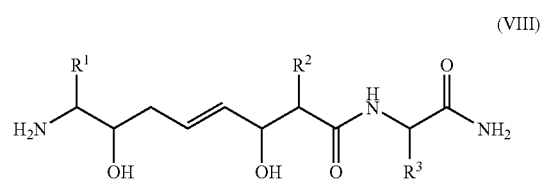

including coupling compounds of the formulas (XI) and (XII)

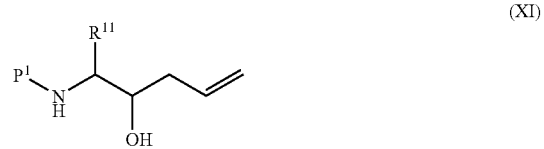

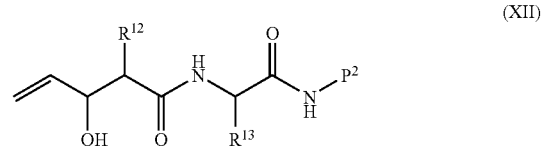

using a ruthenium catalyst, to give a compound of formula (IX); and

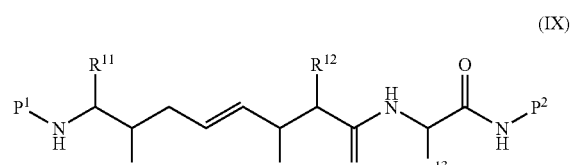

reacting the compound of formula (IX) with a deprotecting agent to give a compound of the formula (VIII);

wherein, each $R^1$, $R^2$, and $R^3$ is independently alkyl substituted with aryl or heteroaryl, each of which is optionally substituted with 1-5 substituents selected from $OR^6$, CN, $NO_2$, $NHR^7$, $N(R^7)_2$, halo, $CONHR^7$, $CON(R^7)_2$, $CO_2R^8$, or $C_{1-6}$ alkyl;

each $R^6$ is independently H, alkyl or $P^3$;

each $R^7$ is independently H, alkyl acyl, or $P^4$;

each $R^8$ is independently H, alkyl, aralkyl, or heteroaralkyl;

each $R^{11}$, $R^{12}$, and $R^{13}$ is independently alkyl substituted with aryl or heteroaryl, each of which is optionally substituted with 1-5 substituents selected from $OR^{16}$, CN, $NO_2$, $NHR^{17}$, $N(R^{17})_2$, halo, $CONHR^{17}$, $CON(R^{17})_2$, $CO_2R^{18}$, or $C_{1-6}$ alkyl;

each $R^{16}$ is independently H, alkyl, or $P^3$;

each $R^{17}$ is independently H, alkyl, acyl, or $P^4$;

each $R^{18}$ is independently H, alkyl, aralkyl, or heteroaralkyl;

each $P^1$, $P^2$, and $P^4$ is independently a nitrogen protecting group; and each $P^3$ is independently an oxygen protecting group.

In certain aspects, $P^1$, and $P^2$, are each independently acid labile protecting groups and the deprotecting agent is an acid.

In some aspects, $P^1$ is Boc or Fmoc; $P^2$ is a solid support; and $P^3$ is t-Bu, Bn, Me, Ac, or TBS.

In other aspects, the ruthenium catalyst is $Cl_2(PCy3)(IMesH_2)RuCHPh$, $Cl_2(PCy_3)_2RuCHPh$, $Cl_2(PCy_3)(IMes)RuCHPh$, or a compound of formula (XV)

(XV)

In still other aspects, the ruthenium catalyst is $Cl_2(PCy_3)(IMesH_2)RuCHPh$.

In one aspect, the invention is a method of making a compound of the formula (X):

(X)

including coupling compounds of the formulas (XI) and (XII)

(XI)

(XII)

using a ruthenium catalyst, to give a compound of formula (IX);

(IX)

treating the compound with a reagent that reductively transfers two hydrogen atoms from the reagent to an olefin; and reacting the resulting compound to with a deprotecting agent sufficient to remove $P^1$ and $P^2$, to give a compound of the formula (X);

wherein, each $R^1$, $R^2$, and $R^3$ is independently alkyl substituted with aryl or heteroaryl, each of which is optionally substituted with 1-5 substituents selected from $OR^6$, CN, $NO_2$, $NHR^7$, $N(R^7)_2$, halo, $CONHR^7$, $CON(R^7)_2$, $CO_2R^8$, or $C_{1-6}$ alkyl;

each $R^6$ is independently H, alkyl, or $P^3$;

each $R^7$ is independently H, alkyl, acyl, or $P^4$;

each $R^8$ is independently H, alkyl, aralkyl, or heteroaralkyl;

each $R^{11}$, $R^{12}$, and $R^{13}$ is independently alkyl substituted with aryl or heteroaryl, each of which is optionally substituted with 1-5 substituents selected from $OR^{16}$, CN, $NO_2$, $NHR^{17}$, $N(R^{17})_2$, halo, $CONHR^{17}$, $CON(R^{17})_2$, $CO_2R^{18}$, or $C_{1-6}$ alkyl;

each $R^{16}$ is independently H, alkyl, or $P^3$;

each $R^{17}$ is independently H, alkyl, acyl, or $P^4$;

each $R^{18}$ is independently H, alkyl, aralkyl, or heteroaralkyl;

each $P^1$, $P^2$, and $P^4$ is independently a nitrogen protecting group; and each $P^3$ is independently an oxygen protecting group.

In some aspects, the deprotecting agent is an acid.

In some aspects, $P^1$ is Boc or Fmoc; $P^2$ is a solid support; and $P^3$ is t-Bu, Bn, Me, Ac, or TBS.

In some aspects, the ruthenium catalyst is $Cl_2(PCy_3)(IMesH_2)RuCHPh$, $Cl_2(PCy_3)_2RuCHPh$, $Cl_2(PCy_3)(IMes)RuCHPh$, or a compound of formula (XV)

(XV)

In some aspects, the ruthenium catalyst is $Cl_2(PCy_3)$ $(IMesH_2)RuCHPh$.

In one aspect, the invention is a method of making a compound of the formula (XVI):

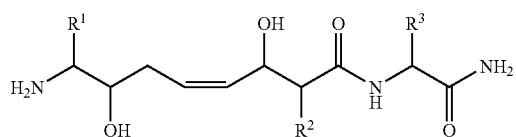
(XVI)

including reacting a compound of formula (VII)

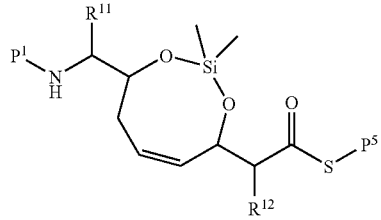
(VII)

with a deprotecting agent sufficient to remove protecting groups, if any;

treating the product with peroxide and base under conditions sufficient to hydrolyze the thioester; and coupling the resulting product with a solid phase peptide, giving a compound of the formula (XVI);

wherein, each $R^1$, $R^2$, and $R^3$ is independently alkyl substituted with aryl or heteroaryl, each of which is optionally substituted with 1-5 substituents selected from $OR^6$, CN, $NO_2$, $NHR^7$, $N(R^7)_2$, halo, $CONHR^7$, $CON(R^7)_2$, $CO_2R^8$, or $C_{1-6}$ alkyl;

each $R^6$ is independently H, alkyl, or $P^3$;

each $R^7$ is independently H, alkyl, acyl, or $P^4$;

each $R^8$ is independently H, alkyl, aralkyl, or heteroaralkyl;

each $R^{11}$ and $R^{12}$ is independently alkyl substituted with aryl or heteroaryl, each of which is optionally substituted with 1-5 substituents selected from $OR^{16}$, CN, $NO_2$, $NHR^{17}$, $N(R^{17})_2$, halo, $CONHR^{17}$, $CON(R^{17})_2$, $CO_2R^{18}$, or $C_{1-6}$ alkyl;

each $R^{16}$ is independently H, alkyl, or $P^3$;

each $R^{17}$ is independently H, alkyl, acyl, or $P^4$;

each $R^{18}$ is independently H, alkyl, aralkyl, or heteroaralkyl;

each $P^1$ and $P^4$ is independently a nitrogen protecting group; and each $P^3$ is independently an oxygen protecting group; and $P^5$ is a sulfur protecting group.

In certain aspects, the deprotecting agent is an acid and $P^1$ is an acid labile protecting group.

In some aspects, $P^1$ is Boc or Fmoc; $P^3$ is t-Bu, Bn, Me, Ac, or TBS; and $P^5$ is Bn.

In one aspect, the invention is a method of making a compound of the formula (XVI):

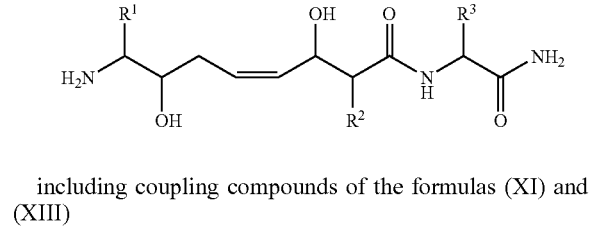
(XVI)

including coupling compounds of the formulas (XI) and (XIII)

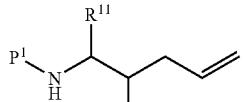
(XI)

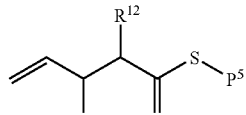
(XIII)

by first reacting the free alcohols with a silicon protecting group, and then treating the resulting compound with a ruthenium catalyst, giving a compound of the formula (VII);

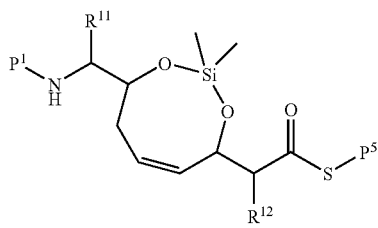
(VII)

reacting the compound of formula (VII) under pH conditions sufficient to remove acid labile protecting groups, if any;

treating the resulting product with peroxide and base under conditions sufficient to hydrolyze the thioester; and coupling the resulting product with a solid phase peptide, giving a compound of the formula (XVI);

wherein, each $R^1$, $R^2$, and $R^3$ is independently alkyl substituted with aryl or heteroaryl, each of which is optionally substituted with 1-5 substituents selected from $OR^6$, CN, $NO_2$, $NHR^7$, $N(R^7)_2$, halo, $CONHR^7$, $CON(R^7)_2$, $CO_2R^8$, or $C_{1-6}$ alkyl;

each $R^6$ is independently H, alkyl, or $P^3$;

each $R^7$ is independently H, alkyl, acyl, or $P^4$;

each $R^8$ is independently H, alkyl, aralkyl, or heteroaralkyl;

each $R^{11}$ and $R^{12}$ is independently alkyl substituted with aryl or heteroaryl, each of which is optionally substituted with 1-5 substituents selected from $OR^{16}$, CN, $NO_2$, $NHR^{17}$, $N(R^{17})_2$, halo, $CONHR^{17}$, $CON(R^{17})_2$ $CO_2R^{18}$, or $C_{1-6}$ alkyl;

each $R^{16}$ is independently H, alkyl, or $P^3$;

each $R^{17}$ is independently H, alkyl, acyl, or $P^4$;

each $R^{18}$ is independently H, alkyl, aralkyl, or heteroaralkyl;

each $P^1$ and $P^4$ is independently a nitrogen protecting group; and each $P^3$ is independently an oxygen protecting group; and $P^5$ is a sulfur protecting group.

In some aspects, $P^1$ is acid labile.

In some aspects, $P^1$ is Boc or Fmoc; and $P^3$ is t-Bu, Bn, Me, Ac, or TBS.

In some aspects, the ruthenium catalyst is $Cl_2(PCy_3)(IMesH_2)RuCHPh$, $Cl_2(PCy_3)_2RuCHPh$, $Cl_2(PCy_3)(IMes)RuCHPh$, or a compound of formula (XV)

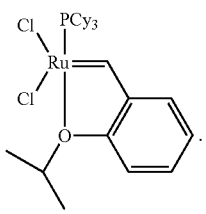

(XV)

In some aspects, the ruthenium catalyst is $Cl_2(PCy_3)(IMesH_2)RuCHPh$.

In one aspect, the invention is a method of making a compound of the formula (VI):

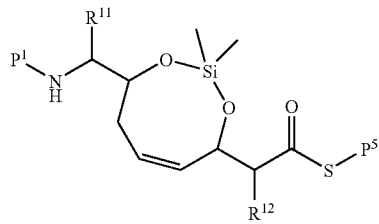

(VII)

including coupling compounds of the formulas (XI) and (XIII)

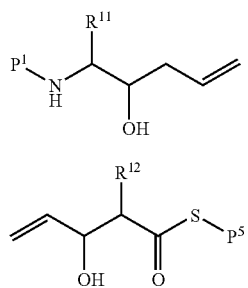

(XI)

(XIII)

by first reacting the free alcohols with a silicon protecting group, and then treating the resulting compound with a ruthenium catalyst, giving a compound of the formula (VII);

wherein, each $R^{11}$ and $R^{12}$ is independently alkyl substituted with aryl or heteroaryl, each of which is optionally substituted with 1-5 substituents selected from $OR^6$, CN, $NO_2$, $NHR^{17}$, $N(R^{17})_2$, halo, $CONHR^{17}$, $CON(R^{17})_2$, $CO_2R^{18}$, or $C_{1-6}$ alkyl;

each $R^{16}$ is independently H, alkyl, or $P^3$;

each $R^{17}$ is independently H, alkyl, acyl, or $P^4$;

each $R^{18}$ is independently H, alkyl, aralkyl, or heteroaralkyl;

each $P^1$ and $P^4$ is independently a nitrogen protecting group; and each $P^3$ is independently an oxygen protecting group; and $P^5$ is a sulfur protecting group.

In some aspects, the ruthenium catalyst is $Cl_2(PCy_3)(IMesH_2)RuCHPh$, $Cl_2(PCy_3)_2RuCHPh$, $Cl_2(PCy_3)(IMes)RuCHPh$, or a compound of formula (XV)

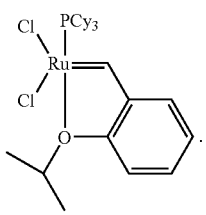

(XV)

In certain aspects, the ruthenium catalyst is $Cl_2(PCy_3)(IMesH_2)RuCHPh$.

In one aspect, the invention is a method of making a compound of the formula (XIV):

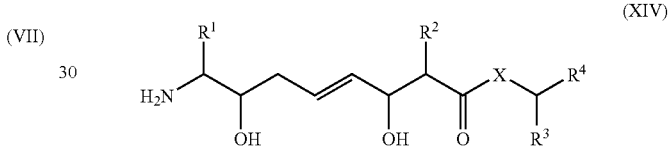

(XIV)

including coupling compounds of formulas (XI) and (XIII),

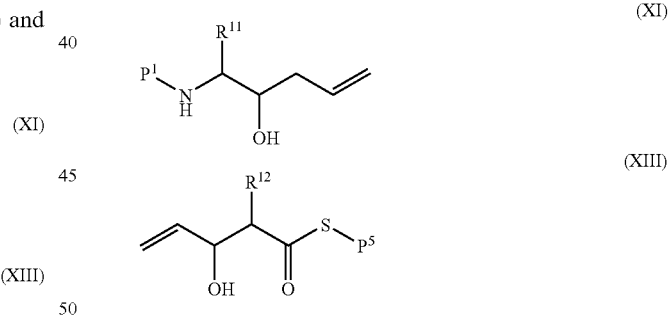

(XI)

(XIII)

with a ruthenium catalyst;

treating the resulting compound with peroxide and base under conditions sufficient to hydrolyze the thioester;

amidation or esterification of the resulting acid; and treatment of the resulting compound with a deprotecting agent sufficient to remove protecting groups, giving a compound of the formula (XIV);

wherein, each $R^1$, $R^2$, and $R^3$ is independently alkyl substituted with aryl or heteroaryl, each of which is optionally substituted with 1-5 substituents selected from $OR^6$, CN, $NO_2$, $NHR^7$, $N(R^7)_2$, halo, $CONHR^7$, $CON(R^7)_2$, $CO_2R^8$, or $C_{1-6}$ alkyl;

X is N or O;

$R^4$ is H, $CON(R^7)_2$, $CONHR^7$, $CH_2OH$, or $CH(OH)CH=CH_2$;

each $R^6$ is independently H, alkyl, or $P^3$;
each $R^7$ is independently H, alkyl, acyl, or $P^4$;
each $R^8$ is independently H, alkyl, aralkyl, or heteroaralkyl;
each $R^{11}$ and $R^{12}$ are independently alkyl substituted with aryl or heteroaryl, each of which is optionally substituted with 1-5 substituents selected from $OR^{16}$, CN, $NO_2$, $NHR^{17}$, $N(R^{17})_2$, halo, $CONHR^{17}$, $CON(R^7)_2$, $CO_2R^{18}$, or $C_{1-6}$ alkyl;
each $R^{16}$ is independently H, alkyl, or $P^3$;
each $R^{17}$ is independently H, alkyl, acyl, or $P^4$;
each $R^{18}$ is independently H, alkyl, aralkyl, or heteroaralkyl;
each $P^1$ and $P^4$ is independently a nitrogen protecting group;
each $P^3$ is independently an oxygen protecting group; and
$P^5$ is a sulfur protecting group.

In certain aspects, the deprotecting agent is an acid and $P^1$ is acid labile.

In certain aspects, $P^1$ is Boc or Fmoc; and $P^3$ is t-Bu, Bn, Me, Ac, or TBS.

In some aspects, the ruthenium catalyst is $Cl_2(PCy_3)(IMesH_2)RuCHPh$, $Cl_2(PCy_3)_2RuCHPh$, $Cl_2(PCy_3)(IMes)RuCHPh$, or a compound of formula (XV)

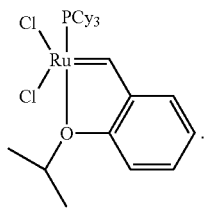

(XV)

In some aspects, the ruthenium catalyst is $Cl_2(PCy_3)(IMesH_2)RuCHPh$.

In one aspect, the invention is a method of making a compound of formula (XVII):

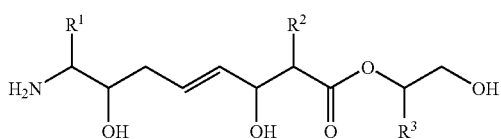

(XVII)

including coupling compounds of formulas (XI) and (XIII)

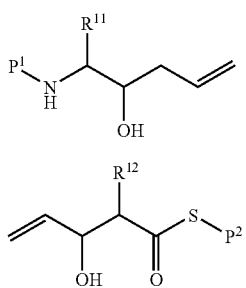

(XI)

(XIII)

with a ruthenium catalyst;
treating the resulting compound with peroxide and base under conditions sufficient to hydrolyze the thioester; and
reacting the free hydroxyls with an oxygen protecting group to give a compound of formula (XVIII)

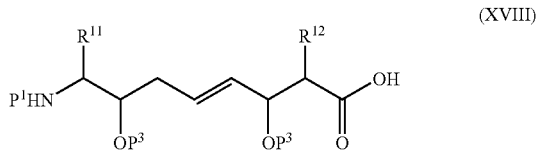

(XVIII)

coupling the compound of formula (XVIII) with an alcohol of formula $R^{13}(CHOH)CHOR^{16}$; and
treating the resulting compound with a deprotecting agent sufficient to remove protecting groups to give a compound of formula (XVII);

wherein,
each $R^1$, $R^2$, and $R^3$ is independently alkyl substituted with aryl or heteroaryl, each of which is optionally substituted with 1-5 substituents selected from $OR^6$, CN, $NO_2$, $NHR^7$, $N(R^7)_2$, halo, $CONHR^7$, $CON(R^7)_2$, $CO_2R^8$, or $C_{1-6}$ alkyl;
each $R^6$ is independently H, alkyl, or $P^3$;
each $R^7$ is independently H, alkyl, acyl, or $P^4$;
each $R^8$ is independently H, alkyl, aralkyl, or heteroaralkyl;
each $R^{11}$, $R^{12}$, and $R^{13}$ is independently alkyl substituted with aryl or heteroaryl, each of which is optionally substituted with 1-5 substituents selected from $OR^{16}$, CN, $NO_2$, $NHR^{17}$, $N(R^{17})_2$, halo, $CONHR^{17}$, $CON(R^{17})_2$ $CO_2R^{18}$, or $C_{1-6}$ alkyl;
each $R^{16}$ is independently H, alkyl, or $P^3$;
each $R^{17}$ is independently H, alkyl, acyl, or $P^4$;
each $R^{18}$ is independently H, alkyl, aralkyl, or heteroaralkyl;
each $P^1$ and $P^4$ is independently a nitrogen protecting group; and
each $P^3$ is independently an oxygen protecting group; and
$P^5$ is a sulfur protecting group.

In some aspects, the deprotecting agent is an acid, and $P^1$ and $P^3$ are acid labile.

In some aspects, $P^1$ is Boc or Fmoc; and $P^3$ is t-Bu, Bn, Me, Ac, or TBS.

In some aspects, the ruthenium catalyst is $Cl_2(PCy_3)(IMesH_2)RuCHPh$, $Cl_2(PCy_3)_2RuCHPh$, $Cl_2(PCy_3)(IMes)RuCHPh$, or a compound of formula (XV)

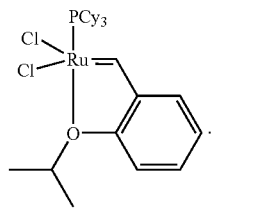

(XV)

In some aspects, the ruthenium catalyst is $Cl_2(PCy_3)(IMesH_2)RuCHPh$.

In another aspect, the invention is a composition comprising a compound of formula (I) and a pharmaceutically acceptable carrier.

In some instances, the composition includes an additional therapeutic agent.

In some instances, the additional therapeutic agent is an analgesic agent.

In some instances, the analgesic agent is morphine or codeine.

In another aspect, the invention is a method of treating a mu opioid receptor (MOR) mediated disorder in a subject identified as in need of such treatment including administering a compound of formula (I).

In yet another aspect, the invention is a method of treating a mu opioid receptor (MOR) mediated disorder in a subject identified as in need of such treatment including administering a composition including a compound of formula (I).

In still another aspect, the invention is a method of making a pharmaceutical composition including combining a compound of formula (I) and a pharmaceutically acceptable carrier.

In some instances, the composition can also include an additional therapeutic agent.

In another aspect, the invention is a method of treating pain in a subject, including administering to the subject in need of such treatment a compound of formula (I).

In another aspect, the invention is a library of compounds of formula (I).

In yet another aspect, the invention is a method of making a library of compounds of formula (I) including:
a) providing a plurality of compounds of formula (XI);
b) providing a plurality of compounds of formula (XII); and
c) reacting the compounds of formula (XI) with the compounds of formula (XII) to provide the library of compounds of formula (I).

In still another aspect, the invention is a method of making a library of compounds of formula (I) including:
a) providing a plurality of compounds of formula (XI);
b) providing a plurality of compounds of formula (XIII); and
c) reacting the compounds of formula (XI) with the compounds of formula (XIII) to provide the library of compounds of formula (I).

In one aspect, the invention is a compound of formula (XIX):

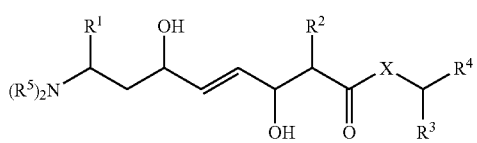

(XIX)

wherein,
each $R^1$, $R^2$, and $R^3$ is independently alkyl substituted with aryl or heteroaryl, each of which is optionally substituted with 1-5 substituents selected from $OR^6$, CN, $NO_2$, $NHR^7$, $N(R^7)_2$, halo, $CONHR^7$, $CON(R^7)_2$, $CO_2R^8$, or $C_{1-6}$ alkyl;
X is N, O, or S;
$R^4$ is H, $CON(R^7)_2$, $CONHR^7$, $CH_2OH$, $CH(OH)CH{=}CH_2$, or $C(O)NHCHR^{10}CO_2H$;
each $R^5$ is independently H, alkyl, alkenyl, aryl, heteroaryl, acyl, $P^1$, or $C(O)CHR^{10}NH_2$;
each $R^6$ is independently H, alkyl, or $P^3$;
each $R^7$ is independently H, alkyl, acyl, or $P^2$;
each $R^8$ is independently H, alkyl, aralkyl, or heteroaralkyl;
each $R^{10}$ is independently an amino acid side chain;
each $P^1$ and $P^2$ is independently a nitrogen protecting group; and
each $P^3$ is independently an oxygen protecting group;
or pharmaceutically acceptable salts thereof.

In another aspect, the invention is a compound of formula (XIX) wherein:
X is N or O;
$R^1$ is alkyl substituted with aryl, which is optionally substituted with 1-5 substituents selected from $OR^6$, CN, $NO_2$, $NHR^7$, $N(R^7)_2$, halo, $CONHR^7$, $CON(R^7)_2$, $CO_2R^8$, or $C_{1-6}$ alkyl;
$R^4$ is H, $CON(R^7)_2$, $C(O)NHCHR^{10}CO_2H$, or $CH_2OH$; and
each $R^5$ is independently H, alkyl, acyl, $P^1$, or $C(O)CHR^{10}NH_2$;
each $R^{10}$ is independently an amino acid side chain.

In yet another aspect, the invention is a compound of formula (XIX), wherein:
X is N or O;
$R^1$ is alkyl substituted with aryl, which is optionally substituted with 1-5 substituents selected from $OR^6$, CN, $NO_2$, halo, or $C_{1-6}$ alkyl;
$R^4$ is H, $CONHR^7$, or $CH_2OH$;
each $R^5$ is independently H or alkyl;
each $R^6$ is independently H or alkyl; and
$R^7$ is H, alkyl, or $P^2$.

In still another aspect, the invention is a compound of formula (XIX), wherein:
X is N or O;
$R^1$ is alkyl substituted with aryl, which is optionally substituted with 1-5 substituents selected from OH or $C_{1-6}$ alkyl; and
$R_4$ is H, $CONH_2$, or $CH_2OH$.

In still another aspect, the invention is a compound of formula (XIX), wherein:
X is N or O;
$R^1$ is $C_1$ alkyl substituted with phenyl, which is substituted at the 2- and 6-positions with Me and is substituted at the 4-position with OH; and
$R^4$ is H, $CONH_2$, or $CH_2OH$.

In still another aspect, the invention is a compound of formula (XIX), wherein
X is N;
$R^1$ is methyl substituted with phenyl, which is substituted at the 4-position with OH; and $R^4$ is $CONH_2$.

In one aspect, the invention is a compound of formula (XX):

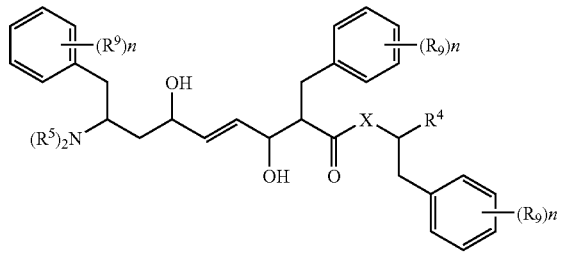

(XX)

wherein,
X is N or O;
$R^4$ is H, $CON(R^7)_2$, $CONHR^7$, $CH_2OH$, or $C(O)NHCHR^{10}CO_2H$;
each $R^5$ is independently H, alkyl, acyl, $P^1$, or $C(O)CHR^{10}NH_2$;
each $R^6$ is independently H, alkyl, or $P^3$;
each $R^7$ is independently H, alkyl, acyl, or $P^2$;
each $R^8$ is independently H, alkyl, aralkyl, or heteroaralkyl;

each $R^9$ is independently $OR^6$, CN, $NO_2$, $NHR^7$, $N(R^7)_2$, halo, $CONHR^7$, $CON(R^7)_2$, $CO_2R^8$, or $C_{1-6}$ alkyl;

each $R^{10}$ is independently an amino acid side chain;

each n is independently 0, 1, 2, 3, 4, or 5;

each $P^1$ and $P^2$ is independently a nitrogen protecting group; and each $P^3$ is independently an oxygen protecting group.

In another aspect, the invention is a compound of formula (XX), wherein:

$R^4$ is H, $CON(R^7)_2$, $CONHR^7$, or $CH_2OH$;

each $R^5$ is independently H, alkyl or acyl;

each $R^6$ is independently H or alkyl;

each $R^7$ is independently H or alkyl;

each $R^9$ is independently $OR^6$, CN, $NO_2$, halo, or $C_{1-6}$ alkyl; and each n is independently 0, 1, 2, or 3.

In yet another aspect, the invention is a compound of formula (XX), wherein:

$R^4$ is H, $CON(R^7)_2$, $CONHR^7$, or $CH_2OH$;

each $R^5$ is independently H, alkyl, acyl, or $P^1$;

each $R^6$ is independently H or $P^3$;

each $R^7$ is independently H or $P^2$;

each $R^9$ is independently $OR^6$ or $C_{1-6}$ alkyl;

each n is independently 0 or 1;

$P^1$ is a BOC;

$P^2$ is a solid support; and $P^3$ is t-Bu.

In still another aspect, the invention is a compound of formula (XX), wherein:

$R^4$ is H, $CONH_2$, or $CH_2OH$;

each $R^5$ is independently H, $P^1$, or $C(O)CHR^{10}NH_2$;

each $R^6$ is H or alkyl each $R^9$ is $C_{1-6}$ alkyl or $OR^6$;

each $R^{10}$ is independently an amino acid side chain;

each n is independently 1, 2, or 3; and $P^1$ is a nitrogen protecting group.

In one aspect, the invention is a compound of formula (XXI)

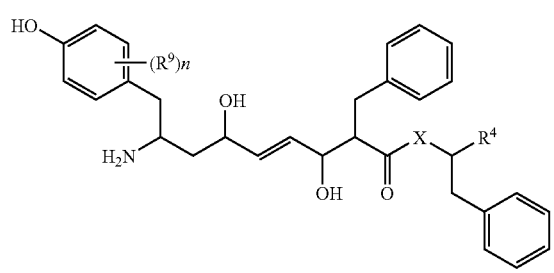

(XXI)

wherein,

X is O or N;

$R^4$ is H, $CONH_2$, or $CH_2OH$;

$R^9$ is $C_{1-6}$ alkyl; and n is 2.

In one aspect, the invention is a compound of formula (XXII):

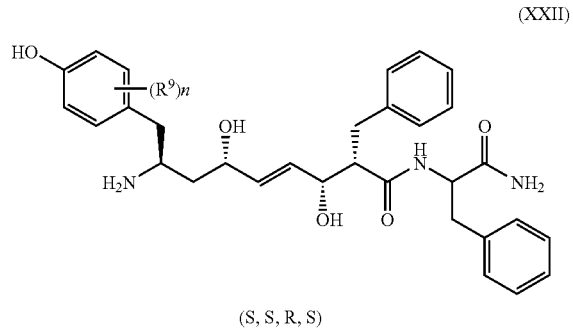

(XXII)

(S, S, R, S)

wherein $R^9$ is $C_{1-6}$ alkyl; and n is 0, 1, or 2.

In one aspect, the invention is a compound of formula (XXIV):

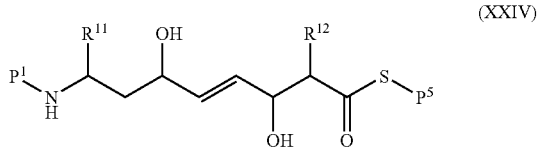

(XXIV)

wherein, each $R^{11}$ and $R^{12}$ is independently alkyl substituted with aryl or heteroaryl, each of which is optionally substituted with 1-5 substituents selected from $OR^{16}$, CN, $NO_2$, $NHR^{17}$, $N(R^{17})_2$, halo, $CONHR^{17}$, $CON(R^{17})_2$ $CO_2R^8$, or $C_{1-6}$ alkyl;

each $R^{16}$ is independently H, alkyl or $P^3$;

each $R^{17}$ is independently H, alkyl acyl, or $P^4$;

each $R^{18}$ is independently H, alkyl, aralkyl, or heteroaralkyl;

each $P^1$ and $P^4$ is independently a nitrogen protecting group; and each $P^3$ is independently an oxygen protecting group; and $P^5$ is a sulfur protecting group;

or pharmaceutical salts thereof.

In another aspect, the invention is a compound of formula (XXIV), wherein:

each $R^{11}$, and $R^{12}$ is independently alkyl substituted with aryl or heteroaryl, each of which is optionally substituted with 1-5 substituents selected from $OR^{16}$ or $C_{1-6}$ alkyl; and each $R^{16}$ is independently H, alkyl, or $P^3$;

In one aspect, the invention is a method of making a compound of the formula (XXIII):

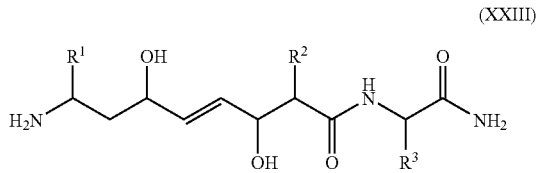

(XXIII)

including treating the compound of formula (XXIV)

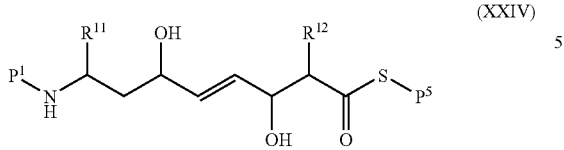

(XXIV)

with peroxide and base under conditions sufficient to hydrolyze the thioester;

coupling the resulting product with a solid phase peptide; and treating the resulting compound with a deprotecting agent, giving a compound of the formula (XXIII);

wherein, each $R^1$, $R^2$, and $R^3$ is independently alkyl substituted with aryl or heteroaryl, each of which is optionally substituted with 1-5 substituents selected from $OR^6$, CN, $NO_2$, $NHR^7$, $N(R^7)_2$, halo, $CONHR^7$, $CON(R^7)_2$, $CO_2R^8$, or $C_{1-6}$ alkyl;

each $R^6$ is independently H, alkyl, or $P^3$;

each $R^7$ is independently H, alkyl, acyl, or $P^4$;

each $R^8$ is independently H, alkyl, aralkyl, or heteroaralkyl;

each $R^{11}$ and $R^{12}$ is independently alkyl substituted with aryl or heteroaryl, each of which is optionally substituted with 1-5 substituents selected from $OR^{16}$, CN, $NO_2$, $NHR^{17}$, $N(R^7)_2$, halo, $CONHR^{17}$, $CON(R^{17})_2$, $CO_2R^{18}$, or $C_{1-6}$ alkyl;

each $R^{16}$ is independently H, alkyl, or $P^3$;

each $R^{17}$ is independently H, alkyl, acyl, or $P^4$;

each $R^{18}$ is independently H, alkyl, aralkyl, or heteroaralkyl;

each $P^1$ and $P^4$ is independently a nitrogen protecting group; and each $P^3$ is independently an oxygen protecting group; and $P^5$ is a sulfur protecting group.

In certain aspects, the deprotecting agent is an acid.

In certain aspects, the deprotecting agent is an acid; $P^1$ is Boc or Fmoc; $P^3$ is t-Bu, Bn, Me, Ac, or TBS; and $P^5$ is Bn.

In one aspect, the invention is a method of making a compound of formula (XXIII):

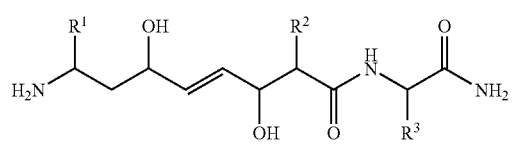

(XXIII)

including coupling compounds of formulas (XXV) and (XIII)

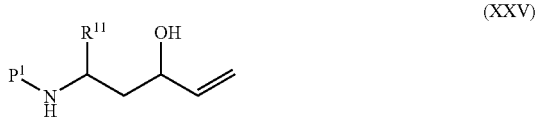

(XXV)

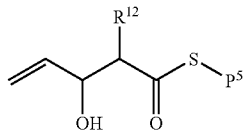

(XIII)

using a ruthenium catalyst, giving a compound of the formula (XXIV);

treating the resulting product with peroxide and base under conditions sufficient to hydrolyze the thioester;

coupling the resulting product with a solid phase peptide; and treating the resulting compound with a deprotecting agent, giving a compound of the formula (XXIII);

wherein, each $R^1$, $R^2$, and $R^3$ is independently alkyl substituted with aryl or heteroaryl, each of which is optionally substituted with 1-5 substituents selected from $OR^6$, CN, $NO_2$, $NHR^7$, $N(R^7)_2$, halo, $CONHR^7$, $CON(R^{17})_2$, $CO_2R^8$, or $C_{1-6}$ alkyl;

each $R^6$ is independently H, alkyl, or $P^3$;

each $R^7$ is independently H, alkyl, acyl, or $P^4$;

each $R^8$ is independently H, alkyl, aralkyl, or heteroaralkyl;

each $R^{11}$ and $R^{12}$ is independently alkyl substituted with aryl or heteroaryl, each of which is optionally substituted with 1-5 substituents selected from $OR^6$, CN, $NO_2$, $NHR^{17}$, N $(R^7)_2$, halo, $CONHR^7$, $CON(R^{17})_2$, $CO_2R^1$ 8, or $C_{1-6}$ alkyl;

each $R^{16}$ is independently H, alkyl, or $P^3$;

each $R^{17}$ is independently H, alkyl, acyl, or $P^4$;

each $R^{18}$ is independently H, alkyl, aralkyl, or heteroaralkyl;

each $P^1$ and $P^4$ is independently a nitrogen protecting group; and each $P^3$ is independently an oxygen protecting group; and $P^5$ is a sulfur protecting group.

In certain aspects, the deprotecting agent is an acid.

In certain aspects, $P^1$ is Boc or Fmoc; $P^3$ is t-Bu, Bn, Me, Ac, or TBS; and $P^5$ is Bn.

In certain aspects, the ruthenium catalyst is [1,3-bis-(2,4,6-trimethylphenyl)-2-imidazolidinylidene dichloro(phenylmethylene)-(tricyclohexylphosphine)ruthenium].

In another aspect, the invention is a composition including a compound of formula (XIX) and a pharmaceutically acceptable carrier.

In some instances, the composition includes an additional therapeutic agent.

In some instances, the additional therapeutic agent is an analgesic agent.

In some instances, the analgesic agent is morphine or codeine.

In another aspect, the invention is a method of treating a mu opioid receptor (MOR) mediated disorder in a subject identified as in need of such treatment including administering a compound of formula (XIX).

In yet another aspect, the invention is a method of treating a mu opioid receptor (MOR) mediated disorder in a subject identified as in need of such treatment including administering a composition including a compound of formula (XIX).

In still another aspect, the invention is a method of making a pharmaceutical composition including combining a compound of formula (XIX) and a pharmaceutically acceptable carrier.

In some instances, the composition can also include an additional therapeutic agent.

In another aspect, the invention is a method of treating pain in a subject, including administering to the subject in need of such treatment a compound of the formula (XIX).

In another aspect, the invention is a library of compounds of formula (XIX).

In yet another aspect, the invention is a method of making a library of compounds of formula (XIX) including:

a) providing a plurality of compounds of formula (XIII);
b) providing a plurality of compounds of formula (XXV); and
c) reacting the compounds of formula (XIII) with the compounds of formula (XXV) to provide the library of compounds of formula (XIX).

In one aspect, the compounds exhibit preferential selectivity (e.g., any integer between 5 and 170 fold, 75 and 150 fold, 50 and 100 fold, and 5 and 20 fold) for MOR over the delta opioid receptor (DOR).

In one aspect, the compounds exhibit preferential selectivity (e.g., any integer between 5 and 600 fold, 100 and 400 fold, 75 and 150 fold, 50 and 100 fold, and 5 and 20 fold) for MOR over the kappa opioid receptor (KOR).

In other aspects, the compounds, compositions, and methods delineated herein are (or include) those of any of the compounds of Table 1 herein.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
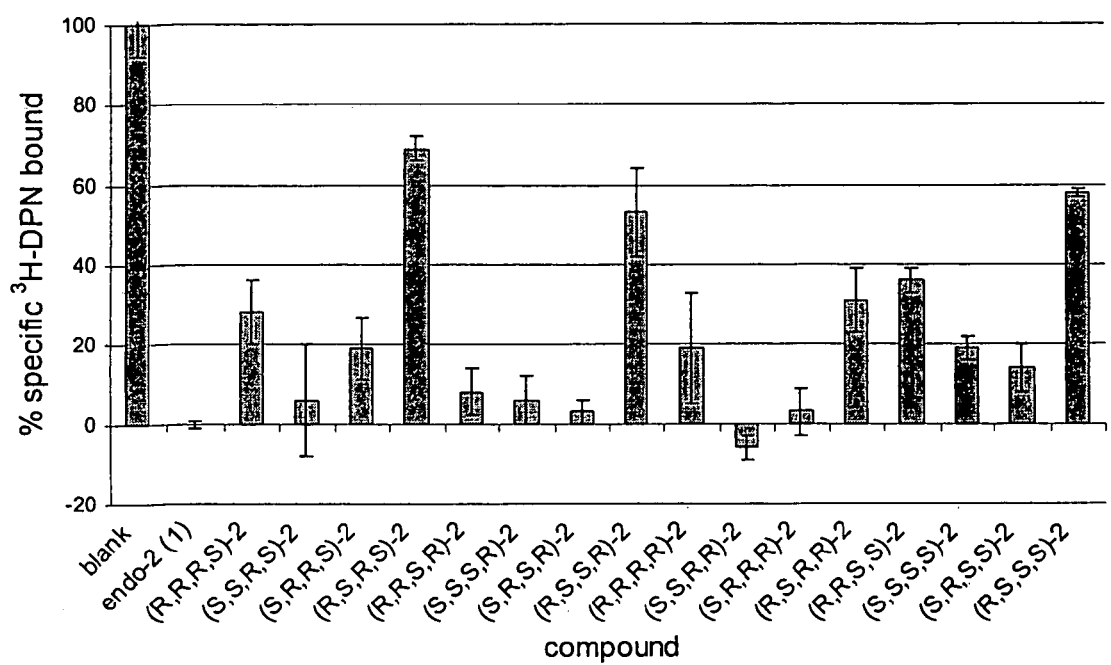
FIG. 1 is a bar graph depicting the binding of Mu Opioid Receptor ligands of compounds 1 and 2.

The term "halo" refers to any radical of fluorine, chlorine, bromine or iodine. The term "alkyl" refers to a hydrocarbon chain that may be a straight chain or branched chain, containing the indicated number of carbon atoms. For example, $C_1$-$C_{10}$ indicates that the group may have from 1 to 10 (inclusive) carbon atoms in it. The term "lower alkyl" refers to a $C_1$-$C_8$ alkyl chain. In the absence of any numerical designation, "alkyl" is a chain (straight or branched) having 1 to 10 (inclusive)-carbon atoms in it. The term "alkoxy" refers to an —O-alkyl radical. The term "alkylene" refers to a divalent alkyl (i.e., —R—). The term "alkylenedioxo" refers to a divalent species of the structure —O—R—O—, in which R represents an alkylene. The term "aminoalkyl" refers to an alkyl substituted with an amino. The term "mercapto" refers to an —SH radical. The term "thioalkoxy" refers to an —S-alkyl radical.

The term "aryl" refers to a 6-carbon monocyclic or 10-carbon bicyclic aromatic ring system wherein 0, 1, 2, 3, or 4 atoms of each ring may be substituted by a substituent. Examples of aryl groups include phenyl, naphthyl and the like. The term "arylalkyl" or the term "aralkyl" refers to alkyl substituted with an aryl. The term "arylalkoxy" refers to an alkoxy substituted with aryl.

The term "cycloalkyl" as employed herein includes saturated and partially unsaturated cyclic hydrocarbon groups having 3 to 12 carbons, preferably 3 to 8 carbons, and more preferably 3 to 6 carbons, wherein the cycloalkyl group additionally may be optionally substituted. Preferred cycloalkyl groups include, without limitation, cyclopropyl, cyclobutyl, cyclopentyl, cyclopentenyl, cyclohexyl, cyclohexenyl, cycloheptyl, and cyclooctyl.

The term "heteroaryl" refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2, 3, or 4 atoms of each ring may be substituted by a substituent. Examples of heteroaryl groups include pyridyl, furyl or furanyl, imidazolyl, benzimidazolyl, pyrimidinyl, thiophenyl or thienyl, quinolinyl, indolyl, thiazolyl, and the like. The term "heteroarylalkyl" or the term "heteroaralkyl" refers to an alkyl substituted with a heteroaryl. The term "heteroarylalkoxy" refers to an alkoxy substituted with heteroaryl.

The term "heterocyclyl" refers to a nonaromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2 or 3 atoms of each ring may be substituted by a substituent. Examples of heterocyclyl groups include piperazinyl, pyrrolidinyl, dioxanyl, morpholinyl, tetrahydrofuranyl, and the like.

The term "oxo" refers to an oxygen atom, which forms a carbonyl when attached to carbon, an N-oxide when attached to nitrogen, and a sulfoxide or sulfone when attached to sulfur.

The term "acyl" refers to an alkylcarbonyl, cycloalkylcarbonyl, arylcarbonyl, heterocyclylcarbonyl, or heteroarylcarbonyl substituent, any of which may be further substituted by substituents.

The term "amino acid" refers to a molecule containing both an amino group and a carboyxl group. Suitable amino acids include, without limitation, both the D- and L-isomers of the 20 naturally occurring amino acids found in peptides (e.g., A, R, N, C, D, Q, E, C, H, I, L, K, M, F, P, S, T, W, Y, V (as known by the one letter abbreviations)) as well as unnaturally occurring amino acids prepared by organic synthesis or other metabolic routes.

The term "amino acid side chain" refers to any one of the twenty groups attached to the α-carbon in naturally occurring amino acids. For example, the amino acid side chain for alanine is methyl, the amino acid side chain for phenylalanine is phenylmethyl, the amino acid side chain for cysteine is thiomethyl, the amino acid side chain for aspartate is carboxymethyl, the amino acid side chain for tyrosine is 4-hydroxyphenylmethyl, etc.

The term "substituents" refers to a group "substituted" on an alkyl, cycloalkyl, aryl, heterocyclyl, or heteroaryl group at any atom of that group. Suitable substituents include, without limitation, halo, hydroxy, mercapto, oxo, nitro, haloalkyl, alkyl, alkaryl, aryl, aralkyl, alkoxy, thioalkoxy, aryloxy, amino, alkoxycarbonyl, amido, carboxy, alkanesulfonyl, alkylcarbonyl, and cyano groups.

The symbol "⤢" when used as part of a molecular structure refers to a single bond or a trans or cis double bond.

The symbol "⁄" (a line with no group attached to one end), when used as part of a molecular structure, refers to a Me group.

The term "Boc" means N-tert-Butoxycarbonyl.
The term "Fmoc" means 9-fluorenylmethoxycarbonyl.
The term "t-Bu" means tert-butyl.
The term "Bn" means benzyl.
The term "Me" means methyl.
The term "Ac" means acetyl.
The term "TBS" means tert-butyldimethylsilyl.
The term "solid support" refers a material to which a compound is attached to facilitate identification, isolation, purification, or chemical reaction selectivity of the compound. Such materials are known in the art and include, for example, beads, pellets, disks, fibers, gels, or particles such as cellulose beads, pore-glass beads, silica gels, polystyrene beads optionally cross-linked with divinylbenzene and optionally grafted with polyethylene glycol, poly-acrylamide beads, latex beads, dimethylacrylamide beads optionally cross-linked with N,N'-bis-acryloyl ethylene diamine, glass particles coated with hydrophobic polymer, and material having a rigid or semi-rigid surface. The solid supports optionally have functional groups such as amino, hydroxy, carboxy, or halo groups, (see, Obrecht, D. and Villalgrodo, J. M., *Solid-Supported Combinatorial and Parallel Synthesis of Small-Molecular-Weight Compound Libraries*, Pergamon-Elsevier Science Limited (1998)), and include those useful in techniques such as the "split and pool" or "parallel" synthesis techniques, solid-phase and solution-phase techniques, and encoding techniques (see, for example, Czamik, A. W., *Curr Opin. Chem. Bio.*, (1997) 1, 60).

The term "solid phase peptide" refers to an amino acid, which is chemically bonded to a resin (e.g., a solid support). Resins are generally commercially available (e.g., from SigmaAldrich). Some examples of resins include Rink-resins, Tentagel S RAM, MBHA, and BHA-resins.

TABLE 1

Representative compounds of the invention

Compound 2

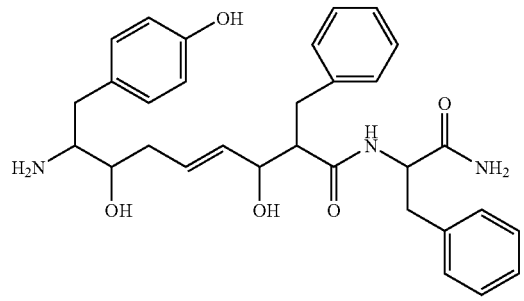

Compound 6

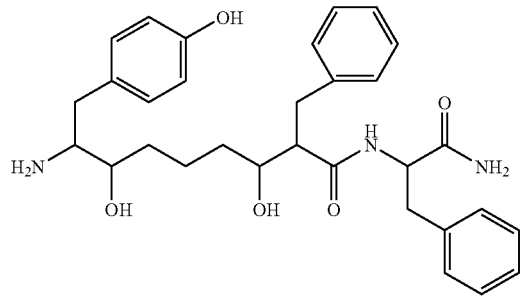

Compound 8

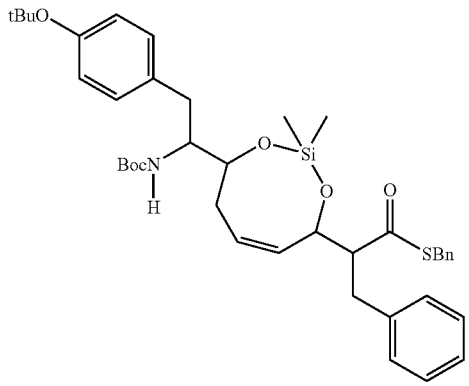

TABLE 1-continued
Representative compounds of the invention
Compound 9
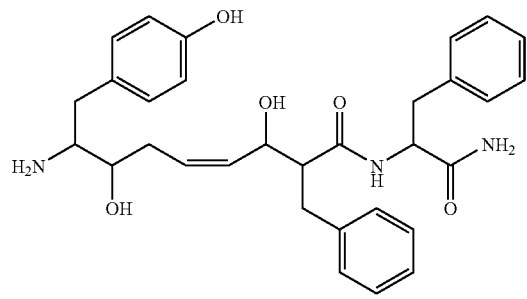
Compound 10
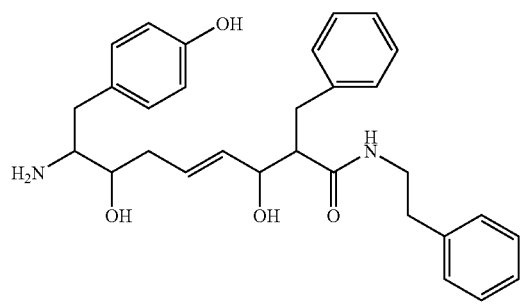
Compound 11
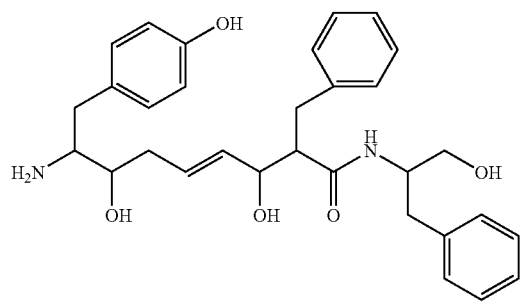
Compound 12
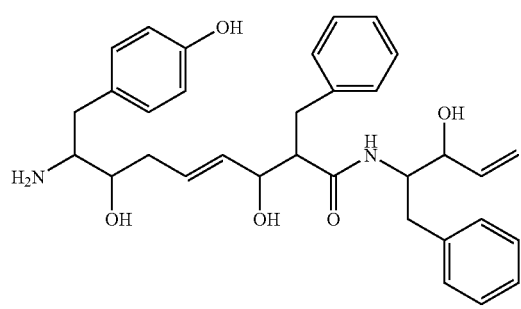
Compound 13
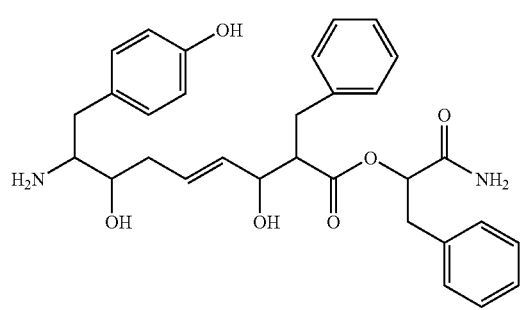

TABLE 1-continued
Representative compounds of the invention
Compound 25
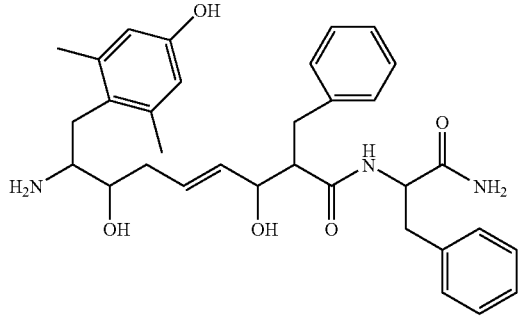
Compound 26
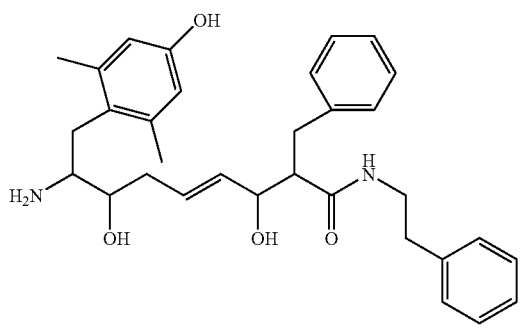
Compound 27
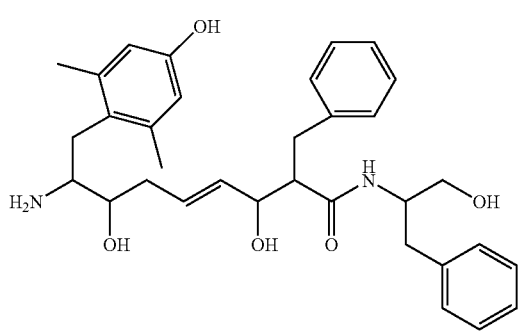
Compound 28
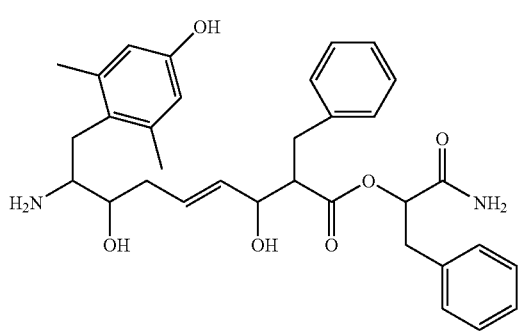

TABLE 1-continued
Representative compounds of the invention
Compound 29
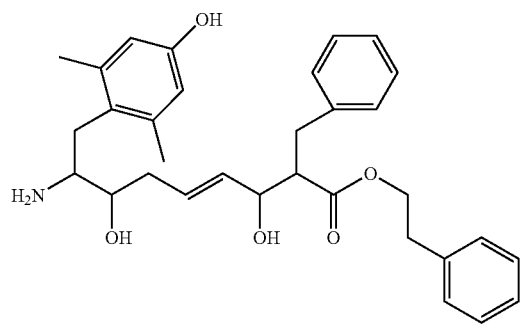
Compound 30
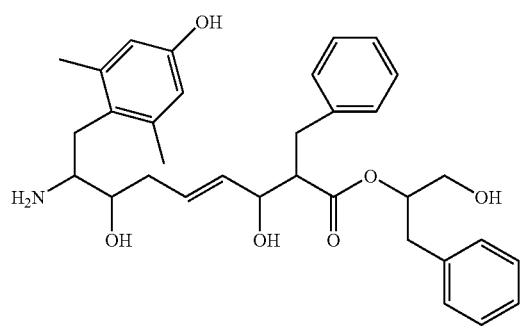
Compound 34
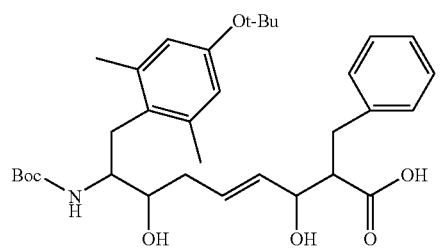
Compound 35
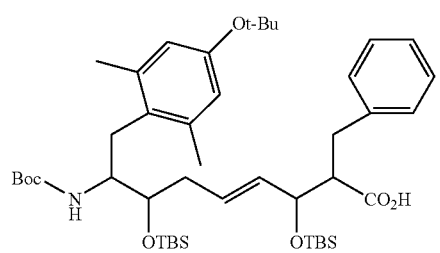
Compound 43
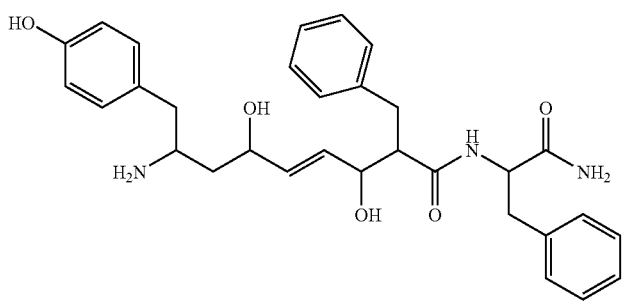

TABLE 1-continued

Representative compounds of the invention

Compound 49

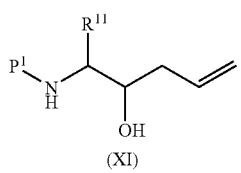

Other aspects of this invention relate to a composition having a compound of any of the formulae described herein and a pharmaceutically acceptable carrier; or a compound of any of the formulae described herein, an additional therapeutic agent, and a pharmaceutically acceptable carrier; or a compound of any of the formulae described herein, an additional therapeutic agent, and a pharmaceutically acceptable carrier, wherein the additional therapeutic agent is an MOR binding agent.

Yet another aspect of this invention relates to a method of treating a subject (e.g., mammal) having a mu opioid receptor mediated disorder or disorder symptom (including, but not limited to pain). The method includes administering to the subject (including a subject identified as in need of such treatment) an effective amount of a compound described herein, or a composition described herein to produce such effect. Identifying a subject in need of such treatment can be in the judgment of a subject or a health care professional and can be subjective (e.g. opinion) or objective (e.g. measurable by a test or diagnostic method).

The invention further relates to a product (i.e., a compound of any of the formulae herein) made by the methods described above. Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

As can be appreciated by the skilled artisan, further methods of synthesizing the compounds of the formulae herein will be evident to those of ordinary skill in the art. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, *Comprehensive Organic Transformations*, VCH Publishers (1989); T. W. Greene and P. G. M. Wuts, *Protective Groups in Organic Synthesis*, 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

Synthesis of Stereodiverse, Non-peptidic Compounds

Compounds of the formula (VIII) are prepared by coupling compounds of formulas (XI) and (XII) with a ruthenium catalyst, followed by treatment with a deprotecting agent to give a compound of formula (VIII).

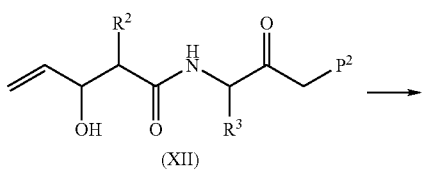

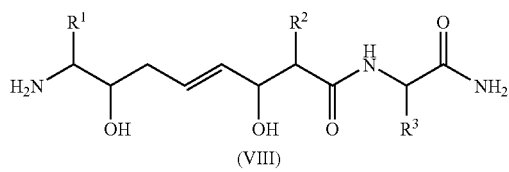

Compounds of the formula (X) are prepared by coupling compounds of formulas (XI) and (XII) as above, treating the resulting product with a reagent that reductively transfers two hydrogen atoms from the reagent to an olefin, and treating the reduced compound with a deprotecting agent, to give a compound of formula (X).

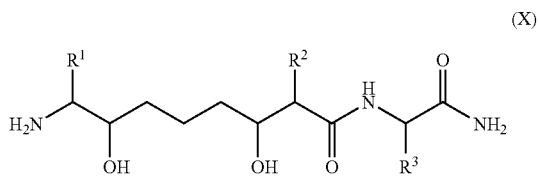

Compounds of the formula (XIV) are prepared by coupling compounds of formulas (XI) and (XIII) with a ruthenium catalyst, followed by hydrolysis of the thioester, coupling of the resulting carboxylic acid with an alcohol or an amine, and deprotection, to give a compound of formula (XIV).

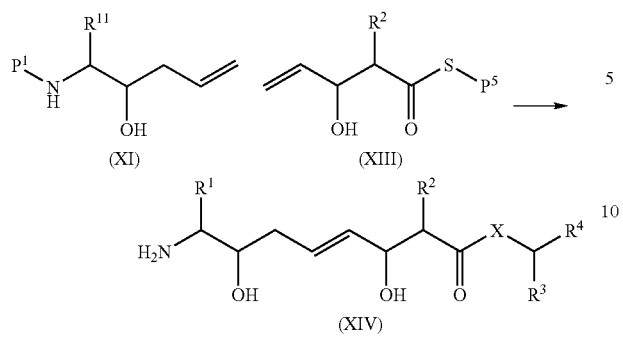

Compounds of the formula (XVII) are prepared by coupling compounds of formulas (XI) and (XIII) with a ruthenium catalyst, hydrolyzing the resulting compound, and reacting the free alcohols with a protecting group (e.g., a silicon coupling group) to give the compound of formula (XVIII).

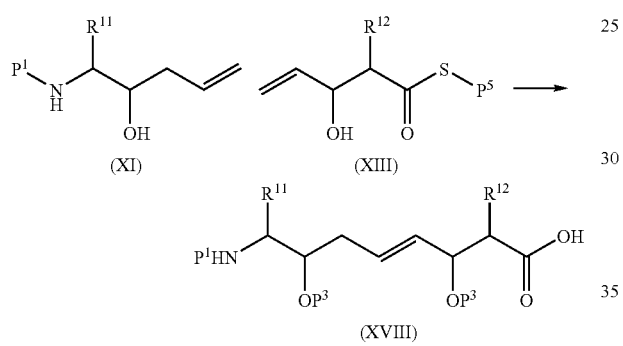

The compound of formula (XVIII) is coupled with an alcohol of formula $R^{13}$(CHOH)CHO$R^{16}$, and the resulting compound is treated with a deprotecting agent to give the compound of formula (XVII).

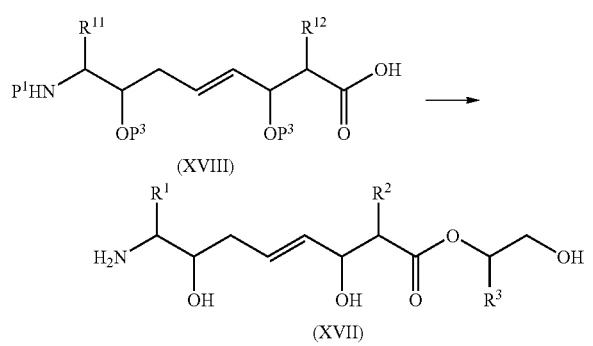

Compounds, of the formula (XVI) are prepared by coupling compounds of formulas (XI) and (XIII) by first reacting the free alcohols with a silicon coupling group, having at least two nucleophilic displaceable groups (e.g., leaving groups, halo, SiMe$_2$Cl$_2$) and then treating the resulting compound with a ruthenium catalyst; the resulting compound is then treated with a deprotecting agent, resulting in a compound of formula (XVI).

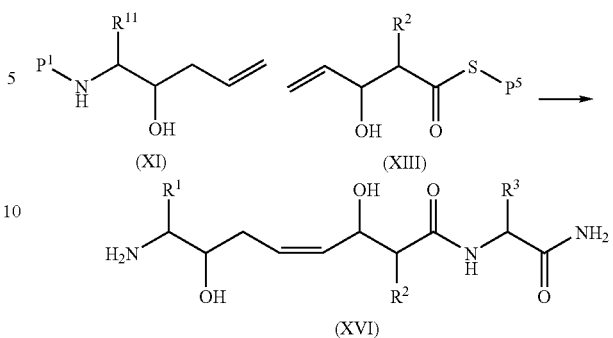

Compounds of the formula (XXIII) are prepared by coupling compounds of formulas (XXV) and (XIII) with a ruthenium catalyst, hydrolyzing the thioester, coupling the resulting carboxylic acid with a solid phase peptide, and treating the resulting compound with a deprotecting agent, giving a compound of formula (XXIII).

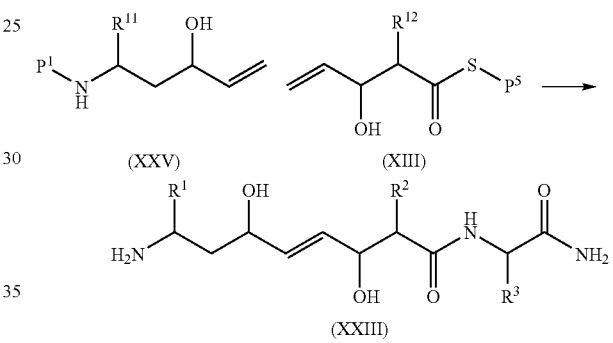

The compounds of this invention may contain one or more asymmetric centers and thus occur as racemates and racemic mixtures, single enantiomers, individual diastereomers and diastereomeric mixtures. All such isomeric forms of these compounds are expressly included in the present invention. The compounds of this invention may also be represented in multiple tautomeric forms, in such instances, the invention expressly includes all tautomeric forms of the compounds described herein (e.g., alkylation of a ring system may result in alkylation at multiple sites, the invention expressly includes all such reaction products). All such isomeric forms of such compounds are expressly included in the present invention. All crystal forms of the compounds described herein are expressly included in the present invention.

The term "nitrogen protecting group" refers a chemical group suitable for protecting (that is adding and later removing) a nitrogen atom. Nitrogen protecting groups are known in the art and include, for example, acyl groups, ester groups, aralkyl groups, and the like. Suitable nitrogen protecting groups, as well as methods for protecting and deprotecting nitrogen are delineated in T. W. Greene and P. G. M. Wuts, Protective Groups in Organic Synthesis, 2d. Ed., John Wiley and Sons (1991); and subsequent editions thereof.

The term "oxygen (or sulfur) protecting group" refers to refers to a chemical group suitable for protecting (that is adding and later removing) an oxygen (or sulfur) atom. Oxygen (or sulfur) protecting groups are known in the art and include, for example, acyl groups, t-Butyl, benzyl groups, and the like. Suitable oxygen (or sulfur) protecting groups, as well as methods for protecting and deprotecting oxygen (or sulfur) are delineated in T. W. Greene and P. G. M. Wuts, Protective Groups in Organic Synthesis, 2d. Ed., John Wiley and Sons (1991); and subsequent editions thereof.

As used herein, the compounds of this invention, including the compounds of formulae described herein, are defined to include pharmaceutically acceptable derivatives or prodrugs thereof. A "pharmaceutically acceptable derivative or prodrug" means any pharmaceutically acceptable salt, ester, salt of an ester, or other derivative of a compound of this invention which, upon administration to a recipient, is capable of providing (directly or indirectly) a compound of this invention. Particularly favored derivatives and prodrugs are those that increase the bioavailability of the compounds of this invention when such compounds are administered to a mammal (e.g., by allowing an orally administered compound to be more readily absorbed into the blood) or which enhance delivery of the parent compound to a biological compartment (e.g., the brain or lymphatic system) relative to the parent species. Preferred prodrugs include derivatives where a group which enhances aqueous solubility or active transport through the gut membrane is appended to the structure of formulae described herein.

The compounds of this invention may be modified by appending appropriate functionalities to enhance selective biological properties. Such modifications are known in the art and include those which increase biological penetration into a given biological compartment (e.g., blood, lymphatic system, central nervous system), increase oral availability, increase solubility to allow administration by injection, alter metabolism and alter rate of excretion.

Pharmaceutically acceptable salts of the compounds of this invention include those derived from pharmaceutically acceptable inorganic and organic acids and bases. Examples of suitable acid salts include acetate, adipate, benzoate, benzenesulfonate, butyrate, citrate, digluconate, dodecylsulfate, forinate, fumarate, glycolate, hemisulfate, heptanoate, hexanoate, hydrochloride, hydrobromide, hydroiodide, lactate, maleate, malonate, methanesulfonate, 2-naphthalenesulfonate, nicotinate, nitrate, palmoate, phosphate, picrate, pivalate, propionate, salicylate, succinate, sulfate, tartrate, tosylate and undecanoate. Salts derived from appropriate bases include alkali metal (e.g., sodium), alkaline earth metal (e.g., magnesium), ammonium and N-(alkyl)$_4^+$ salts. This invention also envisions the quaternization of any basic nitrogen-containing groups of the compounds disclosed herein. Water or oil-soluble or dispersible products may be obtained by such quaternization.

The compounds of the formulae described herein can, for example, be administered by injection, intravenously, intraarterially, subdermally, intraperitoneally, intramuscularly, or subcutaneously; or orally, buccally, nasally, transmucosally, topically, in an ophthalmic preparation, or by inhalation, with a dosage ranging from about 0.001 to about 100 mg/kg of body weight, preferably dosages between 10 mg and 1000 mg/dose, every 4 to 120 hours, or according to the requirements of the particular drug. The methods herein contemplate administration of an effective amount of compound or compound composition to achieve the desired or stated effect. Typically, the pharmaceutical compositions of this invention will be administered from about 1 to about 6 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Alternatively, such preparations contain from about 20% to about 80% active compound.

Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained. Patients may, however, require intermittent treatment on a long-term basis upon any recurrence of disease symptoms. Pharmaceutical compositions of this invention comprise a compound of the formulae described herein or a pharmaceutically acceptable salt thereof; an additional agent including for example, morphine or codeine; and any pharmaceutically acceptable carrier, adjuvant or vehicle. Alternate compositions of this invention comprise a compound of the formulae described herein or a pharmaceutically acceptable salt thereof; and a pharmaceutically acceptable carrier, adjuvant or vehicle. The compositions delineated herein include the compounds of the formulae delineated herein, as well as additional therapeutic agents if present, in amounts effective for achieving a modulation of disease or disease symptoms, including MOR mediated disorders or symptoms thereof.

The term "pharmaceutically acceptable carrier or adjuvant" refers to a carrier or adjuvant that may be administered to a patient, together with a compound of this invention, and which does not destroy the pharmacological activity thereof and is nontoxic when administered in doses sufficient to deliver a therapeutic amount of the compound.

Pharmaceutically acceptable carriers, adjuvants and vehicles that may be used in the pharmaceutical compositions of this invention include, but are not limited to, ion exchangers, alumina, aluminum stearate, lecithin, self-emulsifying drug delivery systems (SEDDS) such as d-α-tocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β-, and γ-cyclodextrin, may also be advantageously used to enhance delivery of compounds of the formulae described herein.

The pharmaceutical compositions of this invention may be administered orally, parenterally, by inhalation spray, topically, rectally, nasally, buccally, vaginally or via an implanted reservoir, preferably by oral administration or administration by injection. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

The pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, or carboxymethyl cellulose or similar dispersing agents which are commonly used in the formulation of pharmaceutically acceptable dosage forms such as emulsions and or suspensions. Other commonly used surfactants such as Tweens or Spans and/or other similar emulsifying agents or bioavailability enhancers which are commonly used in the manufacture of pharmaceutically acceptable solid, liquid, or other dosage forms may also be used for the purposes of formulation.

The pharmaceutical compositions of this invention may be orally administered in any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions and/or emulsions are administered orally, the active ingredient may be suspended or dissolved in an oily phase is combined with emulsifying and/or suspending agents. If desired, certain sweetening and/or flavoring and/or coloring agents may be added.

The pharmaceutical compositions of this invention may also be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

Topical administration of the pharmaceutical compositions of this invention is useful when the desired treatment involves areas or organs readily accessible by topical application. For application topically to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax and water. Alternatively, the pharmaceutical composition can be formulated with a suitable lotion or cream containing the active compound suspended or dissolved in a carrier with suitable emulsifying agents. Suitable carriers include, but are not limited to, mineral oil, sorbitan monostearate, polysorbate 60, cetyl esters wax, cetearyl alcohol, 2-octyldodecanol, benzyl alcohol and water. The pharmaceutical compositions of this invention may also be topically applied to the lower intestinal tract by rectal suppository formulation or in a suitable enema formulation. Topically-transdermal patches are also included in this invention.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

When the compositions of this invention comprise a combination of a compound of the formulae described herein and one or more additional therapeutic or prophylactic agents, both the compound and the additional agent should be present at dosage levels of between about 1 to 100%, and more preferably between about 5 to 95% of the dosage normally administered in a monotherapy regimen. The additional agents may be administered separately, as part of a multiple dose regimen, from the compounds of this invention. Alternatively, those agents may be part of a single dosage form, mixed together with the compounds of this invention in a single composition.

The compounds, compositions, and methods of combination therapy delineated herein are useful to treat a variety of MOR mediated diseases and disease symptoms. In particular, the methods of combination therapy herein are effective in treating a disorder associated with pain.

The concept of "treating" or "treatment" refers to activity that prevents, alleviates, or ameliorates any primary phenomena (e.g., initiation, progression, metastasis) or secondary symptoms associated with disorders delineated herein.

The invention will be further described in the following examples. It should be understood that these examples are for illustrative purposes only and are not to be construed as limiting this invention in any manner.

EXAMPLES

Note on Stereochemical Label

All stereochemical labels are given in the C-2→C-8 direction for compounds of the present invention. The order may not match the numbering of the chain from IUPAC nomenclature. However, this labeling procedure was chosen for overall consistency. See examples of compounds 2 and 43 below:

Example 1

Synthesis of N-terminal Monomers

Compound 2

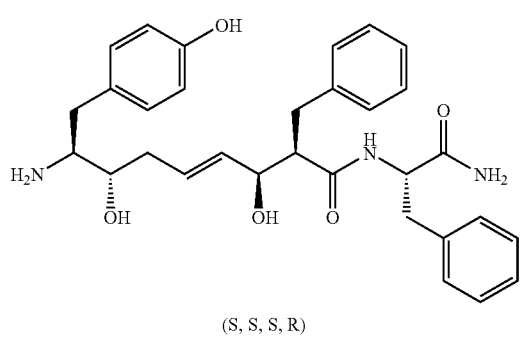

(S, S, S, R)

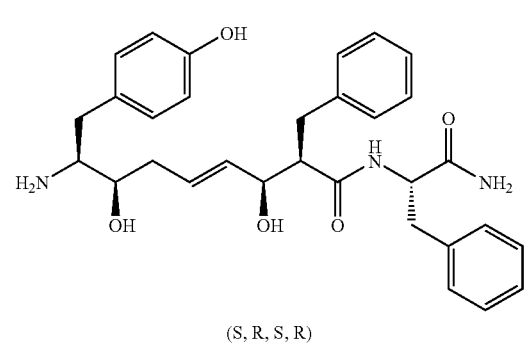

(S, R, S, R)

Compound 43

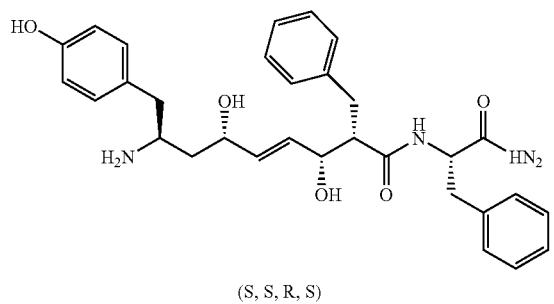

(S, S, R, S)

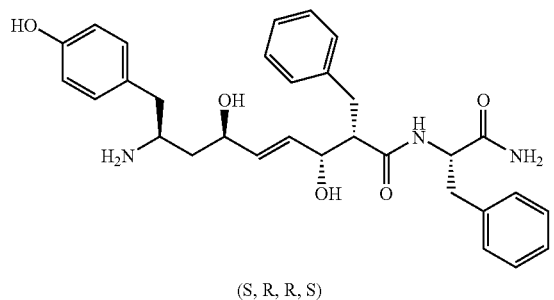

(S, R, R, S)

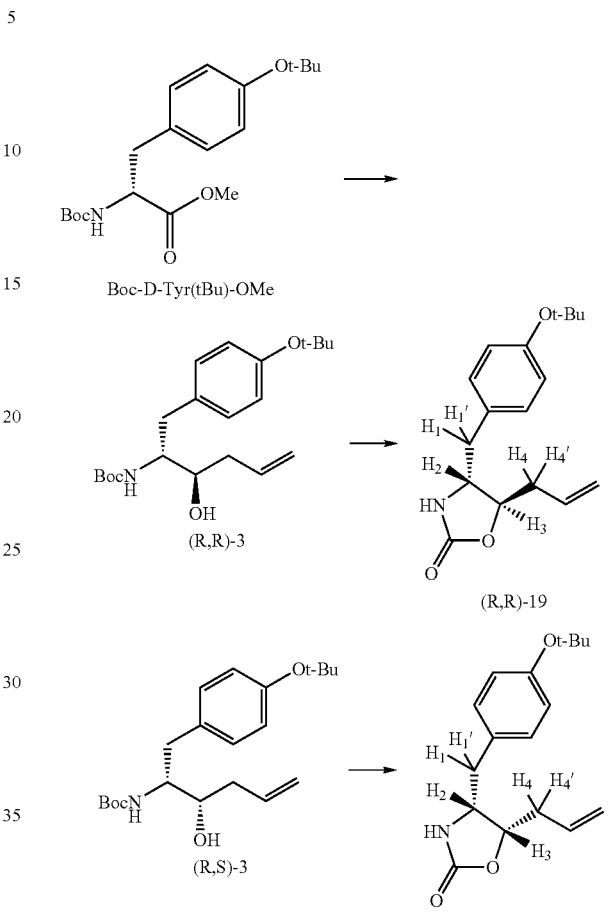

[1-(4-tert-Butoxy-benzyl)-2-hydroxy-pent-4-enyl]-carbamic acid tert-butyl ester (3): All four stereoisomers of 3 were synthesized according to the following procedure: To a stirred solution of Boc-D-Tyr(tBu)-OMe (2.2 g, 6.3 mmole) in toluene/THF (1:1, 20 mL) at −78° C. under $N_2$ was added DIBAL-H (1.5 M in toluene, 10.4 mL, 15.7 mmole) dropwise over 30 minutes. The reaction was stirred for 30 minutes, then quenched by the slow addition of MeOH (1.3 mL, 31.5 mmole) and warmed to room temperature. Rochelle's salt (9 g, 31.5 mmole) in water (50 mL) was added, and the mixture was stirred for 1 hour, then filtered and extracted with ether (50 mL). The ether extract was dried over $MgSO_4$, filtered, and concentrated under vacuum to give Boc-D-Tyr(tBu)-H.

Without further purification, the aldehyde was placed under $N_2$, dissolved in THF (13 mL), cooled to −78° C., and treated with allyl magnesium bromide (1M in $Et_2O$, 19 mL, 19 mmole). The reaction was stirred for 2 hours at 0° C., then quenched with 1N HCl (aq) and extracted with $Et_2O$ (50 mL). The $Et_2O$ extract was washed with sat. $NaHCO_3$ (aq) and brine, dried over $MgSO_4$, filtered, and concentrated under vacuum. Crude NMR showed a 1:1 ratio of diastereomers.

The diastereomers were separated by flash chromatography (4:1 hexanes:EtOAc to 2:1 hexanes:EtOAc) to give an upper fraction containing (R,R)-3 in a 4:1 ratio with (R,S)-3 and a lower fraction containing (R,S)-3 in a 4:1 ratio with (R,R)-3. The upper fraction was flashed again (4:1 hexanes:

EtOAc to 2:1 hexanes:EtOAc) to give 610 mg (27%) of (R,R)-3 in good purity as an oil. The lower fraction was recrystallized from $CH_2Cl_2$:hexanes to give 590 mg (26%) of pure (R,S)-3 as a white solid (53% overall yield). The procedure was repeated with Boc-L-Tyr(tBu)-OMe to give (S,S)-3 and (S,R)-3.

(R,R)-3: $^1$H NMR (400 MHz, $CDCl_3$) δ 7.11 (d, J=8.1 Hz, 2H), 6.90 (d, J=8.4 Hz, 2H), 5.80-5.70 (m, 1H), 5.11 (d, J=14.6 Hz, 2H), 4.85 (d, J=9.2 Hz, 1H), 3.73 (q, J=7.8 Hz, 1H), 3.61-3.56 (m, 1H), 2.89-2.79 (m, 2H), 2.24-2.17 (m, 2H), 2.12 (d, J=3.7 Hz, 1H), 1.40 (s, 9H), 1.31 (s, 9H); $^{13}$C NMR (100 MHz, $CDCl_3$) δ 155.8, 153.5, 134.3, 133.1, 129.5, 124.1, 118.4, 79.3, 78.2, 70.3, 55.2, 39.4, 38.2, 28.9, 28.5; HRMS (ES+) Calcd for $[C_{21}H_{33}NO_4Na]^+$ 386.2307. Found 386.2307.

(R,S)-3: $^1$H NMR (400 MHz, $CDCl_3$) δ 7.09 (d, J=8.4 Hz, 2H), 6.91 (d, J=8.4 Hz, 2H), 5.90-5.80 (m, 1H), 5.19-5.15 (m, 2H), 4.57 (d, J=7.7 Hz, 1H), 3.80 (br s, 1H), 3.71 (br s, 1H), 2.90 (dd, J=4.8, 14.3 Hz, 1H), 2.74 (br t, J=9.2 Hz, 1H), 2.60 (br s, 1H), 2.37-2.34 (br m, 1H), 2.24 (ddd, J=8.1, 8.1, 13.9 Hz, 1H), 1.35 (s, 9H), 1.32 (s, 9H); $^{13}$C NMR (100 MHz, $CDCl_3$) δ 155.9, 153.7, 134.6, 132.8, 129.6, 124.1, 118.2, 79.5, 78.2, 72.7, 55.9, 38.4, 34.7, 28.9, 28.3; HRMS (ES+) Calcd for $[C_{21}H_{33}NO_4Na]^+$ 386.2307. Found 386.2295.

To determine the relative configuration of the monomers, compounds 3 were cyclized to compounds 19. (Kreye, P. and Kihlberg, J. Tetrahedron Lett. 1999, 40, 6113-6116.) Thus, (R,R)-3 (10 mg, 0.028 mmol) was dissolved in THF (600 μL) and treated with KHMDS (0.5 M in toluene, 61 μL, 0.030 mmol). The reaction was stirred for 15 minutes, then diluted with $Et_2O$, washed with 1N HCl (aq), water, sat. $NaHCO_3$ (aq), and brine, dried over $MgSO_4$, filtered, and concentrated under vacuum. The product was isolated by flash chromatography (4:1 hexanes:EtOAc to 1:1 hexanes:EtOAc) to give (R,R)-19 in good yield. The procedure was repeated with (R,S)-3 to give (R,S)-19.

The relative configurations of compounds 19 were determined by NOE experiments. First, $^1$H and COSY spectra were obtained in $CD_3OD$ (gave the best dispersion of the peaks), and the peaks were assigned. Then $H_2$ and $H_3$ were irradiated, and the NOEs were measured for the other protons. (R,R)-19 had a weaker NOE between $H_2$ and $H_3$ and stronger NOEs between $H_2$ and $H_4$ and between $H_3$ and $H_1$ than did (R,S)-19 (Table 2). Consequently, (R,R)-19 was assigned as the trans isomer and (R,S)-19 as the cis isomer.

(R,R)-19: $^1$H NMR (500 MHz, $CD_3OD$) δ 7.15 (d, J=8.3 Hz, 2H), 6.96 (d, J=8.8 Hz, 2H), 5.69-5.61 (m, 1H), 5.08-5.05 (m, 2H), 4.36 (dd, J=5.4, 10.7 Hz, $H_3$), 3.76 (dd, J=6.3, 11.7 Hz, $H_2$), 2.87 (dd, J=6.3, 13.7 Hz, $H_1$), 2.77 (dd, J=7.3, 13.7 Hz, $H_{1'}$), 2.28-2.20 (m, $H_4$, $H_{4'}$), 1.32 (s, 9H); HRMS (ES+) Calcd for $[C_{17}H_{24}NO_3]^+$ 290.1756. Found.

(R,S)-19: $^1$H NMR (500 MHz, $CD_3OD$) δ 7.15 (d, J=8.3 Hz, 2H), 6.96 (d, J=8.3 Hz, 2H), 5.92-5.84 (m, 1H), 5.20 (d, J=17.6 Hz, 1H), 5.14 (d, J=10.3 Hz, 1H), 4.74 (ddd, J=4.4, 7.3, 8.8 Hz, $H_3$), 4.14 (ddd, J=4.4, 7.8, 10.3 Hz, $H_2$), 2.92 (dd, J=4.4, 14.2 Hz, $H_1$), 2.68 (dd, J=10.3, 13.7 Hz, $H_{1'}$), 2.59 (ddd, J=7.3, 7.3, 16.1 Hz, $H_4$), 2.50 (ddd, J=6.8, 6.8, 14.7 Hz, $H_{4'}$), 1.33 (s, 9H); HRMS (ES+) Calcd for $[C_{17}H_{24}NO_3]^+$ 290.1756. Found.

TABLE 2

NOE measurements for (R,R)-19 and (R,S)-19.[a]

| Proton irradiated | Proton NOE | | | | | | | | | |
|---|---|---|---|---|---|---|---|---|---|---|
| | (R,R)-19: | | | | | (R,S)-19: | | | | |
| | $H_2$ | $H_3$ | $H_1$ | $H_{1'}$ | $H_4$ | $H_2$ | $H_3$ | $H_1$ | $H_{1'}$ | $H_4$ | $H_{4'}$ |
| $H_2$ | | 0.3% | | 3.8% | | | 10.5% | | | 0.3% | 0.5% |
| $H_3$ | 2.6% | | 2.1% | 2.9% | | 9.6% | | 0% | 0% | | |

[a] 500 MHz NMR measured in $CD_3OD$.

Example 2

Synthesis of C-terminal Monomers

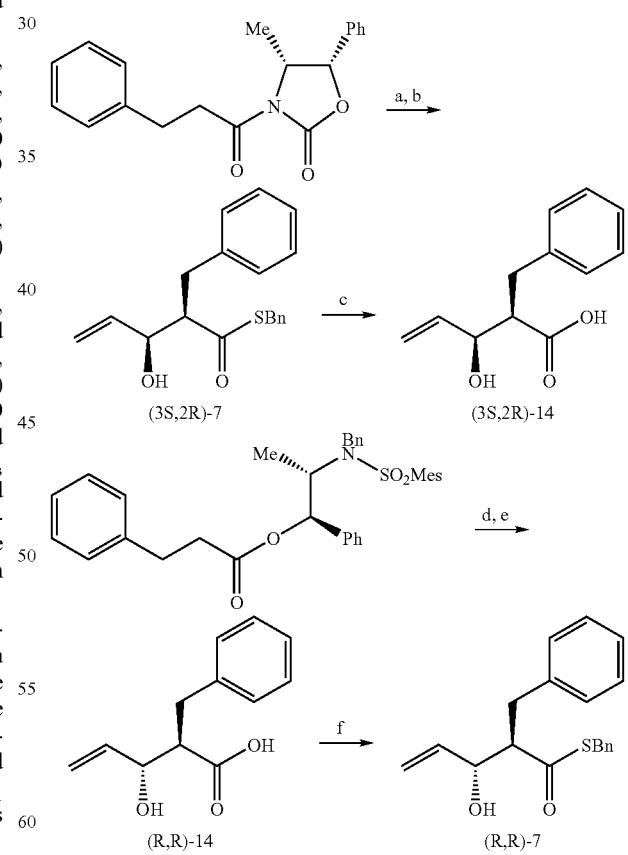

(a) $Bu_2BOTf$, $NEt_3$, $CH_2Cl_2$, acrolein, 50%; (b) BnSH, BuLi, $AlMe_3$, THF, 79%; (c) LiOH, $H_2O_2$, THF, $H_2O$, 94%; (d) $Cy_2BOTf$, $NEt_3$, $CH_2Cl_2$, acrolein, 70%; (e) NaOH, MeOH, $H_2O$, THF; (f) BnSH, DCC, DMAP, $CH_2Cl_2$, 99%.

2-Benzyl-3-hydroxy-pent-4-enoic acid (14): (3S,2R)-14 and (3R,2S)-14 were synthesized from (3S,2R)-7 and (3R, 2S)-7 by hydrolysis of the thioester. (3R,2R)-14 and (3S,2S)-14 were synthesized using a previously reported chiral auxiliary-directed Masamune anti-aldol reaction. (Gierasch, T. M.; Chytil, M.; Didiuk, M. T.; Park, J. Y.; Urban, J. J.; Nolan, S. P.; Verdine, G. L. *Organic Lett.* 2000, 2, 3999-4002; Abiko, A.; Liu, J.-f.; Masamune, S. *J. Am. Chem. Soc.* 1997, 119, 2586-2587.)

(3S,2R)-14: $^1$H NMR (400 MHz, CDCl$_3$) δ 7.30-7.18 (m, 5H), 5.94 (ddd, J=6.12, 10.6, 16.8 Hz, 1H), 5.37 (d, J=17.2 Hz, 1H), 5.29 (d, J=10.6 Hz, 1H), 4.39 (t, J=5.5 Hz, 1H), 3.03 (dd, J=7.3, 11.7 Hz, 1H), 2.96-2.87 (m, 2H); $^{13}$C NMR (100 MHz, CDCl$_3$) δ 178.3, 138.6, 136.5, 128.8, 128.4, 126.5, 117.7, 72.8, 52.6, 33.0; HRMS (CI+) Calcd for [C$_{12}$H$_{14}$O$_3$NH$_4$]$^+$ 224.1287. Found 224.1286.

(3S,2S)-14: $^1$H NMR (400 MHz, CDCl$_3$) δ 7.31-7.21 (m, 5H), 5.90 (ddd, J=5.9, 10.6, 16.5 hz, 1H), 5.34 (d, J=16.8 Hz, 1H), 5.24 (d, J=10.3 Hz, 1H), 4.22 (t, J=5.5 Hz, 1H), 3.00 (d, J=7.7 Hz, 2H), 2.83 (ddd, J=5.5, 7.3, 7.3 Hz, 1H); $^{13}$C NMR (100 MHz, CDCl$_3$) δ 178.6, 138.0, 137.9, 128.9, 128.5, 126.6, 116.9, 72.3, 52.6, 35.0; HRMS (ES−) Calcd for [C$_{12}$H$_{15}$O$_3$]$^−$ 205.0865. Found 205.0856.

2-Benzyl-3-hydroxy-pent-4-enethioic acid S-benzyl ester (7): (3S,2R)-7 and (3R,2S)-7 were synthesized using a previously reported chiral auxiliary-directed Evans syn-aldol reaction. (Gierasch, T. M.; Chytil, M.; Didiuk, M. T.; Park, J. Y.; Urban, J. J.; Nolan, S. P.; Verdine, G. L. *Organic Lett.* 2000, 2, 3999-4002; Evans, D. A.; Gage, J. R.; Leighton, J. L. *J. Am. Chem. Soc.* 1992, 114, 9434-9453.) (3R,2R)-7 and (3S,2S)-7 were prepared by thioesterification of (3R,2R)-14 and (3S,2S)-14.

(3S,2R)-7: $^1$H NMR (500 MHz, CDCl$_3$) δ 7.27-7.10 (m, 10H), 5.88 (ddd, J=5.9, 10.3, 17.1 Hz, 1H), 5.34 (d, J=17.1 Hz, 1H), 5.23 (d, J=10.3 Hz, 1H), 4.43-4.40 (m, 1H), 4.08 (d, J=13.7 Hz, 1H), 4.00 (d, J=14.2 Hz, 1H), 3.07-2.97 (m, 3H), 2.34 (d, J=3.9 Hz, 1H); $^{13}$C NMR (100 MHz, CDCl$_3$) δ 201.0, 138.5, 137.04, 136.97, 129.0, 128.7, 128.5, 128.4, 127.2, 126.4, 117.1, 73.1, 61.0, 33.6, 33.2; HRMS (CI+) Calcd for [C$_{19}$H$_{20}$O$_2$SNH$_4$]$^+$ 330.1528. Found 330.1529.

(3R,2R)-7: $^1$H NMR (500 MHz, CDCl$_3$) δ 7.32-7.18 (m, 10H), 5.91 (ddd, J=5.4, 10.7, 17.1 Hz, 1H), 5.36 (d, J=17.1 Hz, 1H), 5.24, (d, J=10.7 Hz, 1H), 4.29-4.28 (m, 1H), 4.15 (d, J=14.2 Hz, 1H), 4.07 (d, J=14.2 Hz, 1H), 3.06-3.00 (m, 3H), 2.72 (d, J=7.3 Hz, 1H); $^{13}$C NMR (100 MHz, CDCl$_3$) δ 201.8, 138.1, 137.9, 136.9, 129.2, 128.7, 128.51, 128.48, 127.2, 126.5, 116.5, 73,0, 60.4, 35.8, 33.2; HRMS (CI+) Calcd for [C$_{19}$H$_{20}$O$_2$SNH$_4$]$^+$ 330.1528. Found 330.1527.

Example 3

Synthesis of Trans and Reduced Olefin Stereodiversified Libraries

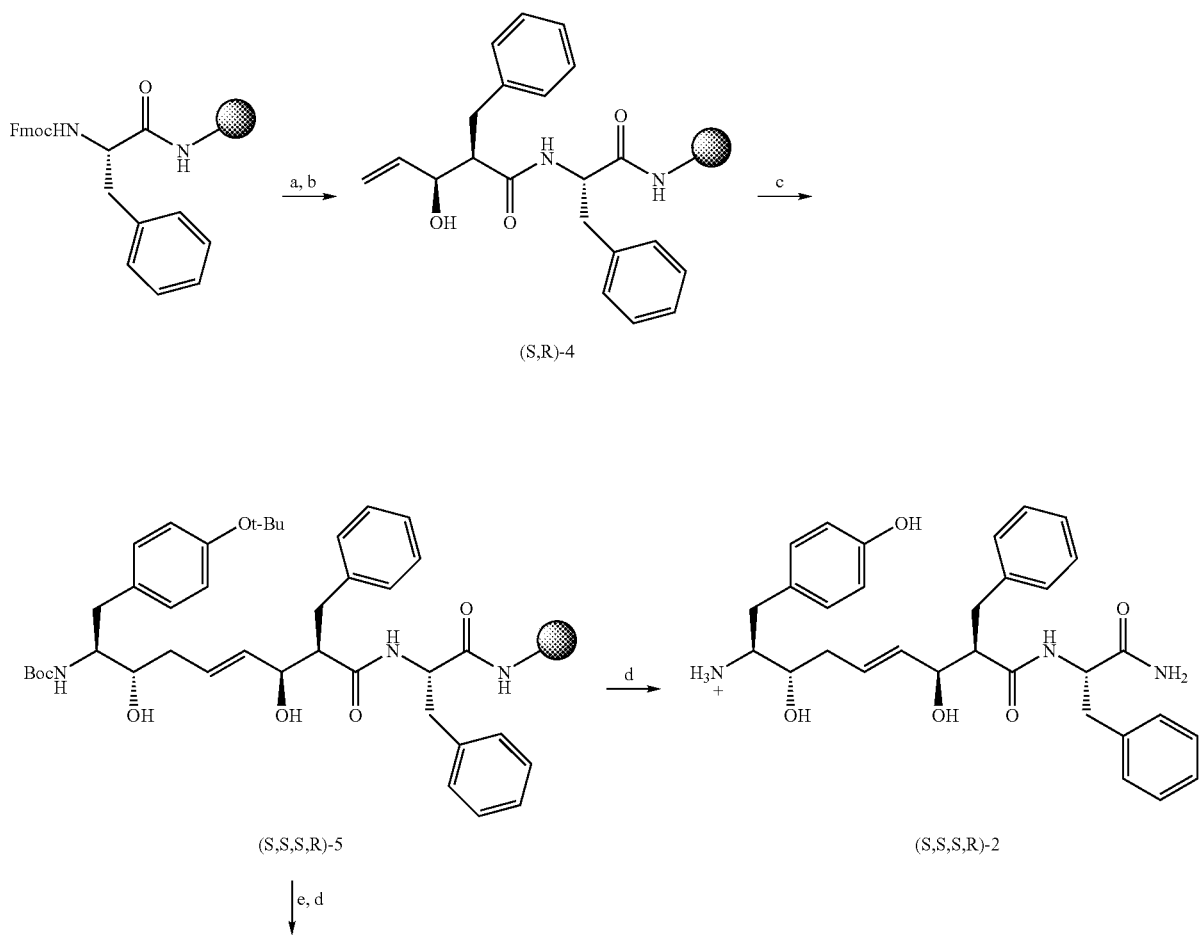

-continued

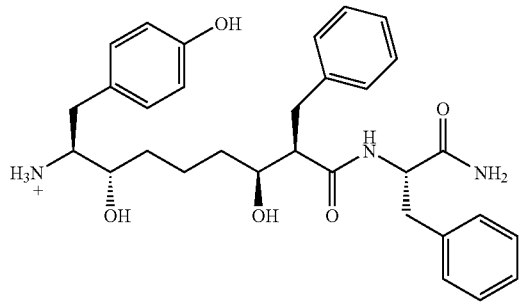

(S,S,S,R)-6

<sup>a</sup>Key: (a) 20% piperidine, NMP; (b) (3S,2R)-12, HBTU, HOBT, DIPEA, NMP, (c) (S,S)-3, Cl₂(PCy₃)(IMesH₂)RuCHPh, CH₂Cl₂, 25° C., 25%; (d) 95% TFA; (e) TPSH, piperidine, NMP, 100%.

Compounds 4: All four stereoisomers of 4 were synthesized in parallel using standard solid phase peptide synthesis techniques. Rink amide AM resin (0.50 g, 0.63 mmole/g, 0.32 mmole) was added to each of four synthesis vessels and loaded with Fmoc-L-Phe (77.4 mg, 0.20 mmole) with standard HBTU, HOBT, DIPEA, NMP coupling techniques. The remaining sites were capped with Ac₂O, DIPEA, NMP (2:1:15) for 30 minutes. The Fmoc was deprotected with 20% piperidine/NMP for 20 minutes, and one stereoisomer of 14 (82 mg, 0.40 mmole), HBTU (152 mg, 0.40 mmole), HOBT (54 mg, 0.40 mmole), and DIPEA (139 μL, 0.80 mmole) in NMP (4 mL) were added to each vessel. Any unreacted sites were capped with Ac₂O, DIPEA, NMP (2:1:15) for 30 minutes. The beads were washed three times with NMP alternating with iPrOH and three times with CH₂Cl₂ alternating with Et₂O. The beads were dried under high vacuum overnight. An aliquot of beads from each reaction was weighed out, and the products were cleaved from the resin with 95% TFA, 2.5% H₂O, and 2.5% tri-isopropylsilane (TIS) for 1 hour. The loading level for each diastereomer was determined by analytical HPLC based on UV absorbance at 254 nm: (R,S)-4 0.33 mmole/g, (S,R)-4 0.31 mmole/g, (R,R)-4 0.33 mmole/g, and (S,S)-4 0.30 mmole/g.

(E)-8-Amino-2-benzyl-3,7-dihydroxy-9-(4-hydroxy-phenyl)-non-4-enoic acid (1-carbamoyl-2-phenyl-ethyl)-amide (2): 16 stereoisomers of 2 were synthesized in parallel using a solid phase olefin cross metathesis reaction. Optimized procedure: To a mixture of (S,S)-3 (36 mg, 99 μmole), (R,S)-4 (30 mg, 9.9 mmole), and Cl₂(PCy₃)(IMesH₂)Ru=CHPh (8.4 mg, 9.9 μmole) under Ar was added CH₂Cl₂. The reaction was shaken overnight to produce (SSR, S)-5. The beads were collected by filtration on a frit, then washed with CH₂Cl₂, three times with NMP alternating with MeOH, and three times with CH₂Cl₂ alternating with Et₂O and dried under high vacuum.

The product was deprotected and cleaved from the resin with 95% TFA, 2.5% H₂O, and 2.5% TIS for 1 hour. The cleavage cocktail was blown off with N₂, and the residue was dissolved in 1:1 MeCN:H₂O (300 μL). The product was isolated by preparative HPLC (25 cm semi-prep C18 column, 30% to 50% MeCN:H₂O with 0.1% TFA over 10 minutes, 2 mL/min, retention time=12.74 minutes). The solvent was removed by lyophilization, and the product was characterized by NMR and MS.

The product was redissolved in 4 mL MeCN:H₂O. UV absorbance measurements using analytical HPLC (10 cm C8 analytical column, 5% to 75% MeCN:H₂O with 0.1% formic acid over 14 minutes, 2 mL/min, absorbance at 276 nm≈4.0× 10⁴ mAu·s/μmole, based on Tyr-OtBu) revealed 3.2 μmole of (S,S,R,S)-2 (32%) in 96% purity.

This method for the synthesis of 2 yielded 24-38% of the desired product for the five stereoisomers attempted. The HPLC traces of the crude products look very clean, with little remaining starting material. Other stereoisomers were synthesized by similar methods that gave comparable yields. Up to 16 compounds were synthesized in parallel with this method.

(R,R,R,S)-2: ¹H NMR (500 MHz, CD₃OD) δ 8.00 (d, J=8.3 Hz, 1H, slowly exchanges), 7.20-6.98 (m, 12H), 6.76 (d, J=8.3 Hz, 2H), 5.65 (dd, J=6.4, 15.6 Hz, 1H), 5.57 (ddd, J=6.6, 6.6, 15.1 Hz, 1H), 4.52 (ddd, J=5.4, 8.8, 13.7 Hz, 1H), 4.17 (t, J=6.6 Hz, 1H), 3.64 (ddd, J=4.4, 6.3, 6.3 Hz, 1H), 3.3 (1H, obscured by solvent peak), 3.02-2.94 (m, 2H), 2.81-2.67 (m, 5H), 2.30 (t, J=6.6 Hz, 2H); HRMS (ES+) Calcd for [C₃₁H₃₈N₃O₅]⁺ 532.2811. Found 532.2826.

(S,S,R,S)-2: ¹H NMR (500 MHz, CD₃OD) δ 7.19-7.00 (m, 12H), 6.72 (d, J=8.8 Hz, 2H), 5.65 (dd, J=6.8, 15.6 Hz, 1H), 5.53 (ddd, J=6.8, 6.8, 15.6 Hz, 1H), 4.51 (dd, J=4.9, 9.3 Hz, 1H), 4.15 (t, J=6.1 Hz, 1H), 3.63 (q, J=5.5 Hz, 1H), 3.3 (1H, obscured by solvent peak), 3.03 (dd, J=4.9, 14.2 Hz, 1H), 2.95 (dd, J=7.3, 13.7 Hz, 1H), 2.78-2.67 (m, 5H), 2.34-2.26 (m, 2H); HRMS (ES+) Calcd for [C₃₁H₃₈N₃O₅]⁺ 532.2811. Found 532.2789.

(S,R,R,S)-2: ¹H NMR (500 MHz, CD₃OD) δ 7.21-6.98 (m, 12H), 6.76 (d, J=8.3 Hz, 2H), 5.70-5.60 (m, 2H), 4.47 (dd, J=5.4, 8.3 Hz, 1H), 4.17 (t, J=6.1 Hz, 1H), 3.84 (ddd, J=2.9, 5.9, 8.3 Hz, 1H), 3.44 (ddd, J=2.9, 4.9, 9.8 Hz, 1H), 3.01-2.94 (m, 2H), 2.83-2.65 (m, 5H), 2.34-2.26 (m, 2H); HRMS (ES+) Calcd for [C₃₁H₃₈N₃O₅]⁺ 532.2811. Found 532.2796.

(R,S,R,S)-2: ¹H NMR (500 MHz, CD₃OD) δ 8.05 (d, J=7.8 Hz, 1H, slowly exchanges), 7.19-6.98 (m, 12H), 6.78 (d, J=8.3 Hz, 2H), 5.74-5.65 (m, 2H), 4.52 (dd, J=5.4, 9.3 Hz, 1H), 4.22 (t, J=5.9 Hz, 1H), 3.81 (ddd, J=3.4, 4.9, 8.3 Hz, 1H), 3.43 (ddd, J=3.4, 5.4, 9.8 Hz, 1H), 3.02, 2.97 (m, 2H), 2.82-2.67 (m, 5H), 2.34 (ddd, J=5.4, 5.4, 14.2 Hz, 1H), 2.25 (ddd, J=6.3, 8.3, 14.6 Hz, 1H); HRMS (ES+) Calcd for [C₃₁H₃₈N₃O₅]⁺ 532.2811. Found 532.2804.

(R,R,S,R)-2: ¹H NMR (500 MHz, CD₃OD) δ 7.89 (d, J=7.3 Hz, 1H, slowly exchanges), 7.23-7.08 (m, 12H), 6.75 (d, J=8.3 Hz, 2H), 5.57 (ddd, J=7.3, 7.3, 15.1 Hz, 1H), 5.44 (dd, J=6.8, 15.6 Hz, 1H), 4.41 (dd, J=5.4, 8.3 Hz, 1H), 4.10 (t, J=6.6 Hz, 1H), 3.58 (q, J=5.7 Hz, 1H0, 3.28-3.26 (1H, obscured by solvent), 3.03 (dd, J=5.9, 14.2 Hz, 1H), 2.95 (dd, J=7.3, 14.2 Hz, 1H), 2.90-2.72 (m, 4H), 2.70-2.65 (m, 1H), 2.19 (t, J=5.9 Hz, 2H); HRMS (ES+) Calcd for [C$_{31}$H$_{38}$N$_3$O$_5$]$^+$532.2811. Found 532.2834.

(S,S,S,R)-2: $^1$H NMR (500 MHz, CD$_3$OD) δ 7.89 (d, J=7.8 Hz, 1H, slowly exchanges), 7.23-7.08 (m, 12H), 6.77 (d, J=8.3 Hz, 2H), 5.62 (ddd, J=7.3, 7.3, 14.7 Hz, 1H), 5.40 (dd, J=6.3, 15.1 Hz, 1H), 4.45 (ddd, J=5.4, 8.3, 8.3 Hz, 1H), 4.10 (t, J=6.6 Hz, 1H), 3.59 (q, J=5.7 Hz, 1H), 3.25 (q, J=6.5 Hz, 1H), 3.04 (dd, J=5.4, 13.7 Hz, 1H), 2.95-2.90 (m, 2H), 2.84-2.78 (m, 2H), 2.74 (dd, J=7.3, 14.2 Hz, 1H), 2.65 (ddd, J=5.4, 6.8, 11.7 Hz, 1H), 2.21-2.17 (m, 2H); HRMS (ES+) Calcd for [C$_{31}$H$_{38}$N$_3$O$_5$]$^+$532.2811. Found 532.2816.

(S,R,S,R)-2: $^1$H NMR (500 MHz, CD$_3$OD) δ 7.94 (d, J=7.8 Hz, 1H, slowly exchanges), 7.26-7.08 (m, 12H), 6.78 (d, J=8.8 Hz, 2H), 5.64 (ddd, J=6.3, 6.3, 15.6 Hz, 1H), 5.47 (dd, J=6.8, 15.6 Hz, 1H), 4.45 (ddd, J=5.4, 8.3, 8.3 Hz, 1H), 4.14 (t, J=6.6 Hz, 1H), 3.78 (ddd, J=2.9, 6.8, 6.8 Hz, 1H), 3.38 (ddd, J=2.9, 4.9, 9.3 Hz, 1H), 3.05 (dd, J=5.4, 13.7 Hz, 1H), 2.96-2.90 (m, 2H), 2.85-2.80 (m, 2H), 2.74-2.66 (m, 2H), 2.19 (t, J=6.8 Hz, 2H); HRMS (ES+) Calcd for [C$_{31}$H$_{38}$N$_3$O$_5$]$^+$532.2811. Found 532.2828.

(R,S,S,R)-2: $^1$H NMR (500 MHz, CD$_3$OD) δ 7.92 (d, J=7.8 Hz, 1H, slowly exchanges), 7.27-7.07 (m, 12H), 6.77 (d, J=8.3 Hz, 2H), 5.64 (ddd, J=6.8, 6.8, 15.6 Hz, 1H), 5.46 (dd, J=6.8, 15.6 Hz, 1H), 4.45 (ddd, J=5.9, 8.3, 8.3 Hz, 1H), 4.12 (t, J=6.8 Hz, 1H), 3.81 (ddd, J=2.9, 6.3, 7.8 Hz, 1H), 3.41 (ddd, J=2.9, 4.9, 9.8 Hz, 1H), 3.04 (dd, J=5.9, 13.7 Hz, 1H), 2.98-2.93 (m, 2H), 2.86-2.80 (m, 2H), 2.73-2.66 (m, 2H), 2.25-2.14 (m, 2H); HRMS (ES+) Calcd for [C$_{31}$H$_{38}$N$_3$O$_5$]$^+$ 532.2811. Found 532.2790.

(R,R,R,R)-2: $^1$H NMR (500 MHz, CD$_3$OD) δ 8.06 (d, J=7.8 Hz, 1H, slowly exchanges), 7.22-7.05 (m, 12H), 6.76 (d, J=8.8 Hz, 2H), 5.52 (dd, J=7.3, 15.6 Hz, 1H), 5.31 (ddd, J=6.8, 6.8, 15.6 Hz, 1H), 4.48 (ddd, J=4.9, 8.3, 9.8 Hz, 1H), 4.02 (t, J=6.3 Hz, 1H), 3.54 (ddd, J=3.9, 6.3, 6.3 Hz, 1H), 3.28-3.25 (1H, obscured by solvent peak), 3.16 (dd, J=5.4, 14.2 Hz, 1H), 2.96 (dd, J=7.3, 13.7 Hz, 1H), 2.83-2.70 (m, 4H), 2.61 (ddd, J=5.4, 5.4, 10.3 Hz, 1H), 2.22 (t, J=13.2 Hz, 1H); HRMS (ES+) Calcd for [C$_{31}$H$_{38}$N$_3$O$_5$]$^+$532.2811. Found 532.2835.

(S,S,R,R)-2: $^1$H NMR (500 MHz, CD$_3$OD) δ 7.97 (d, J=7.8 Hz, 1H, slowly exchanges), 7.25-7.04 (m, 12H), 6.75 (d, J=8.8 Hz, 2H), 5.55 (dd, J=7.3, 15.6 Hz, 1H), 5.46 (ddd, J=6.8, 6.815.6 Hz, 1H), 4.48 (ddd, J=5.4, 8.3, 9.8 Hz, 1H), 4.04 (t, J=6.3 Hz, 1H), 3.61 (ddd, J=4.4, 6.3, 6.3 Hz, 1H), 3.27 (ddd, J=3.9, 7.3, 7.3, 1H), 3.16 (dd, J=5.4, 14.2 Hz, 1H), 2.94 (dd, J=7.3, 14.2 Hz, 1H), 2.84 (dd, J=9.8, 14.2 Hz, 1H), 2.78-2.69 (m, 3H), 2.55 (ddd, J=5.9, 5.9, 9.8 Hz, 1H), 2.28 (t, J=6.6 Hz, 2H); HRMS (ES+) Calcd for [C$_{31}$H$_{38}$N$_3$O$_5$]$^+$ 532.2811. Found 532.2790.

(S,R,R,R)-2: $^1$H NMR (500 MHz, CD$_3$OD) δ 8.04 (d, J=8.3 Hz, 1H, slowly exchanges), 7.26-7.05 (m, 12H), 6.78 (d, J=8.3 Hz, 2H), 5.57 (dd, J=6.8, 15.1 Hz, 1H), 5.47 (ddd, J=6.8, 6.8, 15.6 Hz, 1H), 4.49 (ddd, J=4.9, 8.3, 9.8 Hz, 1H), 4.06 (t, J=6.3 Hz, 1H), 3.78 (ddd, J=2.9, 5.4, 8.3 Hz, 1H), 3.43 (ddd, J=3.4, 5.4, 9.3 Hz, 1H), 3.16 (dd, J=4.9, 13.7 Hz, 1H), 2.96 (dd, J=5.4, 14.7 Hz, 1H), 2.85-2.80 (m, 2H), 2.76-2.71 (m, 2H), 2.60 (ddd, J=5.4, 5.4, 10.3 Hz, 1H), 2.30 (ddd, J=6.3, 6.3, 13.7 Hz, 1H), 2.22 (t, J=7.3, 7.3, 14.2 Hz, 1H); HRMS (ES+) Calcd for [C$_{31}$H$_{38}$N$_3$O$_5$]$^+$532.2811. Found 532.2803.

(R,S,R,R)-2: $^1$H NMR (500 MHz, CD$_3$OD) δ 7.99 (d, J=7.8 Hz, 1H, slowly exchanges), 7.28-7.05 (m, 12H), 6.76 (d, J=6.3 Hz, 2H), 5.60-5.59 (m, 2H), 4.48 (ddd, J=5.4, 8.3, 9.3 Hz, 1H), 4.09 (t, J=5.9 Hz, 1H), 3.81 (ddd, J=2.9, 5.9, 8.3 Hz, 1H), 3.43 (ddd, J=2.4, 4.9, 9.3 Hz, 1H), 3.15 (dd, J=4.9, 13.7 Hz, 1H), 2.97 (dd, J=4.9, 14.2 Hz, 1H), 2.85 (dd, J=9.3, 13.7 Hz, 1H), 2.80-2.70 (m, 3H), 2.59 (ddd, J=5.9, 5.9, 10.3 Hz, 1H), 2.33 (ddd, J=5.9, 5.9, 14.2 Hz, 1H), 2.28-2.23 (m, 1H); HRMS (ES+) Calcd for [C$_{31}$H$_{38}$N$_3$O$_5$]$^+$532.2811. Found 532.2836.

(R,R,S,S)-2: $^1$H NMR (500 MHz, CD$_3$OD) δ 8.07 (d, J=8.3 Hz, 1H, slowly exchanges), 7.21-6.97 (m, 12H), 6.74 (d, J=8.8 Hz, 2H), 5.68 (ddd, J=6.8, 6.8, 15.6 Hz, 1H), 5.56 (dd, J=7.8, 15.6 Hz, 1H), 4.52 (ddd, J=4.4, 8.8, 8.8 Hz, 1H), 4.09 (t, J=8.1 Hz, 1H), 3.65 (q, J=5.7 Hz, 1H), 3.28-3.26 (1H, obscured by solvent peak), 3.06 (dd, J=4.9, 14.2 Hz, 1H), 2.96 (dd, J=7.3, 14.2 Hz, 1H), 2.78-2.69 (m, 3H), 2.63-2.55 (m, 2H), 2.33 (t, J=13.2 Hz, 2H).

(S,S,S,S)-2: $^1$H NMR (500 MHz, CD$_3$OD) δ 8.09 (d, J=8.3 Hz, 1H, slowly exchanges), 7.16-6.97 (m, 12H), 6.72 (d, J=8.3 Hz, 2H), 5.69 (ddd, J=6.8, 6.8, 15.6 Hz, 1H), 5.55 (dd, J=7.8, 15.6 Hz, 1H), 4.52 (ddd, J=4.9, 8.3, 9.3 Hz, 1H), 4.10 (t, J=7.8 Hz, 1H), 3.65 (q, J=5.7 Hz, 1H), 3.28-3.25 (1H, obscured by solvent peak), 3.05 (dd, J=4.9, 14.2 Hz, 1H), 2.95 (dd, J=7.3, 14.2 Hz, 1H), 2.78-2.56 (m, 5H), 2.33 (t, J=6.8 Hz, 2H).

(S,R,S,S)-2: $^1$H NMR (500 MHz, CD$_3$OD) δ 8.12 (d, J=8.3 Hz, 1H, slowly exchanges), 7.16-6.97 (m, 12H), 6.74 (d, J=8.3 Hz, 2H), 5.75 (ddd, J=6.3, 6.3, 15.6 Hz, 1H), 5.60 (dd, J=7.8, 15.6 Hz, 1H), 4.52 (ddd, J=4.9, 8.3, 9.3 Hz, 1H), 4.12 (t, J=8.1 Hz, 1H), 3.84 (ddd, J=2.4, 5.4, 8.3 Hz, 1H), 3.41 (ddd, J=2.9, 5.4.8.3 Hz, 1H), 3.06 (dd, J=4.9, 14.7 Hz, 1H), 2.98 (dd, J=5.4, 14.7 Hz, 1H), 2.79-2.60 (m, 5H), 2.38 (ddd, J=6.8, 6.8, 13.7 Hz, 1H), 2.31 (ddd, J=7.8, 7.8, 14.2 Hz, 1H).

Figure 2:
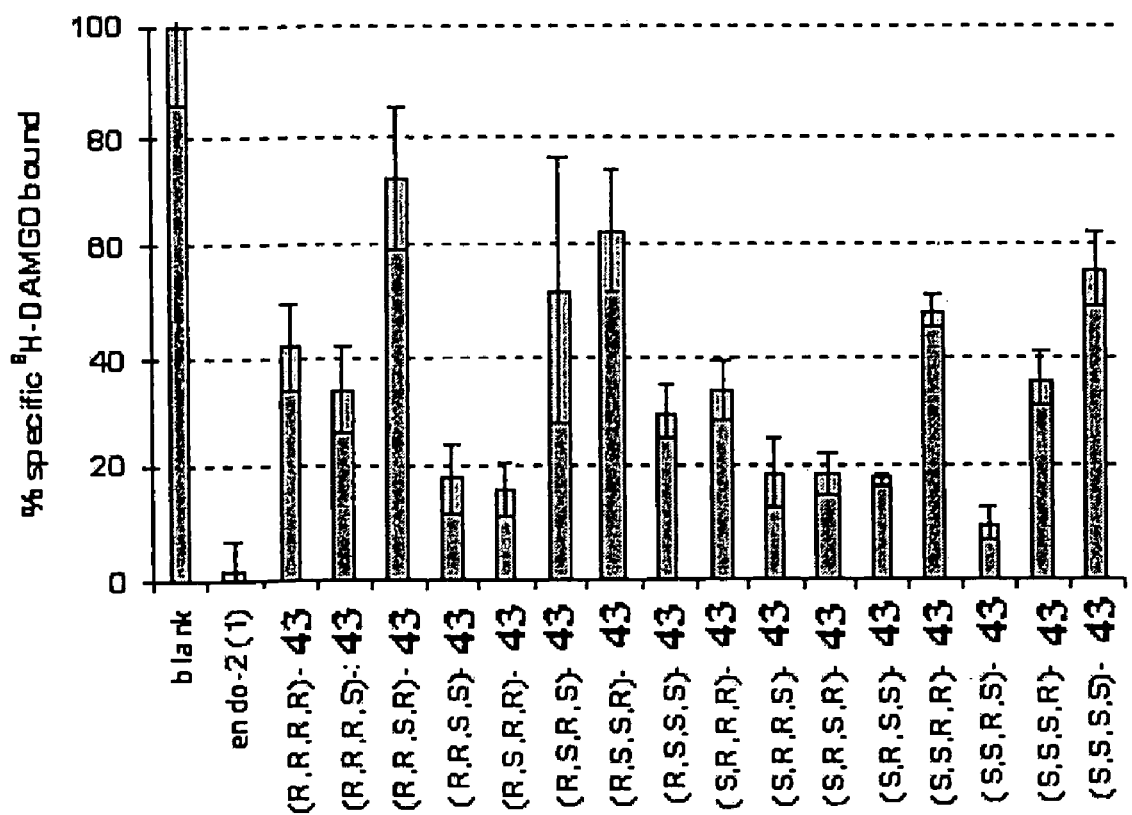
FIG. 2 is a bar graph depicting the binding of Mu Opioid Receptor ligands of compounds 1 and 43.

8-Amino-2-benzyl-3,7-dihydroxy-9-(4-hydroxy-phenyl)-nonanoic acid (1-carbamoyl-2-phenyl-ethyl)-amide (6): Four stereoisomers of 6 were synthesized according to the following procedure: Compounds 5 (30 mg, <0.020 mmole) were preswollen in NMP and treated with triisopropylbenzene sulfonylhydrazide (TPSH) (60 mg, 0.20 mmole) and piperidine (20 μL, 0.20 mmole) in NMP (300 μL) under Ar. The mixtures were shaken at 37° C. for 2 hours, then washed twice with NMP. These steps were repeated 4 times, the last time shaking overnight. The beads were washed twice with NMP alternating with MeOH and twice with CH$_2$Cl$_2$ alternating with Et$_2$O and dried under high vacuum. The products 6 were deprotected and cleaved from the resin, purified, and analyzed the same as for 2. The hydrogenation appeared to be quantitative as no olefins were observed in the product and crude HPLC gave one major peak (FIG. 2). Compounds 6 were obtained in the following yields from 4: (S,S,S,R)-6 4.6 μmole, 24%; (S,S,R,R)-6 4.8 μmoles, 24%; (S,R,R,R)-6 7.5 μmoles, 38%; (S,R,S,R)-6 5.2 μmoles, 25%.

(S,S,S,R)-6: $^1$H NMR (500 MHz, CD$_3$OD) δ 8.06 (d, J=8.3 Hz, 1H), 7.25-7.04 (m, 12H), 6.80 (d, J=8.3 Hz, 2H), 4.51 (ddd, J=4.4, 8.3, 10.7 Hz, 1H), 3.66-3.42 (m, 2H), 3.21-3.10 (m, 3H), 2.94 (dd, J=7.8, 14.2 Hz, 1H), 2.75 (dd, J=6.8, 14.2 Hz, 1H), 2.71-2.61 (m, 2H), 2.41 (ddd, J=3.9, 8.8, 11.7 Hz, 1H), 1.42-1.35 (m, 2H), 1.27-1.24 (m, 1H), 1.14-1.09 (m, 1H), 1.03-0.98 (m, 1H), 0.72-0.68 (m, 1H); HRMS (ES+) Calcd for [C$_{31}$H$_{40}$N$_3$O.]$^+$534.2968. Found 534.2969.

(S,S,R,R)-6: $^1$H NMR (500 MHz, CD$_3$OD) δ 7.94 (d, J=8.3 Hz, 1H), 7.25-7.05 (m, 12H), 6.78 (d, J=8.3 Hz, 2H), 4.55 (ddd, J=4.9, 8.3, 9.8 Hz, 1H), 3.54-3.50 (m, 2H), 3.20 (ddd, J=4.4, 7.3, 7.3 Hz, 1H), 3.15 (dd, J=4.9, 14.2 Hz, 1H), 2.93 (dd, J=7.3, 14.2 Hz, 1H), 2.84-2.79 (m, 3H), 2.74 (dd, J=6.8, 13.7 Hz, 1H), 2.49 (ddd, J=4.4, 7.3, 8.3 Hz, 1H), 1.51-1.21 (m, 6H); HRMS (ES+) Calcd for [C$_{31}$H$_{40}$N$_3$O$_5$]$^+$534.2968. Found 534.2944.

(S,R,R,R)-6: $^1$H NMR (500 MHz, CD$_3$OD) δ 7.96 (d, J=7.8 Hz, 1H), 7.29-7.05 (m, 12 H), 6.78 (d, J=8.3 Hz, 2H), 4.55 (ddd, J=4.9, 8.3, 9.8 Hz, 1H), 3.72 (br s, 1H), 3.59-3.56 (m, 1H), 3.36 (ddd, J=2.9, 5.4, 8.8 Hz, 1H), 3.16 (dd, J=4.9, 14.2 Hz, 1H), 2.90 (dd, J=5.4, 14.2 Hz, 1H), 2.85-2.81 (m, 3H), 2.70 (dd, J=9.8, 14.6 Hz, 1H), 2.51 (ddd, J=4.4, 7.3, 7.3 Hz, 1H), 1.45-1.32 (m, 6H); HRMS (ES+) Calcd for [C$_{31}$H$_{40}$N$_3$O$_5$]$^+$534.2968. Found 534.2967.

(S,R,S,R)-6: $^1$H NMR (500 MHz, CD$_3$OD) δ 8.08 (d, J=8.3 Hz, 1H), 7.27-7.07 (m, 12H), 6.79 (d, J=8.3 Hz, 2H), 4.53 (ddd, J=4.4, 8.3, 10.7 Hz, 1H), 3.70-3.67 (m, 1H), 3.49 (t, J=8.3 Hz, 1H), 3.34 (ddd, J=2.9, 4.9, 9.3 Hz, 1H), 3.20-3.13 (m, 2H), 2.92 (dd, J=4.9, 14.7 Hz, 1H), 2.74-2.64 (m, 3H), 2.43 (ddd, J=3.9, 8.8, 11.7 Hz, 1H), 1.57-1.52 (m, 1H), 1.42 (ddd, J=4.4, 8.3, 11.7 Hz, 1H), 1.25-1.21 (m, 1H), 1.05-1.00 (m, 1H), 0.79-0.74 (m, 1H); HRMS (ES+) Calcd for [C$_{31}$H$_{40}$N$_3$O$_5$]$^+$534.2968. Found 534.2968.

Example 4

Synthesis of cis Olefin Stereodiversified Libraries

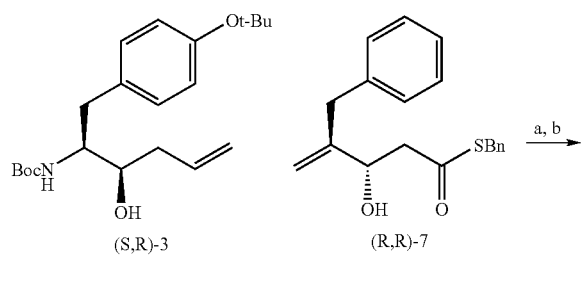

(S,R)-3     (R,R)-7

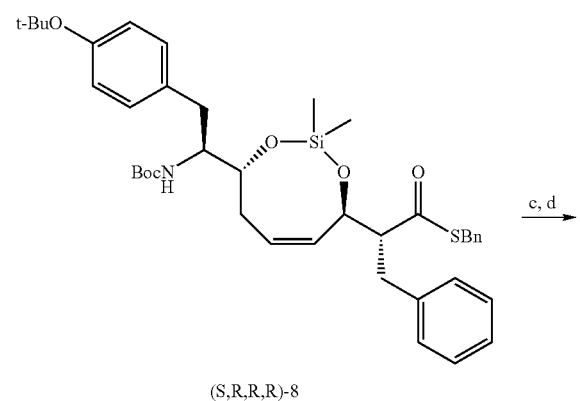

(S,R,R,R)-8

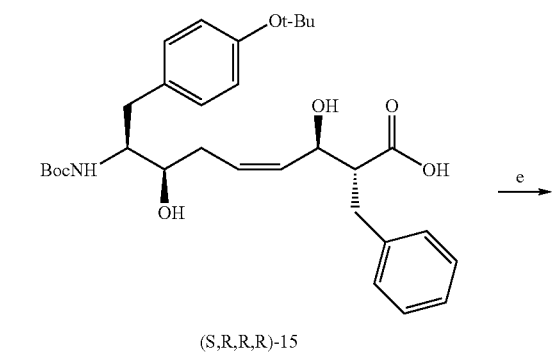

(S,R,R,R)-15

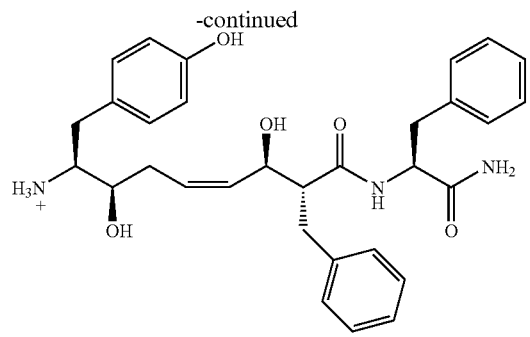

(S,R,R,R)-9

(a) SiMe$_2$Cl$_2$, pyridine, 60%; (b) Cl$_2$(PCy$_3$)(IMesH$_2$)RuCHPh, toluene, 95° C., 89%; (c) HF, pyridine, THF, 0° C., 85%; (d) LiOH, H$_2$O$_2$, THF, H$_2$O, 100%, (e) SPPS, 66%.

2-{8-[1-tert-Butoxycarbonylamino-2-(4-tert-butoxy-phenyl)-ethyl]-2,2-dimethyl-7,8-dihydro-4H-[1,3,2]dioxasilocin-4-yl}-3-phenyl-thiopropionic acid S-benzyl ester (8): Four combinations of monomers 3 and 7 were tethered in parallel with a silyl linker as previously reported and isolated by flash chromatography (16:1 hexanes:EtOAc to 4:1 hexanes:EtOAc) in the following yields: (S,S,S,R) 41%, (S,S,R,R) 32%, (S,R,R,R) 60%, (S,R,S,R) 63%. The silyl tethered products were subjected in parallel to RCM conditions (as previously reported) with 10% Cl$_2$(PCy$_3$)(IMesH$_2$)Ru=CHPh at 95° C. in toluene under Ar for 1 hour and concentrated under vacuum. Compounds 8 were isolated by flash chromatography (8:1 hexanes:EtOAc to 4:1 hexanes:EtOAc) in the following yields: (S,S,S,R)-8 93%, (S,S,R,R)-8 90%, (S,R,R,R)-8 89%, (S,R,S,R)-8 89%.

(S,S,S,R)-8: $^1$H NMR (500 MHz, CDCl$_3$) δ 7.23-7.02 (m, 12H), 6.90 (d, J=8.3 Hz, 2H), 5.78 (t, J=9.8 Hz, 1H), 5.69 (q, J=9.3 Hz, 1H), 4.89 (d, J=9.8 Hz, 1H), 4.54 (t, J=8.5 Hz, 1H), 4.01 (d, J=14.2 Hz, 1H), 3.96 (d, J=13.7 Hz, 1H), 3.83 (q, J=8.3 Hz, 1H), 3.48 (d, J=9.8 Hz, 1H), 3.13-3.04 (m, 2H), 2.94 (dd, J=9.8, 13.2 Hz, 1H), 2.84 (dd, J=5.9, 13.7 Hz, 1H), 2.65 (dd, J=9.3, 13.2 Hz, 1H), 2.43 (ddd, J=9.8, 9.8, 13.7 Hz, 1H), 2.06 (dd, J=8.3, 14.2 Hz, 1H), 1.46 (s, 9H), 1.32 (s, 9H), 0.16 (s, 3H), −0.07 (s, 3H); MS (ES+) Calcd for [C$_{40}$H$_{54}$NO$_6$SSi]$^+$ 704. Found 704.

(S,S,R,R)-8: $^1$H NMR (500 MHz, CDCl$_3$) δ 7.25-7.06 (m, 12H), 6.90 (d, J=8.3 Hz, 2H), 5.83-5.78 (m, 2H), 4.82 (d, J=9.3 Hz, 1H), 4.57 (dd, J=5.9, 8.8 Hz, 1H), 4.07 (d, J=14.2 Hz, 1H), 3.93 (d, J=13.7 Hz, 1H), 3.86 (br s, 1H), 3.80 (q, J=8.0 Hz, 1H), 3.10 (ddd, J=4.4, 10.3, 10.3 Hz, 1H), 2.84-2.71 (m, 3H), 2.67 (dd, J=9.3, 13.2 Hz, 1H), 2.53 (ddd, J=5.9, 5.9, 8.3 Hz, 1H), 2.37-2.33 (m, 1H), 1.43 (s, 9H), 1.33 (s, 9H), 0.06 (s, 3H), 0.01 (s, 3H).

(S,R,R,R)-8: $^1$H NMR (500 MHz, CDCl$_3$) δ 7.25-7.08 (m, 12H), 6.92 (d, J=8.3 Hz, 1H), 5.87-5.76 (m, 2H), 4.73 (t, J=8.3 Hz, 1H), 4.44 (d, J=9.3 Hz, 1H), 4.07 (d, J=14.2 Hz, 1H), 4.01 (d, J=14.2 Hz, 1H), 3.87-3.85 (m, 1H), 3.65-3.63 (m, 1H), 3.05 (ddd, J=3.9, 10.3, 12.7 Hz, 1H), 2.95 (dd, J=3.9, 14.2 Hz, 1H), 2.87 (dd, J=10.7, 13.7 Hz, 1H), 2.76-2.68 (m, 2H), 2.42-2.34 (m, 2H), 1.35 (s, 9H), 1.33 (s, 9H), 0.06 (s, 3H), 0.05 (s, 3H); MS (ES+) Calcd for [C$_{40}$H$_{54}$NO$_6$SSi]$^+$704. Found 704.

(S,R,S,R)-8: $^1$H NMR (500 MHz, CDCl$_3$) δ 7.25-7.08 (m 12H), 6.91 (d, J=8.3 Hz, 2H), 5.85-5.76 (m, 2H), 4.63 (dd, J=5.9, 6.8 Hz, 1H), 4.34 (d, J=10.3 Hz, 1H), 4.04 (d, J=13.7 Hz, 1H), 3.97 (d, J=13.7 Hz, 1H), 3.86-3.83 (m, 1H), 3.69-3.66 (m, 1H), 3.14 (dd, J=3.4, 13.2 Hz, 1H), 3.08 (ddd, J=3.9, 7.8, 9.8 Hz, 1H), 3.00-2.93 (m, 2H), 2.76 (dd, J=7.3, 14.2 Hz, 1H), 2.69 (ddd, J=7.8, 7.8, 13.7 Hz, 1H), 2.37-2.32 (m, 1H), 1.37 (s, 9H), 1.33 (s, 9H), 0.22 (s, 3H), 0.17 (s, 3H); MS (ES+) Calcd for $[C_{40}H_{54}NO_6SSi]^+$ 704. Found 704.

(Z)-8-Amino-2-benzyl-3,7-dihydroxy-9-(4-hydroxy-phenyl)-non-4-enoic acid (15): Compounds 8 were silyl deprotected in parallel with HF/pyridine in THF at 0° C. for 30 minutes according to the reported procedure. The products were purified by flash chromatography (4:1 hexanes:EtOAc to 1:1 hexanes:EtOAc) to give the desilylated products in the following yields: (S,S,S,R) 83%, (S,S,R,R) 67%, (S,R,R,R) 85%, (S,R,S,R) 81%. To hydrolyze the thioester to the free acid, these products were dissolved in THF (40 ml/mmole) in parallel, and a 1:1 mixture of 0.2 N LiOH (aq, 4 eq.) and 30% $H_2O_2$ (aq) was added to each. The reactions were stirred at room temperature for 3 hours, then cooled to 0° and quenched with 2N $NaHSO_3$ (aq, 5 mL per ml 30% $H_2O_2$). The reactions were extracted with EtOAc, washed with brine, dried over $MgSO_4$, filtered, and concentrated under vacuum to give clean 15 in the following yields: (S,S,S,R)-15 100%, (S,S,R,R)-15 96%, (S,R,R,R)-15 100%, (S,R,S,R)-15 100%.

(S,S,S,R)-15: $^1$H NMR (500 MHz, $CD_3OD$) δ 7.24-7.13 (m, 7H), 6.88 (d, J=8.8 Hz, 2H), 5.67-5.58 (m, 2H), 4.54 (t, J=8.1 Hz, 1H), 3.72 (ddd, J=2.4, 5.4, 8.8 Hz, 1H), 3.61-3.58 (m, 1H), 3.07 (dd, J=4.4, 13.7 Hz, 1H), 2.88-2.81 (m, 2H), 2.74-2.67 (m, 2H), 2.37 (ddd, J=7.8, 7.8, 15.1 Hz, 1H), 2.19 (ddd, J=4.4, 4.4, 14.6 Hz, 1H), 1.34 (s, 9H), 1.29 (s, 9H); $^{13}$C NMR (100 MHz, $CD_3OD$) δ 176.7, 158.2, 154.7, 140.9, 135.6, 132.7, 130.9, 130.8, 129.9, 129,3, 127.2, 125.1, 80.0, 79.4, 73.1, 68.9, 57.5, 56.3, 38.3, 35.9, 33.4, 29.2, 28.8; HRMS (ES+) Calcd for $[C_{31}H_{44}NO_7]^+$ 542.3118. Found 0.542.3106.

(S,S,R,R)-15: $^1$H NMR (500 MHz, $CD_3OD$) δ 7.24-7.13 (m, 7H), 6.87 (d, J=8.3 Hz, 2H), 6.18 (d, J=10.3 Hz, 1H, slowly exchanges), 5.66 (ddd, J=6.4, 8.8, 10.7 Hz, 1H), 5.52 (dd, J=9.8, 10.7 Hz, 1H), 4.53 (t, J=9.0 Hz, 1H), 3.76-3.72° (m, 1H), 3.61 (ddd, J=1.5, 6.6, 6.6 Hz, 1H), 2.82-2.60 (m, 5H), 2.41 (ddd, J=7.8, 7.8, 14.2 Hz, 1H), 2.22 (ddd, J=6.6, 6.6, 14.2 Hz, 1H), 1.36 (s, 9H), 1.28 (s, 9H); $^{13}$C NMR (100 MHz, $CD_3OD$) δ 177.4, 158.5, 154.7, 140.6, 135.5, 133.6 130.9, 130.5, 129.9, 129.4, 127.3, 125.2, 80.3, 79.4, 72.9, 69.4, 56.4, 56.2, 38.8, 36.0, 33.8, 29.2, 28.8; HRMS (ES+) Calcd for $[C_{31}H_{44}NO_7]^+$ 542.3118. Found 542.3104.

(S,R,R,R)-15: $^1$H NMR (500 MHz, $CD_3OD$) δ 7.24-7.12 (m, 7H), 6.87 (d, J=8.3 Hz, 1H), 6.50 (d, J=9.3 Hz, 1H, slowly exchanges), 5.78 (ddd, J=7.3, 7.3, 10.7 Hz, 1H), 5.59 (dd, J=9.8, 10.7 Hz, 1H), 4.58 (t, J=8.8 Hz, 1H), 3.66 (ddd, J=3.4, 7.3, 13.2 Hz, 1H), 3.56-3.52 (m, 1H), 3.03 (dd, J=3.4, 1.3.7 Hz, 1H), 2.80-2.72 (m, 2H), 2.68-2.64 (m, 1H), 2.53 (dd, J=10.7, 14.2 Hz, 1H), 2.44-2.40 (m, 1H), 2.34 (ddd, J=7.8, 7.8, 15.1 Hz, 1H), 1.32 (s, 9H), 1.29 (s, 9H); $^{13}$C NMR (100 MHz, $CD_3OD$) δ 177.4, 158.1, 154.6, 140.6, 135.7, 133.3, 131.2, 130.9, 129.9, 129.3, 127.3, 125.1, 79.9, 79.4, 74.6, 69.4, 58.0, 56.2, 36.8, 36.0, 33.1, 29.2, 28.8; HRMS (ES+) Calcd for $[C_{31}H_{44}NO_7]^+$ 542.3118. Found 542.3116.

(S,R,S,R)-15: $^1$H NMR (500 MHz, $CD_3OD$) δ 7.25-7.12 (m, 7H), 6.88 (d, J=8.8 Hz, 2H), 5.70 (ddd, J=6.3, 8.8, 11.2 Hz, 1H), 5.61 (dd, J=9.3, 10.7 Hz, 1H), 4.58 (t, J=8.5 Hz, 1H), 3.65 (ddd, J=3.4, 6.3, 10.3 Hz, 1H), 3.57 (ddd, J=4.4, 6.3, 8.3 Hz, 1H), 3.10 (dd, J=3.9, 13.7 Hz, 1H), 3.02 (dd, J=3.4, 13.7 Hz, 1H), 2.88 (dd, J=10.3, 13.2 Hz, 1H), 2.74 (ddd, J=3.9, 7.8, 11.2 Hz, 1H), 2.57-2.50 (m, 2H), 2.23-2.17 (m, 1H), 1.31 (s, 9H), 1.29 (s, 9H); $^{13}$C NMR (100 MHz, $CD_3OD$) δ 176.9, 158.0, 154.6, 141.0, 135.8, 132.7, 130.9, 130.4, 129.9, 129.3, 127.2, 125.1, 79.9, 79.4, 74.8, 69.2, 57.9, 56.5, 36.5, 35.8, 33.3, 29.2, 28.8; HRMS (ES+) Calcd for $[C_{31}H_{44}NO_7]^+$ 542.3118. Found 542.3104.

(Z)-8-Amino-2-benzyl-3,7-dihydroxy-9-(4-hydroxy-phenyl)-non-4-enoic acid (1-carbamoyl-2-phenyl-ethyl)-amide (9): Compounds 9 were synthesized in parallel using standard solid phase peptide synthesis techniques. Rink amide AM resin (32 mg, 0.63 mmole/g, 20 μmole) was added to each of four synthesis vessels and loaded with Fmoc-L-Phe with standard HBTU, HOBT, DIPEA, NMP coupling techniques. The Fmoc was deprotected with 20% piperidine/NMP for 20 minutes, and one stereoisomer of 15 (5.5 mg, 10 μmole), HATU (3.9 mg, 10 μmole), and HOAT (1.4 mg, 10 μmole) in NMP (1 mL) were added to each vessel. The reactions were bubbled with $N_2$ for 1 hour, then drained, washed three times with NMP alternating with iPrOH and three times with $CH_2Cl_2$ alternating with $Et_2O$, and dried on high vacuum. The products 9 were deprotected and cleaved from the resin, purified, and analyzed the same as for 2. Compounds 9 were obtained in the following yields: (S,S,S,R)-9 5.0 μmole, 50%; (S,S,R,R)-9 7.0 μmole, 70%; (S,R,R,R)-9 6.6 μmole, 66%; (S,R,S,R)-9 64 μmole, 64%.

(S,S,S,R)-9: $^1$H NMR (500 MHz, $CD_3OD$) δ 8.08 (d, J=7.8 Hz, 1H), 7.28-7.08 (m, 12H), 6.81 (d, J=8.8 Hz, 2H), 5.04 (dd, J=9.8, 11.2 Hz, 1H), 4.85 (ddd, J=7.3, 7.3, 10.7 Hz, 1H), 4.33-4.26 (m, 2H), 3.49 (ddd, J=2.9, 5.4, 8.3 Hz, 1H), 3.19 (dd, J=4.4, 14.2 Hz, 1H), 3.12-3.06 (m, 2H), 2.94 (dd, J=8.3, 14.2 Hz, 1H), 2.79-2.74 (m, 2H), 2.62 (dd, J=10.7, 14.2 Hz, 1H), 2.56 (ddd, J=3.9, 9.3, 11.7 Hz, 1H), 2.22 (ddd, J=7.1, 7.1, 16.1 Hz, 1H), 1.99 (ddd, J=6.1, 6.1, 15.1 Hz, 1H); HRMS (ES+) Calcd for $[C_{31}H_{38}N_3O_5]^+$ 532.2811. Found 532.2787.

(S,S,R,R)-9: $^1$H NMR (500 MHz, $CD_3OD$) δ 7.98 (d, J=7.8 Hz, 1H), 7.22-7.06 (m, 12H), 6.76 (d, J=8.3 Hz, 1H), 5.51 (ddd, J=7.1, 7.1, 11.2 Hz, 1H), 5.44 (dd, J=8.8, 10.7 Hz, 1H), 4.49-4.42 (m, 2H), 3.63-3.60 (m, 1H), 3.23 (ddd, J=3.4, 7.3, 7.3 Hz, 1H), 3.13 (dd, J=4.9, 14.2 Hz, 1H), 2.92 (dd, J=7.8, 14.2 Hz, 1H), 2.84 (dd, J=9.3, 14.2 Hz, 1H), 2.76 (dd, J=7.3, 14.2 Hz, 1H), 2.72-2.68 (m, 2H), 2.55-2.51 (m, 1H), 2.37 (ddd, J=6.8, 6.8, 14.2 Hz, 1H), 2.26 (ddd, J=6.8, 6.8, 14.6 Hz, 1H); HRMS (ES+) Calcd for $[C_{31}H_{38}N_3O_5]^+$ 532.2811. Found 532.2787.

(S,R,R,R)-9: $^1$H NMR (500 MHz, $CD_3OD$) δ 8.01 (d, J=7.8 Hz, 1H), 7.24-7.07 (m, 12H), 6.79 (d, J=8.8 Hz, 2H), 5.63 (ddd, J=7.3, 7.3 10.7 Hz, 1H), 5.55 (dd, J=9.3, 10.7 Hz, 1H), 4.50-4.46 (m, 2H), 3.81-3.77 (m, 1H), 3.41 (ddd, J=2.9, 5.4, 8.8 Hz, 1H), 3.13 (dd, J=5.4, 4.2 Hz, 1H), 2.94-2.85 (m, 2H), 2.76-2.67 (m, 3H), 2.55-2.50 (m, 1H), 2.35-2.29 (m, 2H); HRMS (ES+) Calcd for $[C_{31}H_{38}N_3O_5]^+$ 532.2811. Found 532.2787.

(S,R,S,R)-9: $^1$H NMR (500 MHz, $CD_3OD$) δ 8.12 (d, J=7.8 Hz, 1H), 7.28-7.07 (m, 12H), 6.80 (d, J=8.8 Hz, 2H), 5.14 (dd, J=9.8, 10.7 Hz, 1H), 5.03 (ddd, J=7.3, 7.3, 11.2 Hz, 1H), 4.37-4.33 (m, 2H), 3.69 (ddd, J=2.9, 5.4, 8.3 Hz, 1H), 3.28-3.26 (m, 1H), 3.20 (dd, J=3.9, 8.3 Hz, 1H), 3.08 (dd, J=4.4, 13.7 Hz, 1H), 2.92 (dd, J=5.4, 14.7 Hz, 1H), 2.82-2.71 (m, 2H), 2.67 (dd, J=10.3, 14.2 Hz, 1H), 2.60 (ddd, J=3.9, 8.8, 11.7 Hz, 1H), 2.27 (ddd, J=5.9, 5.9, 14.6 Hz, 1H), 2.14 (ddd, J=8.3, 8.3, 14.6 Hz, 1H); HRMS (ES+) Calcd for $[C_{31}H_{38}N_3O_5]^+$ 532.2811. Found 532.2787.

Example 5

Synthesis of C-terminal Analogs

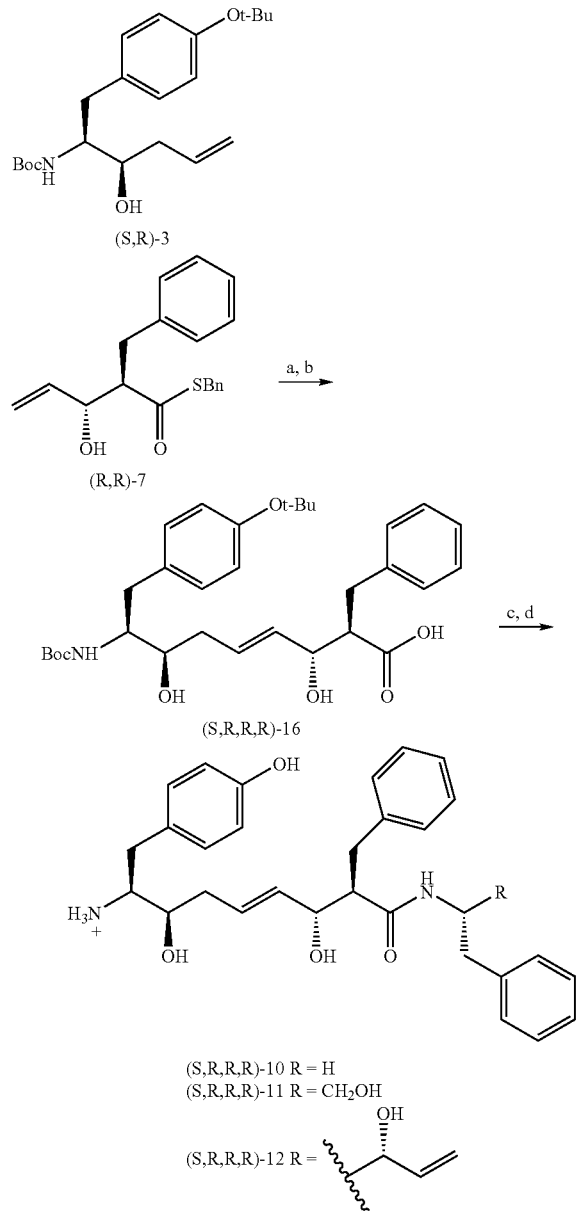

(a) Cl$_2$(PCy$_3$)(IMesH$_2$)RuCHPh, CH$_2$Cl$_2$, 40° C.; (b) LiOH, H$_2$O$_2$, 44% for two steps, (c) EDCI, HOBT, TEA, DMF, H$_2$NCHRCH$_2$Ph, (d) 1:1 CH$_2$Cl$_2$:TFA.

(E)-8-Amino-2-benzyl-3,7-dihydroxy-9-(4-hydroxy-phenyl)-non-4-enoic acid (16): Four stereoisomers of 16 were synthesized. Optimized procedure: To a mixture of (S,S)-3 (25 mg, 0.069 mmoles), (S,R)-7 (107 mg, 0.34 mmoles), and Cl$_2$(PCy$_3$)(IMesH$_2$)Ru=CHPh (18 mg, 0.021 mmoles) under Ar was added CH$_2$Cl$_2$ (2.1 mL). The reaction was heated at 45° C. for 1.5 hours, then concentrated under vacuum. The residue was purified by flash chromatography (4:1 hexanes:EtOAc to 1:1 hexanes:EtOAc) to give the cross metathesis heterodimer (about 36 mg, 81%) with small amounts of cross metathesis homodimers.

This mixture was dissolved in THF (40 mL per mmole), and a 1:1 mixture of 0.2 N LiOH (aq, 4 eq.) and 30% H$_2$O$_2$ (aq) was added. The reaction was stirred at room temperature for 3 hours, then cooled to 0° C. and quenched with 2 N NaHSO$_3$ (aq, 5 mL per mL 30% H$_2$O$_2$). The reaction was extracted with EtOAc, washed with brine, dried over MgSO$_4$, filtered, and concentrated under vacuum. The residue was purified by flash chromatography (1:4 hexanes:EtOAc to 1:4 hexanes:EtOAc with 4% AcOH) and concentrated under vacuum (rotovapping multiple times with toluene removed the acetic acid) to give (S,R,S,R)-16 (22 mg, 74%). Three other stereoisomers were synthesized in parallel with similar procedures.

(S,S,S,R)-16: $^1$H NMR (500 MHz, CD$_3$OD) δ 7.28-7.16 (m, 7H), 6.89 (d, J=8.8 Hz, 2H), 6.18 (d, J=9.8 Hz, 2H), 5.75 (ddd, J=6.8, 6.8, 15.6 Hz, 1H), 5.63 (dd, J=6.8, 15.1 Hz, 1H), 4.20 (t, J=7.3 Hz, 1H), 3.77-3.74 (m, 1H), 3.63-3.60 (m, 1H), 3.03 (dd, J=4.4 Hz, 1H), 2.90-2.82 (m, 2H), 2.77-2.70 (m, 2H), 2.26-2.22 (m, 2H), 1.38 (s, 9H), 1.32 (s, 9H); HRMS (ES+) Calcd for [C$_{31}$H$_{44}$NO$_7$]$^+$542.3118. Found 542.3109.

(S,S,R,R)-16: $^1$H NMR (500 MHz, CD$_3$OD) δ 7.26-7.12 (m, 7H), 6.83 (d, J=8.3 Hz, 12H), 6.12 (d, J=9.8 Hz, 1H), 5.72 (ddd, J=7.3, 7.3, 15.1 Hz, 1H), 5.60 (dd, J=7.8, 15.1 Hz, 1H), 4.16 (t, J=7.6 Hz, 1H), 3.80 (q, J=8.9 Hz, 1H), 3.62 (t, J=6.8 Hz, 1H), 2.90 (dd, J=3.9, 13.2 Hz, 1H), 2.83 (dd, J=6.3, 13.7 Hz, 1H), 2.77-2.70 (m, 3H), 2.29-2.04 (m, 2H), 1.40 (s, 9H), 1.30 (s, 9H); HRMS (ES+) Calcd for [C$_{31}$H$_{44}$NO$_7$]$^+$ 542.3118. Found 542.3107.

(S,R,R,R)-16: $^1$H NMR (500 MHz, CD$_3$OD) δ 7.27-7.14 (m, 7H), 6.88 (d, J=8.3 Hz, 2H), 6.48 (d, J=9.8 Hz, 1H), 5.83 (ddd, J=6.8, 6.8, 15.1 Hz, 1H), 5.66 (dd, J=7.3, 15.1 Hz, 1H), 4.22 (t, J=8.5 Hz, 1H), 3.71-3.67 (m, 1H), 3.62-3.58 (m, 1H), 3.06 (dd, J=3.4, 14.2 Hz, 1H), 2.92 (dd, J=4.4, 13.2 Hz, 1H), 2.80 (t, J=12.0 Hz, 1H), 2.72 (ddd, J=4.4, 7.8, 12.2 Hz, 1H), 2.54 (dd, J=10.3, 13.7 Hz, 1H), 2.46-2.40 (m, 1H), 2.27 (ddd, J=7.3, 7.3, 13.7 Hz, 1H), 1.34 (s, 9H), 1.32 (s, 9H); HRMS (ES+) Calcd for [C$_{31}$H$_{44}$NO$_7$]$^+$542.3118. Found 542.3125.

(S,R,S,R)-16: $^1$H NMR (500 MHz, CD$_3$OD) δ 7.25-7.11 (m, 7H), 6.86 (d, J=8.8 Hz, 2H), 6.43 (d, J=9.8 Hz, 1H), 5.79 (ddd, J=6.8, 6.8, 15.6 Hz, 1H), 5.65 (dd, J=7.3, 15.6 Hz, 1H), 4.20 (t, J=7.1 Hz, 1H), 3.67-3.62 (m, 1H), 3.56-3.53 (m, 1H), 3.05-3.00 (m, 2H), 2.87 (dd, J=4.9, 10.7 Hz, 1H), 2.74 (ddd, J=3.9, 7.3, 10.7 Hz, 1H), 2.51 (dd, J=10.7, 13.7 Hz, 1H), 2.36 (ddd, J=5.9, 5.9, 14.2 Hz, 1H), 2.21 (ddd, J=7.3, 7.3, 14.2 Hz, 1H), 1.30 (s, 9H), 1.28 (s, 9H); $^{13}$C NMR (100 MHz, CD$_3$OD) δ 177.0, 158.0, 154.6, 141.1, 135.8, 134.1, 131.0, 130.7, 130.0, 129.3, 127.2, 125.1, 79.8, 79.4, 74.7, 74.6, 57.7, 56.3, 38.0, 36.5, 35.7, 29.2, 28.8; HRMS (ES+)
Calcd for [C$_{31}$H$_{44}$NO$_7$]$^+$542.3118. Found 542.3122.

Compounds 10, 11, and 12: Three stereoisomers of each of three different analogs of 2 were synthesized by parallel solution phase amidation of three stereoisomers of 16: To a mixture of one stereoisomer of 16, EDCI.MeI (2 eq), and HOBT (2 eq) were added DMF (17 mL/mmole) and triethyl amine (3.2 eq). The solution was stirred for 10 minutes, followed by addition of 1.2 eq of an amine (phenethyl amine for 10, (S)-phenylalinol for 11, and (4S,3R)-4-amino-5-phenyl-pent-1-en-3-ol for 12). The reaction was stirred at room temperature overnight, then diluted with EtQAc, washed with 1N HCl (aq) and sat. NaHCO$_3$ (aq), dried over MgSO$_4$, filtered, and concentrated under vacuum. The protecting groups were removed by treating with 1:1 CH$_2$Cl$_2$:TFA for 1 hour, and the product was purified and analyzed the same as for 2. (E)-8-Amino-2-benzyl-3,7-dihydroxy-9-(4-hydroxy-phenyl)-non-4-enoic acid phenethyl-amide (10): Compounds 10 were synthesized from 16 in the following yields: (S,S,S,R)-10 13%, (S,S,R,R)-10 37%, (S,R,R,R)-10 41%.

(S,S,S,R)-10: $^1$H NMR (500 MHz, CD$_3$OD) δ 7.77 (t, J=5.9 Hz, 1H, slowly exchanges), 7.27-7.12 (m, 8H), 7.09 (d, J=8.8 Hz, 2H), 7.00 (d, J=7.3 Hz, 2H), 6.76 (d, J=8.8 Hz, 2H), 5.64 (ddd, J=6.3, 6.3, 15.6 Hz, 1H), 5.58 (dd, J=6.8, 15.6 Hz, 1H), 4.13 (t, J=7.1 Hz, 1H), 3.61 (q, J=5.7 Hz, 1H), 3.29-3.24 (m, 2H), 3.07-3.01 (m, 2H), 2.94 (dd, J=7.3, 14.2 Hz, 1h), 2.83 (dd, J=11.2, 13.7 Hz, 1H), 2.76 (dd, J=7.3, 14.2 Hz, 1H), 2.55-2.50 (m, 2H), 2.44 (ddd, J=8.3, 8.3, 13.7 Hz, 1H), 2.30-2.26 (m, 2H); HRMS (ES+) Calcd for [C$_{31}$H$_{38}$N$_3$O$_5$]$^+$ 489.2831. Found 489.2840.

(S,S,R,R)-10: $^1$H NMR (500 MHz, CD$_3$OD) δ 7.77 (t, J=5.9 Hz, 1H, slowly exchanges), 7.27-7.12 (m, 8H), 7.08 (d, J=8.3 Hz, 2H), 7.03 (d, J=6.8 Hz, 2H), 6.74 (d, J=8.8 Hz, 2H), 5.65 (ddd, J=6.6, 15.1 Hz, 1H), 5.58 (dd, J=6.8, 15.6 Hz, 1H), 4.13 (t, J=6.8 Hz, 1H), 3.65 (q, J=5.7 Hz, 1H), 3.35-3.32 (1H, obscured by solvent peak), 3.29-3.26 (1H, obscured by solvent peak), 3.18-3.12 (m, 1H), 2.96 (dd, J=7.3, 14.2 Hz, 1H), 2.78-2.74 (m, 3H), 2.57 (ddd, J=5.9, 7.8, 13.7 Hz, 1H), 2.51-2.45 (m, 2H), 2.33 (t, J=6.3 Hz, 2H); HRMS (ES+) Calcd for [C$_{31}$H$_{38}$N$_3$O$_5$]$^+$489.2753. Found 489.2764.

(S,R,R,R)-10: $^1$H NMR (500 MHz, CD$_3$OD) δ 7.26-7.11 (m, 10H), 7.04 (d, J=4.3 Hz, 2H), 6.77 (d, J=8.8 Hz, 2H), 5.67-5.62 (m, 2H), 4.16 (t, J=6.1 Hz, 1H), 3.83 (ddd, J=2.9, 5.4, 8.3 Hz, 1H), 3.43 (ddd, J=2.9, 4.9, 9.3 Hz, 1H), 3.35-3.31 (m, 1H), 3.19-3.13 (m, 1H), 2.98 (dd, J=5.4, 14.6 Hz, 1H), 2.84-2.72 (m, 3H), 2.60-2.46 (m, 3H), 2.36 (ddd, J=5.9, 13.7 Hz, 1H), 2.32-2.26 (m, 1H); HRMS (ES+) Calcd for [C$_{31}$H$_{38}$N$_3$O$_5$]$^+$489.2831. Found 489.2812.

(E)-8-Amino-2-benzyl-3,7-dihydroxy-9-(4-hydroxy-phenyl)-non-4-enoic acid (1-hydroxymethyl-2-phenyl-ethyl)-amide (11): Compounds 11 were synthesized from 16 in the following yields: (S,S,S,R)-11 20%, (S,S,R,R)-11 20%, (S,R,R,R)-11 53%.

(S,S,S,R)-11: $^1$H NMR (500 MHz, CD$_3$OD) δ 7.24-7.11 (m, 10H), 7.08 (d, J=8.3 Hz, 1H), 6.76 (d, J=8.3 Hz, 1H), 5.63 (ddd, J=7.3, 7.3, 15.6 Hz, 1H), 5.41 (dd, J=6.3, 15.1 Hz, 1H), 4.09 (t, J=6.8 Hz, 1H), 3.95-3.91 (m, 1H), 3.58 (ddd, J=5.4, 5.4, 6.8 Hz, 1H), 3.24-3.19 (m, 2H), 3.05 (dd, J=6.3, 10.7 Hz, 1H), 2.97 (dd, J=4.9, 13.7 Hz, 1H), 2.91 (dd, J=7.3, 14.2 Hz, 1H), 2.85-2.77 (m, 2H), 2.72 (dd, J=7.3, 14.2 Hz, 1H), 2.59-2.51 (m, 2H), 2.19-2.13 (m, 2H); HRMS (ES+) Calcd for [C$_{31}$H$_{39}$N$_2$O$_5$]$^+$519.2937. Found 519.2953.

(S,S,R,R)-11: $^1$H NMR (500 MHz, CD$_3$OD) δ 7.64 (d, J=8.8 Hz, 1H, slowly exchanges), 7.24-7.08 (m, 12H), 6.76 (d, J=8.3 Hz, 2H), 5.50 (dd, J=6.3, 15.1 Hz, 1H), 5.44 (ddd, J=6.3, 6.3, 15.6 Hz, 1H), 4.03 (t, J=6.3 Hz, 1H), 4.01-3.97 (m, 1H), 3.61 (ddd, J=4.9, 6.8, 6.8 Hz, 1H), 3.29-3.24 (2H, obscured by solvent peak), 3.17 (dd, J=5.9, 10.7 Hz, 1H), 2.94 (dd, J=7.3, 13.7 Hz, 1H), 2.88 (dd, J=5.9, 14.2 Hz, 1H), 2.77-2.71 (m, 3H), 2.62 (dd, J=8.8, 14.2 Hz, 1H), 2.52 (ddd, J=6.3, 6.3, 8.3 Hz, 1H), 2.27 (t, J=6.3 Hz, 2H); HRMS (ES+) Calcd for [C$_{31}$H$_{39}$N$_2$O$_5$]$^+$519.2937. Found 519.2945.

(S,R,R,R)-11: $^1$H NMR (500 MHz, CD$_3$OD) δ 7.24-7.10 (m, 12H), 6.78 (d, J=8.3 Hz, 2H), 5.54 (dd, J=7.3, 7.3, 15.1 Hz, 1H), 5.38 (ddd, J=7.3, 7.3, 15.1 Hz), 4.04 (t, J=6.3 Hz, 1H), 4.01-3.97 (m, 1H), 3.75 (ddd, J=2.9, 5.4, 8.3 Hz, 1H), 3.42 (ddd, J=2.9, 5.4, 9.3 Hz, 1H), 3.28 (1H, obscured by solvent peak), 3.17 (dd, J=6.3, 10.7 Hz, 1H), 2.96-2.88 (m, 2H), 2.83-2.71 (m, 3H), 2.63-2.55 (m, 2H), 2.28 (ddd, J=5.9, 5.9, 13.7 Hz, 1H), 2.20 (ddd, J=7.8, 7.8, 13.7 Hz, 1H); HRMS (ES+) Calcd for [C$_{31}$H$_{39}$N$_2$O$_5$]$^+$519.2937. Found 519.2923.

(E)-8-Amino-2-benzyl-3,7-dihydroxy-9-(4-hydroxy-phenyl)-non-4-enoic acid (1-benzyl-2-hydroxy-but-3-enyl)-amide (12): Compounds 12 were synthesized from 16 in the following yields: (S,S,S,R)-12 26%, (S,S,R,R)-12 33%, (S,R,R,R)-12 29%.

(S,S,S,R)-12: $^1$H NMR (500 MHz, CD$_3$OD) δ 7.62 (d, J=8.8 Hz, 1H, slowly exchanges), 7.23-7.08 (m, 12H), 6.77 (d, J=8.8 Hz, 2H), 5.63-5.52 (m, 2H), 5.32 (dd, J=6.8, 15.6 Hz, 1H), 5.16 (d, J=17.1 Hz, 1H), 5.01 (d, J=10.7 Hz, 1H), 4.05-4.01 (m, 2H), 3.80 (t, J=5.6 Hz, 1H), 3.58 (q, J=5.7 Hz, 1H), 3.22 (ddd, J=4.9, 7.3, 7.3 Hz, 1H), 2.92-2.76 (m, 4H), 2.72 (dd, J=7.3, 14.2 Hz, 1H), 2.63-2.56 (m, 2H), 2.22-2.14 (m, 2H); HRMS (ES+) Calcd for [C$_{33}$H$_{41}$N$_2$O$_5$]$^+$545.3015. Found 545.2996.

(S,S,R,R)-12: $^1$H NMR (500 MHz, CD$_3$OD) δ 7.76 (d, J=9.3 Hz, 1H, slowly exchanges), 7.23-7.10 (m, 12H), 6.78 (d, J=8.8 Hz, 2H), 5.62 (ddd, J=5.3, 10.3, 16.6 Hz, 1H), 5.41 (dd, J=7.3, 15.6 Hz, 1H), 5.21-5.14 (m, 2H), 4.99 (d, J=10.7 Hz, 1H), 4.05-4.01 (m, 1H), 3.90 (t, J=6.1 Hz, 1H), 3.84 (t, J=5.6 Hz, 1H), 3.58 (q, J=5.7 Hz, 1H), 3.25 (ddd, J=4.4, 7.3, 7.3 Hz, 1H), 3.00-2.92 (m, 2H), 2.78-2.67 (m, 3H), 2.61-2.54 (m, 2H), 2.22 (t, J=13.7 Hz, 2H); HRMS (ES+) Calcd for [C$_{33}$H$_{41}$N$_2$O$_5$]$^+$545.3015. Found 545.3032.

(S,R,R,R)-12: $^1$H NMR (500 MHz, CD$_3$OD) δ 7.23-7.08 (m, 12H), 6.80 (d, J=8.3 Hz, 2H), 5.57 (ddd, J=5.9, 10.3, 17.1 Hz, 1H), 5.45 (dd, J=7.8, 15.6 Hz, 1H), 5.13 (d, J=17.1 Hz, 1H), 5.02 (ddd, J=7.3, 7.3, 15.1 Hz, 1H), 4.95 (d, J=10.3 Hz, 1H), 4.01 (ddd, J=3.9, 5.9, 10.3 Hz, 1H), 3.92 (dd, J=4.4, 7.3 Hz, 1H), 3.80 (t, J=5.9 Hz, 1H), 3.68-3.65 (m, 1H), 3.43 (ddd, J=2.9, 5.4, 8.8 Hz, 1H), 3.01 (dd, J=3.9, 14.2 Hz, 1H), 2.92 (dd, J=5.9, 14.7 Hz, 1H), 2.82-2.71 (m, 3H), 2.62 (ddd, J=4.4, 4.4, 10.3 Hz, 1H), 2.56 (dd, J=10.3, 14.2 hz, 1H), 2.21 (ddd, J=5.9, 5.9, 13.7 Hz, 1H), 2.12 (ddd, J=8.3, 8.3, 13.7 Hz, 1H); HRMS (ES+) Calcd for [C$_{33}$H$_{41}$N$_2$O$_5$]$^+$545.3015. Found 545.3022.

Example 6

Synthesis of C-terminal Analog 13

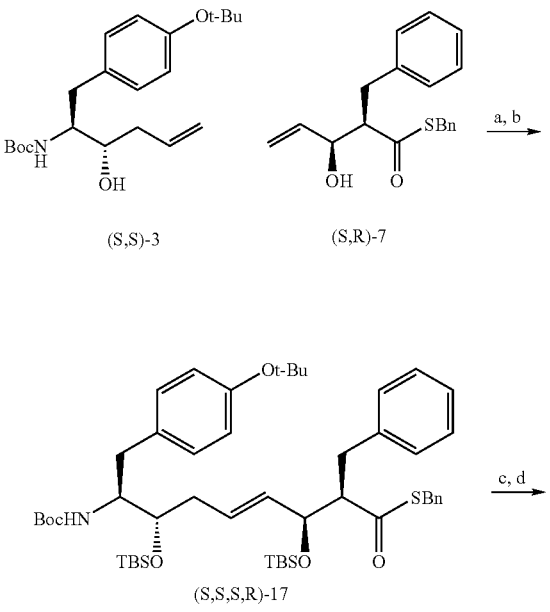

-continued

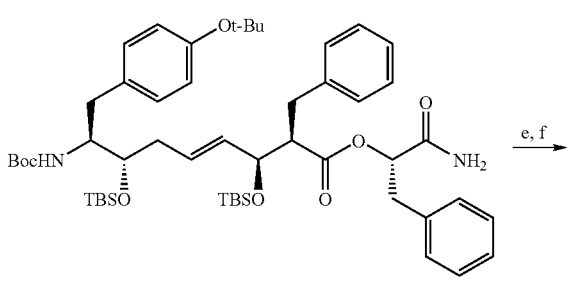

(S,S,S,R)-18

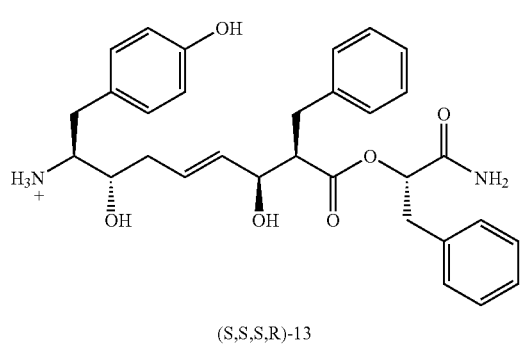

(S,S,S,R)-13

(a) Cl₂(PCy₃)(IMesH₂)RuCHPh, CH₂Cl₂, 40° C.; (b) TBSCl, imidazole, DMF, 83%; (c) LiOH, H₂O₂, THF, MeOH, H₂O; (d) (S)-2-Hydroxy-3-phenyl-propionamide, EDCI, DMAP, CH₂Cl₂, 77% for 2 steps; (e) 48% HF, acetonitrile; (f) 1:1 CH₂Cl₂:TFA, 55% for 2 steps.

(E)-2-Benzyl-8-tert-butoxycarbonylamino-9-(4-tert-butoxy-phenyl)-3,7-bis-(tert-butyl-dimethyl-silanyloxy)-non-4-enethioic acid S-benzyl ester (17): Monomers (S,S)-3 and (3S,2R)-7 were cross metathesized in a similar manner as in the synthesis of 16. To a mixture of the cross metathesis product (50 mg, 0.077 mmole) and imidazole (16 mg, 0.23 mmole) in DMF (77 µL) under Ar was added TBSCl (29 mg, 0.19 mmole). The reaction was stirred for 16 hours, then diluted with EtOAc, washed with H₂O twice and saturated NaHCO₃ (aq), dried over MgSO₄, filtered, and concentrated under vacuum. The residue was purified by flash chromatography (16:1 hexanes:EtOAc to 8:1 hexanes:EtOAc) to give 56 mg (83%) of (S,S,S,R)-17 as a clear oil.

(S,S,S,R)-17: $^1$H NMR (500 MHz, C₆D₆) δ 7.24-6.95 (m, 14H), 5.79-5.70 (m, 2H), 4.80 (d, J=9.8 Hz, 1H), 4.43 (t, J=5.1 Hz, 1H), 4.30 (q, J=8.0 Hz, 1H), 3.95 (d, J=14.2 Hz, 1H), 3.86 (d, J=14.2 Hz, 1H), 3.82 (dd, J=4.4, 7.8 Hz, 1H), 3.22-3.16 (m, 2H), 3.13-3.09 (m, 1H), 2.83 (dd, J=5.9, 13.7 Hz, 1H), 2.77 (dd, J=8.8, 13.7 Hz, 1H), 2.44 (ddd, J=8.8, 8.8, 13.2 Hz, 1H), 2.21 (ddd, J=4.9, 4.9, 14.2 Hz, 1H), 1.34 (s, 9H), 1.19 (s, 9H), 1.01 (s, 9H), 0.90 (s, 9H), 0.10 (s, 3H), 0.07 (s, 3H), 0.05 (s, 3H), 0.02 (s, 3H); MS (ES+) Calcd for [C₅₀H₇₈NO₆SSi₂]⁺ 876.5. Found 876.3.

(E)-2-Benzyl-8-tert-butoxycarbonylamino-9-(4-tert-butoxy-phenyl)-3,7-bis-(tert-butyl-dimethyl-silanyloxy)-non-4-enoic acid 1-carbamoyl-2-phenyl-ethyl ester (18): To a solution of (S,S,S,R)-17 (15 mg, 0.017 mmole) in THF:MeOH:H₂O (3:1:1, 340 µL) was added 1N LiOH (aq, 68 µL, 0.068 mmole) and 30% H₂O₂ (aq, 10.5 µL). After stirring for 6 hours at room temperature, the reaction was quenched with 2N NaHSO₃ (aq, 60 µL), diluted with EtOAc, washed with H₂O, sat. NaHCO₃ (aq), and brine, dried over MgSO₄, filtered, and concentrated under vacuum.

The residue was combined with (S)-2-Hydroxy-3-phenyl-propionamide (5.6 mg, 0.034 mmole), EDCI.MeI (10 mg, 0.034 mmole), and DMAP (4.1 mg, 0.034 mmole) in a flame dried vial. CH₂Cl₂ (400 µL) was added, and the reaction was stirred for 24 hours, then diluted with EtOAc, washed with 1N HCl (aq) twice and sat NaHCO₃ (aq), dried over MgSO₄, filtered, and concentrated under vacuum. The residue was purified by flash chromatography (4:1 hexanes:EtOAc to 2:1 hexanes:EtOAc) to give 12 mg (77% for two steps) of (S,S,S,R)-18 as an oil.

(S,S,S,R)-18: $^1$H NMR (500 MHz, C₆D₆) δ 7.24-6.87 (m, 14H), 5.81-5.80 (m, 2H), 5.42 (dd, J=4.9, 6.3 Hz, 1H), 4.95-4.88 (m, 3H), 4.39-4.36 (m, 1H), 4.25 (q, J=8.3 Hz, 1H), 3.82 (dd, J=3.4, 8.3 Hz, 1H), 3.20-3.12 (m, 2H), 3.10 (dd, J=4.4, 13.2 Hz, 1H), 3.00 (ddd, J=4.4, 6.8, 11.2 Hz, 1H), 2.88 (t, J=12.2 Hz, 1H), 2.84-2.81 (m, 2H), 2.51-2.47 (m, 1H), 2.28-2.25 (d, J=14.6 Hz, 1H), 1.36 (s, 9H), 1.23 (s, 9H), 1.02 (s, 9H), 0.90 (s, 9H), 0.14 (s, 3H), 0.07 (s, 3H), 0.05 (s, 3H), 0.01 (s, 3H); MS (ES+) Calcd for [C₅₂H₈₁N₂O₈SSi₂]⁺ 917.6. Found 917.9.

(E)-8-Amino-2-benzyl-3,7-dihydroxy-9-(4-hydroxy-phenyl)-non-4-enoic acid 1-carbamoyl-2-phenyl-ethyl ester (13): To a solution of (S,S,S,R)-18 (12 mg) in MeCN (400 µL) in a plastic tube was added 48% HF (aq, 8 µL). The reaction was stirred for 22 hours, then quenched with sat. NaHCO₃ (aq) and extracted with EtOAc. The EtOAc extract was washed with sat. NaHCO₃ (aq) and brine, dried over MgSO₄, filtered, and concentrated under vacuum.

The residue was treated with 1:1 CH₂Cl₂:TFA for 1 hour to remove the protecting groups, and the product was purified and analyzed the same as for 2 to give 7.1 µmole (55% for two steps) of (S,S,S,R)-13.

(S,S,S,R)-13: $^1$H NMR (500 MHz, CD₃OD) δ 7.31-7.21 (m, 5H), 7.15-7.07 (m, 5H), 6.81 (d, J=7.8 Hz, 2H), 6.75 (d, J=8.3 Hz, 2H), 5.69-5.66 (m, 2H), 4.99 (dd, J=3.9, 8.8 Hz, 1H), 4.25 (t, J=5.9 Hz, 1H), 3.63 (ddd, J=4.4, 6.3, 6.3 Hz, 1H), 3.28 (ddd, J=4.4, 7.3, 7.3 Hz, 1H), 3.09 (dd, J=4.4, 14.2 Hz, 1H) 3.02 (dd, J=8.8, 14.2 Hz, 1H), 2.98-2.92 (m, 2H), 2.78-2.69 (m, 2H), 2.31-2.28 (m, 2H); HRMS (ES+) Calcd for [C₃₁H₃₇N₂O₆]⁺ 533.2652. Found 533.2629.

Example 7

Synthesis of N-terminal 2,6, Dimethyl Tyrosine Monomers

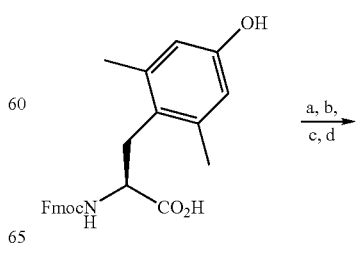

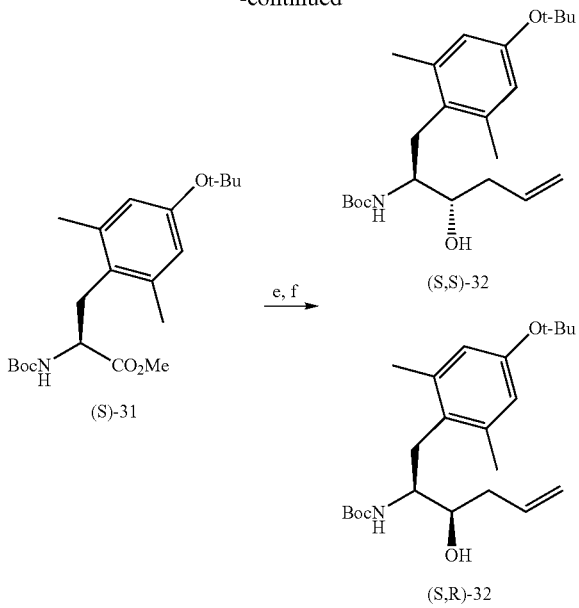

(a) SOCl$_2$, MeOH; (b) isobutylene (5 psi), H$_2$SO$_4$, CH$_2$Cl$_2$, 71%, 2 steps; (c) NHMe$_2$, THF; (d) Boc$_2$O, NEt$_3$, THF, 97%, 2 steps; (e) DIBAL-H, toluene, -78° C.; (f) allylMgBr, THF, Et$_2$O, 0° C., 27% (S,S)-32, 38% (S,R)-32, 2 steps.

Fmoc-2,6-dimethyl-(L)-Tyr(tBu)-OMe: To a mixture of Fmoc-2,6-dimethyl-(L)-tyrosine (516 mg, 1.2 mmole) in MeOH (2.4 mL) was added thionyl chloride (178 μL, 2.4 mmole). The reaction was stirred for 1.5 hours, then diluted with EtOAc, washed with H$_2$O, sat. NaHCO$_3$ (aq), and brine, dried over MgSO$_4$, and concentrated under vacuum to give Fmoc-2,6-dimethyl-(L)-Tyr-OMe. This material was dissolved in CH$_2$Cl$_2$ (9.6 mL), and concentrated sulfuric acid (32 μL, 0.6 mmol) was added. The solution was stirred vigorously under an atmosphere of isobutylene (5 psi) for 16 hours. The isobutylene was vented, and the reaction was quenched with sat. NaHCO$_3$ (aq), then diluted with EtOAc, washed with sat. NaHCO$_3$ (aq) and brine, dried over MgSO$_4$, and concentrated under vacuum. The residue was purified by flash:chromatography (8:1 hexanes:EtOAc to 4:1 hexanes:EtOAc) to give 425 mg (71%) of Fmoc-2,6-dimethyl-(L)-Tyr(tBu)-OMe as a white foam plus 92 mg (17%) of Fmoc-2,6-dimethyl-(L)-Tyr-OMe.

Fmoc-2,6-dimethyl-(L)-Tyr-OMe: $^1$H NMR (500 MHz, CDCl$_3$) δ 7.76 (d, J=7.3 Hz, 2H), 7.55 (t, J=7.6 Hz, 2H), 7.40 (t, J=7.3 Hz, 2H), 7.31 (t, J=7.3 Hz, 2H), 6.51 (s, 2H), 5.32 (d, J=8.3 Hz, 1H), 4.56 (q, J=8.0 Hz, 1H), 4.49 (s, 1H), 4.36-4.29 (m, 2H), 4.17 (t, J=7.1 Hz, 1H), 3.67 (s, 3H), 3.07-3.00 (m, 1H), 2.29 (s, 6H); MS (ES+) Calcd for [C$_{27}$H$_{28}$NO$_5$]$^+$446. Found 446.

Fmoc-2,6-dimethyl-(L)-Tyr(tBu)-OMe: $^1$H NMR (500 MHz, CDCl$_3$) δ 7.79 (d, J=7.3° Hz, 2H), 7.58 (t, J=7.1 Hz, 2H), 7.43 (t, J=7.3 Hz, 2H), 7.34 (t, J=7.6 Hz, 2H), 6.68 (s, 2H), 5.37 (d, J=8.8 Hz, 1H), 4.60 (q, J=8.1 Hz, 1H), 4.34 (d, J=7.3 Hz, 2H), 4.20 (t, J=7.1 Hz, 1H), 3.64 (s, 3H), 3.09 (d, J=8.3 Hz, 2H), 2.33 (s, 6H), 1.32 (s, 9H); MS (ES+) Calcd for [C$_{31}$H$_{36}$NO$_5$]$^+$502. Found 502.

Boc-2,6-dimethyl-(L)-Tyr(tBu)-OMe ((S)-31): Fmoc-2,6-dimethyl-(L)-Tyr(tBu)-OMe (413 mg, 0.82 mmole) was treated with 2N NHMe$_2$ in THF (8.2 mL) for 1 hour. The solvent was removed under vacuum, and Boc$_2$O (376 μL, 1.6 mmole), THF (8.2 mL), and NEt$_3$ (227 μL, 1.6 mmole) were added. The reaction was stirred for 1 hour, and then diluted with EtOAc, quenched with water, washed with 1N HCl (aq), water, sat. NaHCO$_3$ (aq), and brine, dried over MgSO$_4$, and concentrated under vacuum. The residue was purified by flash chromatography (8:1 hexanes:EtOAc to 4:1 hexanes:EtOAc) to give 302 mg (97%) of (S)-31 as a clear oil. (S)-31: $^1$H NMR (500 MHz, CDCl$_3$) δ 6.65 (s, 2H), 5.06 (d, J=8.3 Hz, 1H), 4.51 (q, J=8.0 Hz, 1H), 3.60 (s, 3H), 3.01 (d, J=7.8 Hz, 1H), 2.30 (s, 6H), 1.38 (s, 9H), 1.32 (s, 9H); MS (ES+) Calcd for [C$_{21}$H$_{34}$NO$_5$]$^+$380. Found 380.

[1-(4-tert-Butoxy-2,6-dimethyl-benzyl)-2-hydroxy-pent-4-enyl]-carbamic acid tert-butyl ester (32): To a stirred solution of (S)-31 (134 mg, 0.35 mmole) in toluene (7.1 mL) at −78° C. under N$_2$ was added DIBAL-H (1 M in hexanes, 0.71 mL, 0.71 mmole) dropwise over 30 minutes. The reaction was stirred for 30 minutes, then quenched by the slow addition of MeOH (1.3 mL, 31.5 mmole) and warmed to room temperature. Rochelle's salt (0.5 M aq., 2.8 mL, 1.4 mmole) was added, and the mixture was stirred for 1 hour, then extracted with ether. The ether extract was washed with water and brine, dried over MgSO$_4$, filtered, and concentrated under vacuum to give Boc-2,6-dimethyl-(L)-Tyr(tBu)-H.

Without further purification, the aldehyde was placed under N$_2$, dissolved in THF (3.5 mL), cooled to 0° C., and treated with allyl magnesium bromide (1M in Et$_{2}$O, 1.75 mL, 1.75 mmole). The reaction was stirred for 4 hours at 0° C., then quenched with 1N HCl (aq) and extracted with EtOAc. The EtOAc extract was washed with water, sat. NaHCO$_3$ (aq) and brine, dried over MgSO$_4$, filtered, and concentrated under vacuum. Crude NMR showed a 1.5:1 ratio of diastereomers.

The diastereomers were separated by flash chromatography (8:1 hexanes:EtOAc to 4:1 hexanes:EtOAc to 2:1 hexanes:EtOAc) to give an upper fraction containing (S,S)-32 with some aldehyde and a byproduct and a lower fraction containing (S,R)-32 in a 4:1 ratio with (S,S)-32. The upper fraction was flashed (2:1 hexanes:EtOAc to 1:1 hexanes:EtOAc) to give 38 mg (27%) of (S,S)-32 (>20:1 ratio of diastereomers) as an oil. The lower fraction was flashed twice (8:1 hexanes:EtOAc to 4:1 hexanes:EtOAc to 2:1 hexanes:EtOAc) to give 53 mg (38%) of (S,R)-32 (>10:1 ratio of diastereomers) as a white solid.

(S,S)-32: $^1$H NMR (500 MHz, CDCl$_3$) δ 6.64 (s, 2H), 5.75-5.68 (m, 1H), 5.11-5.07 (m, 2H), 4.97 (d, J=9.3 Hz, 1H), 3.75 (q, J=7.8 Hz, 1H), 3.52 (br s, 1H), 2.93-2.86 (m, 2H), 2.33 (s, 6H), 2.21 (t, J=6.3 Hz, 2H), 1.39 (s, 9H), 1.32 (s, 9H); $^{13}$C NMR (100 MHz, CDCl$_3$) δ 155.8, 153.1, 137.8, 134.4, 130.1, 123.6, 118.6, 79.0, 77.8, 70.1, 53.4, 39.5, 32.4, 28.9, 28.3, 20.4; HRMS (ES+) Calcd for [C$_{23}$H$_{38}$NO$_4$]$^+$392.2801. Found 392.2806.

(S,R)-32: $^1$H NMR (500 MHz, CDCl$_3$) δ 6.64 (s, 2H), 5.92-5.84 (m, 1H), 5.20-5.17 (m, 2H), 4.64 (br s, 1H), 3.83-3.79 (m, 2H), 2.84-2.81 (m, 2H), 2.74 (br s, 1H), 2.42-2.38 (m, 1H), 2.33-2.26 (m, 1H), 2.30 (s, 6H), 1.32 (s, 9H), 1.30 (s, 9H); $^{13}$C NMR (100 MHz, CDCl$_3$) δ 155.7, 153.1, 137.5, 134.7, 130.0, 123.7, 118.1, 79.2, 77.8, 73.7, 54.6, 38.5, 28.8, 28.2, 20.5; HRMS (ES+) Calcd for [C$_{23}$H$_{38}$NO$_4$]$^+$392.2801. Found 392.2802.

To determine the relative configuration of compounds 32, (S,S)-32 and (S,R)-32 were cyclized to (S,S)-36 and (S,R)-36, respectively, by treatment with base. (S,S)-36 showed a much weaker NOE between H$^2$ and H$^3$ than (S,R)-36; therefore, (S,S)-32 was assigned as the anti diastereomer and (S,R)-32 as the syn diastereomer.

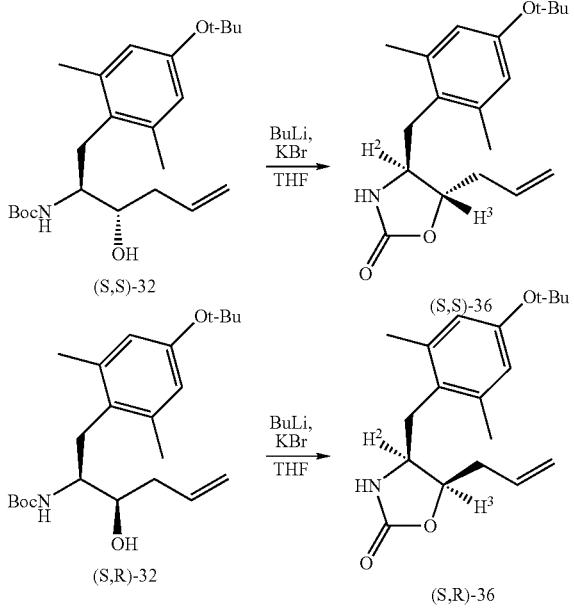

(S,S)-36 (anti): $^1$H NMR (500 MHz, CDCl$_3$) δ 6.68 (s, 2H), 5.78-5.70 (m, 1H), 5.19-5.15 (m, 2H), 4.66 (br s, 1H), 4.36 (q, J=5.9 Hz, 1H), 3.73 (ddd, J=4.9, 4.9, 9.3 Hz, 1H), 2.90 (dd, J=10.3, 14.2 Hz, 1H), 2.81 (dd, J=4.9, 14.2 Hz, 1H), 2.50 (ddd, J=5.9, 5.9, 14.2 Hz, 1H), 2.42 (ddd, J=6.8, 6.8, 14.2 Hz, 1H), 2.28 (s, 6H), 1.33 (s, 9H); NOE $^1$H NMR (500 MHz, CDCl$_3$), irradiate 3.73, NOE 4.36 0.4%; HRMS (ES+) Calcd for [C$_{19}$H$_{28}$NO$_3$]$^+$ 318.2069. Found 318.2073.

(S,R)-36 (syn): $^1$H NMR (500 MHz, CDCl$_3$) δ 6.69 (s, 2H), 5.95-5.87 (m, 1H), 5.29 (dd, J=1.5, 17.1 Hz, 1H), 5.24 (d, J=10.3 Hz, 1H), 4.75 (q, J=7.2 Hz, 1H), 4.70 (br s, 1H), 3.94 (ddd, J=3.4, 7.3, 11.7 Hz, 1H), 2.92 (t, J=12.7 Hz, 1H), 2.77-2.73 (m, 2H), 2.59 (ddd, J=6.8, 6.8, 15.1 Hz, 1H), 2.26 (s, 6H), 1.33 (s, 9H).); NOE $^1$H NMR (500 MHz, CDCl$_3$), irradiate 3.94, NOE 4.75 9.7%; HRMS (ES+) Calcd for [C$_{19}$H$_{28}$NO$_3$]$^+$ 318.2069. Found 318.2063.

Example 8

Synthesis of 2,6-Dimethyl Stereodiversified Analogs

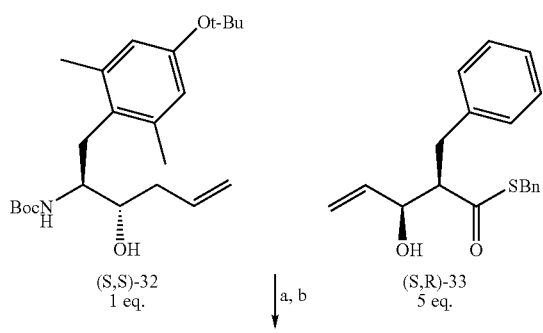

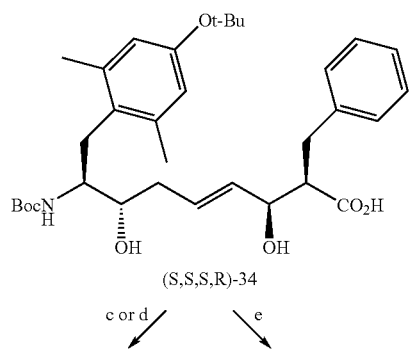

-continued

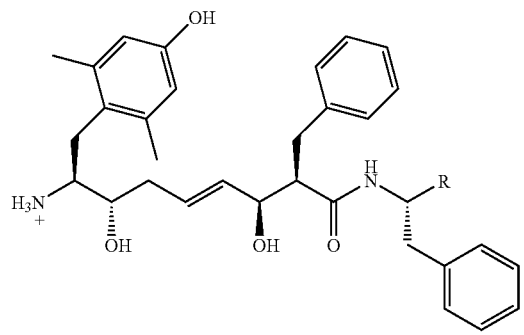
(S,S,S,R)-25 R = CONH$_2$
(S,S,S,R)-26 R = H
(S,S,S,R)-27 R = CH$_2$OH

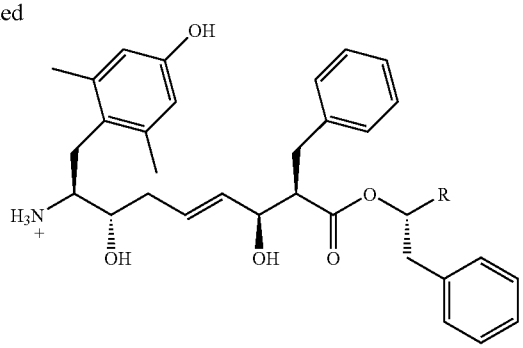
(S,S,S,R)-28 R = CONH$_2$
(S,S,S,R)-29 R = H (a) Cl$_2$(PCy$_3$)(IMesH$_2$)RuCHPh, CH$_2$Cl$_2$, 40° C.; (b) LiOH, H$_2$O$_2$, THF, H$_2$O, 54%, 2 steps; (c) for 25: HBTU, HOBT, DIPEA, NMP, Phe-NH-Rink Amide AM resin, then 95% TFA, 63%; (d) for 26 and 27: EDCI, HOBT, NEt$_3$, (S)-H$_2$N(CHR)CH$_2$Ph, then 95% TFA, 52% for 26, 51% for 27; (e) EDCI, DMAP, (S)-HO(CHR)CH$_2$Ph (10-20 eq.), CH$_2$Cl$_2$, then 95% TFA, 21% for 28, 20% for 29.

2-Benzyl-8-tert-butoxycarbonylamino-9-(4-tert-butoxy-2,6-dimethyl-phenyl)-3,7-dihydroxy-non-4-enoic acid (34): Five stereoisomers were synthesized by the following procedure: To a mixture of 32 (20 mg, 0.051 mmoles), 33 (80 mg, 0.26 mmoles), and Cl$_2$(PCy$_3$)(IMesH$_2$)Ru=CHPh (13 mg, 0.015 mmoles) under Ar was added CH$_2$Cl$_2$ (105 mL). The reaction was heated at 45° C. for 2 hours, then concentrated under vacuum. The residue was purified by flash chromatography (16:1 to 4:1 CH$_2$Cl$_2$:EtOAc) to give the cross metathesis heterodimer.

This product was dissolved in THF (40 mL per mmole), and equal volumes of 0.2 N LiOH (aq) (4 eq.) and 30% H$_2$O$_2$ (aq) were added. The reaction was stirred at room temperature for 3 hours, then cooled to 0° C. and quenched with 2 N NaHSO$_3$ (aq) (200 eq.). The reaction was extracted with EtOAc, washed with brine, dried over MgSO$_4$, filtered, and concentrated under vacuum. The residue was purified by flash chromatography (1:2 hexanes:EtOAc to 1:2 hexanes:EtOAc with 2% AcOH) and concentrated under vacuum (rotovapping multiple times with toluene removed the acetic acid) to give 34. Yields: (S,S,S,R)-34 (16 mg, 54%), (S,R,S,R)-34 (17 mg, 59%), (S,S,R,R)-34 (15 mg, 50%), (S,R,R,R)-34 (17 mg, 59%), (S,S,R,S)-34 (16 mg, 55%).

(S,S,S,R)-34: $^1$H NMR (500 MHz, CD$_3$OD) δ 7.24-7.10 (m, 5H), 6.59 (s, 2H), 5.95 (d, J=9.8 Hz, 1H), 5.69 (ddd, J=6.3, 6.3, 15.1 Hz, 1H), 5.59 (dd, J=6.8, 15.1 Hz, 1H), 4.16 (t, J=7.1 Hz, 1H), 3.80 (q, J=5.4 Hz, 1H), 3.59 (t, J=6.3 Hz, 1H), 2.99 (dd, J=4.4, 13.7 Hz, 1H), 2.91-2.78 (m, 3H), 2.71 (ddd, J=3.9, 6.8, 10.3 Hz, 1H), 2.31 (s, 6H), 2.21 (t, J=6.8 Hz, 2H), 1.32 (s, 9H), 1.27 (s, 9H), there is also an additional set of smaller peaks, believed to be from a rotamer; HRMS (ES+) Calcd for [C$_{33}$H$_{48}$NO$_7$]$^+$570.3431. Found 570.3408.

(S,R,S,R)-34: $^1$H NMR (500 MHz, CD$_3$OD) δ 7.25-7.13 (m, 5H), 6.59 (s, 2H), 6.31 (d, J=10.3 Hz, 1H), 5.81 (ddd, J=6.8, 6.8, 15.1 Hz, 1H), 5.66 (dd, J=6.8, 15.1 Hz, 1H), 4.20 (t, J=7.1 Hz, 1H), 3.75-3.68 (m, 1H), 3.63-3.59 (m, 1H), 3.03-2.99 (m, 2H), 2.88 (dd, J=10.3, 13.7 Hz, 1H), 2.77-2.66 (m, 2H), 2.43-2.38 (m, 1H), 2.31 (s, 6H), 2.26-2.18 (m, 1H), 1.27 (s, 9H), 1.25 (s, 9H), there is also an additional set of smaller peaks, believed to be from a rotamer; HRMS (ES+) Calcd for [C$_{33}$H$_{48}$NO$_7$]$^+$570.3431. Found 570.3408.

(S,S,R,R)-34: $^1$H NMR (500 MHz, CD$_3$OD) δ 7.23-7.13 (m, 5H), 6.56 (s, 2H), 5.88 (d, J=9.8 Hz, 1H), 5.68 (ddd, J=7.3, 7.3, 15.1 Hz, 1H), 5.53 (dd, J=7.8, 15.1 Hz, 1H), 4.13 (t, J=7.6 Hz, 1H), 3.82 (dddd, J=2.0, 8.5, 8.5, 8.5 Hz, 1H), 3.59 (ddd, J=2.0, 6.3, 6.3 Hz, 1H), 2.89-2.79 (m, 3H), 2.72-2.66 (m, 2H), 2.28 (s, 6H), 2.24 (t, J=6.8 Hz, 2H), 1.34 (s, 9H), 1.26 (s, 9H), there is also an additional set of smaller peaks, believed to be from a rotamer; HRS (ES+) Calcd for [C$_{33}$H$_{48}$NO$_7$]$^+$570.3431. Found 570.3433.

(S,R,R,R)-34: $^1$H NMR (500 MHz, CD$_3$OD) δ 7.24-7.13 (m, 5H), 6.58 (s, 2H), 6.29 (d, J=10.3 Hz, 1H), 5.82 (ddd, J=6.8, 6.8, 15.1 Hz, 1H), 5.62 (dd, J=7.8, 15.6 Hz, 1H), 4.20 (t, J=7.6 Hz, 1H), 3.75-3.71 (m, 1H), 3.66-3.62 (m, 1H), 3.02 (dd, J=2.9, 14.2 Hz, 1H), 2.89 (dd, J=3.9, 13.2 Hz, 1H), 2.80-2.67 (m, 3H), 2.46-2.38 (m, 1H), 2.31 (s, 6H), 2.29-2.23 (m, 1H), 1.27 (s, 9H), 1.26 (s, 9H), there is also an additional set of smaller peaks, believed to be from a rotamer; HRMS (ES+) Calcd for [C$_{33}$H$_{48}$NO$_7$]$^+$570.3431. Found 570.3437.

(S,S,R,S)-34: $^1$H NMR (500 MHz, CD$_3$OD) δ 7.24-7.13 (m, 5H), 6.60 (s, 2H), 5.95 (d, J=10.3 Hz, 1H), 5.71 (ddd, J=6.8, 6.8, 15.1 Hz, 1H), 5.62 (dd, J=6.8, 15.1 Hz, 1H), 4.18 (t, J=7.1 Hz, 1H), 3.80 (q, J=5.1 Hz, 1H), 3.58 (t, J=6.6 Hz, 1H), 3.00 (dd, J=4.4, 13.7 Hz, 1H), 2.88-2.79 (m, 3H), 2.71 (ddd, J=4.4, 6.8, 10.7 Hz, 1H), 2.31 (s, 6H), 2.21 (t, J=5.4 Hz, 2H), 1.32 (s, 9H), 1.28 (s, 9H), there is also an additional set of smaller peaks, believed to be from a rotamer; HRMS (ES+) Calcd for [C$_{33}$H$_{48}$NO$_7$]$^+$570.3431. Found 570.3428.

7-(1-Carbamoyl-2-phenyl-ethylcarbamoyl)-2,6-dihydroxy-1-(4-hydroxy-2,6-dimethyl-benzyl)-8-phenyl-oct-4-enyl-ammonium (25): Five stereoisomers were synthesized in parallel by the following procedure: A solution of 34 (5.7 mg, 0.010 mmole), HBTU (3.8 mg, 0.010 mmole), HOBT (1.4 mg, 0.010 mmole), and DIPEA (3.5 μL, 0.020 mmole) in NMP (400 μL) was added to Rink Amide AM resin loaded with phenylalanine (47 mg resin, 0.030 mmole Phe). Nitrogen was bubbled through the mixture for 1 hour. The resin was washed with NMP (3×), NMP alternating with IPA (3×), and CH$_2$Cl$_2$ alternating with Et$_2$O (3×), then dried under vacuum for 2 hours. The product was deprotected from the resin by treatment with TFA:H$_2$O:TIS (95:2.5:2.5, 600 μL) for 1 hour. The TFA solution was concentrated under a stream of nitrogen. The residue was dissolved in MeCN/H$_2$O (1:1, 300 μL), and the product was isolated by HPLC (25 cm semiprep C18 column, 20% to 50% MeCN:H$_2$O with 0.1% TFA over 15 minutes, 2 mL/min). The product was quantified by HPLC (25 cm analytical C18 column, 20% to 50% MeCN:H$_2$O with 0.1% TFA over 15 minutes, 1.5 mL/min) based on UV absorbance at 280 nM of 2,6-dimethyltyrosine (4.4×10$^4$ mAu·s/µmole). This HPLC run combined with NMR analysis confirmed that the purity of the products was greater than 95%. Yields: (S,S,S,R)-25 (6.3 µmole, 63%), (S,R,S,R)-25 (5.3 µmole, 53%), (S,S,R,R)-25 (5.3 µmole, 53%), (S,R,R,R)-25 (4.8 µmole, 148%), (S,S,R,S)-25 (4.8 µmole, 48%).

(S,S,S,R)-25: $^1$H NMR (500 MHz, CD$_3$OD) δ 7.85 (d, J=7.8 Hz, 1H), 7.22-7.08 (m, 10H), 6.50 (s, 2H), 5.53 (ddd, J=6.8, 6.8, 15.6 Hz, 1H), 5.32 (dd, J=6.3, 15.6 Hz, 1H), 4.44 (ddd, J=5.9, 8.3, 8.3 Hz, 1H), 4.06 (t, J=6.3 Hz, 1H), 3.53 (ddd, J=3.4, 6.3, 6.3 Hz, 1H), 3.25 (ddd, J=3.9, 5.9, 9.3 Hz, 1H), 3.10 (dd, J=9.3, 14.2 Hz, 1H), 3.02 (dd, J=4.4, 13.7 Hz, 1H), 2.90 (dd, J=4.9, 13.7 Hz, 1H), 2.84-2.75 (m, 3H), 2.60 (ddd, J=4.9, 6.3, 10.7 Hz, 1H), 2.28 (s, 6H), 2.12 (t, J=6.6 Hz, 2H); HRMS (ES+) Calcd for [C$_{33}$H$_{42}$N$_3$O$_5$]$^+$560.3124. Found 560.3137.

(S,R,S,R)-25: $^1$H NMR (500 MHz, CD$_3$OD) δ 7.90 (d, J=8.3 Hz, 1H), 7.25-7.13 (m, 8H), 7.11 (d, J=6.8 Hz, 2H), 6.51 (s, 2H), 5.65 (ddd, J=6.8, 6.8, 15.6 Hz, 1H), 5.42 (dd, J=6.4, 15.6 Hz, 1H), 4.46 (ddd, J=5.9, 7.8, 7.8 Hz, 1H), 4.12 (t, J=6.6 Hz, 1H), 3.79 (ddd, J=2.4, 5.4, 5.4 Hz, 1H), 3.41 (ddd, J=2.4, 6.3, 8.8 Hz, 1H), 3.04 (dd, J=5.9, 14.2 Hz, 1H), 2.99-2.94 (m, 2H), 2.89 (dd, J=9.3, 15.1 Hz, 1H), 2.84-2.79 (m, 2H), 2.65 (ddd, J=4.9, 6.8, 10.7 Hz, 1H), 2.27 (s, 6H), 2.22-2.14 (m, 2H); HRMS (ES+) Calcd for [C$_{33}$H$_{42}$N$_3$O$_5$]$^+$ 560.3124. Found 560.3134.

(S,S,R,R)-25: $^1$H NMR (500 MHz, CD$_3$OD) δ 7.93 (d, J=8.3 Hz, 1H), 7.23-7.13 (m, 8H), 7.03 (d, J=6.8 Hz, 2H), 6.49 (s, 2H), 5.47 (dd, J=7.3, 15.6 Hz, 1H), 5.39 (ddd, J=6.8, 6.8, 15.6 Hz, 1H), 4.46 (ddd, J=5.4, 8.3, 9.8 Hz, 1H), 4.00 (t, J=6.3 Hz, 1H), 3.54 (ddd, J=2.9, 6.8, 6.8 Hz, 1H), 3.24 (ddd, J=2.9, 5.4, 9.3 Hz, 1H), 3.17-3.10 (d, 2H), 2.86-2.78 (m, 2H), 2.75-2.66 (m, 2H), 2.51 (ddd, J=5.9, 5.9, 9.3 Hz, 1H), 2:27 (s, 6 Hz), 2.21 (t, J=6.6 Hz, 1H); HRMS (ES+) Calcd for [C$_{33}$H$_{42}$N$_3$O$_5$]$^+$560.3124. Found 560.3119.

(S,R,R,R)-25: $^1$H NMR (500 MHz, CD$_3$OD) δ 8.02 (d, J=8.3 Hz, 1H), 7.27-7.11 (m, 8H), 7.05 (d, J=6.8 Hz, 2H), 6.52 (s, 2H), 5.55-5.50 (m, 2H), 4.48 (ddd, J=4.9, 8.3, 9.3 Hz, 1H), 4.05 (t, J=4.9 Hz, 1H), 3.78 (ddd, J=2.4, 5.4, 7.8 Hz, 1H), 3.43 (ddd, J=2.4, 6.3, 8.8 Hz, 1H), 3.15 (dd, J=4.9, 13.7 Hz, 1H), 3.01 (dd, J=5.9, 14.7 Hz, 1H), 2.91-2.79 (m, 3H), 2.73 (dd, J=9.8, 13.7 Hz, 1H), 2.57 (ddd, J=5.4, 5.4, 10.3 Hz, 1H), 2.29 (s, 6H), 2.27-2.22 (m, 2H); HRMS (ES+) Calcd for [C$_{33}$H$_{42}$N$_3$O$_5$]$^+$560.3124. Found 560.3130.

(S,S,R,S)-25: $^1$H NMR (500 MHz, CD$_3$OD) δ 8.09 (d, J=8.3 Hz, 1H), 7.18-7.14 (m, 6H), 7.02 (d, J=7.3 Hz, 2H), 6.99 (d, J=7.8 Hz, 2H), 6.46 (s, 2H), 5.63 (ddd, J=7.3, 15.6 Hz, 1H), 5.43 (ddd, J=6.8, 6.8, 15.6 Hz, 1H), 4.52 (ddd, J=4.9, 8.3, 9.3 Hz, 1H), 4.12 (t, J=6.1 Hz, 1H), 3.55 (ddd, J=2.9, 6.8, 6.8 Hz, 1H), 3.26 (ddd, J=2.4, 5.4, 9.3 Hz, 1H), 3.15 (dd, J=9.8, 14.2 Hz, 1H), 3.06 (dd, J=4.4, 14.2 Hz, 1H), 2.81 (dd, J=5.4, 14.2 Hz, 1H), 2.78-2.68 (m, 3H), 2.62 (d, J=9.8 Hz, 1H), 2.30-2.24 (m, 8H); HRMS (ES+) Calcd for [C$_{33}$H$_{42}$N$_3$O$_5$]$^+$ 560.3124. Found 560.3130.

2,6-Dihydroxy-1-(4-hydroxy-2,6-dimethyl-benzyl)-7-phenethylcarbamoyl-8-phenyl-oct-4-enyl-ammonium (26): Optimized procedure: (S,R,R,R)-34 (8 mg, 0.014 mmole), EDCI.MeI (10.4 mg, 0.035 mmole), HOBT (4.7 mg, 0.035 mmole), NEt$_3$ (4.8 µL, 0.035 mmole), and phenethyl amine (4.4 µL, 0.035 mmole) were dissolved in CH$_2$Cl$_2$ (350 µL) and stirred for 16 hours. The reaction was diluted EtOAc, washed with sat. NaHCO$_3$ (aq) and brine, dried over MgSO$_4$, and concentrated under vacuum. The product was deprotected with TFA:H$_2$O:TIS (95:2.5:2.5, 800 µL) for 1 hour, then concentrated under a stream of nitrogen. The residue was dissolved in MeCN/H$_2$O (1:1, 300 µL), and the product was isolated by HPLC (25 cm semiprep C18 column, 30% to 56% MeCN:H$_2$O with 0.1% TFA over 13 minutes, 2 mL/min). The product was quantified by HPLC (25 cm analytical C18 column, 0% to 60% MeCN:H$_2$O with 0.1% TFA over 15 minutes, 1.5 mL/min) based on UV absorbance at 280 nM of 2,6-dimethyltyrosine (4.4×10$^4$ mAu·s/µmole). The procedure yielded 12.2 µmole (87%) of (S,R,R,R)-26. Four other stereoisomers were synthesized by similar procedures: (S,S,S,R)-26 (6.4 µmole), (S,R,S,R)-26 (12.5 µmole), (S,S,R,R)-26 (3.9 µmole), (S,S,R,S)-26 (6.1 µmole).

(S,S,S,R)-26: $^1$H NMR (500 MHz, CD$_3$OD) δ 7.75 (t, J=5.9 Hz, 1H), 7.25-7.11 (m, 8H), 6.99 (d, J=6.8 Hz, 2H), 6.49 (s, 2H), 5.52-5.50 (m, 2H), 4.08 (d, J=5.9, 7.8 Hz, 1H), 3.53 (ddd, J=3.4, 6.3, 6.3 Hz, 1H), 3.29-3.20 (m, 2H), 3.11 (dd, J=9.3, 14.2 Hz, 1H), 3.08-3.02 (m, 1H), 2.99 (dd, J=4.4, 13.7 Hz, 1H), 2.83-2.77 (m, 2H), 2.54-2.40 (m, 3H), 2.27 (s, 6H), 2.19 (t, J=6.1 Hz, 2H); HRMS (ES+) Calcd for [C$_{32}$H$_{41}$N$_2$O$_4$]$^+$517.3066. Found 517.3070.

(S,R,S,R)-26: $^1$H-NMR (500 MHz, CD$_3$OD) δ 7.78 (t, J=5.9 Hz, 1H), 7.26-7.12 (m, 8H), 7.00 (d, J=7.3 Hz, 2H), 6.50 (s, 2H), 5.70 (ddd, J=6.8, 6.8, 15.1 Hz, 1H), 5.57 (dd, J=6.8, 15.6 Hz, 1H), 4.15 (t, J=7.3 Hz, 1H), 3.79 (ddd, J=2.4, 5.9, 8.3 Hz, 1H), 3.41 (ddd, J=2.4, 6.3, 8.8 Hz, 1H), 3.28-3.23 (m, 1H), 3.08-3.02 (m, 2H), 2.98 (dd, J=6.3, 15.1 Hz, 1H), 2.90-2.81 (m, 2H), 2.54-2.41 (m, 3H), 2.28-2.23 (m, 8H); HRMS (ES+) Calcd for [C$_{32}$H$_{41}$N$_2$O$_4$]$^+$517.3066. Found 517.3066.

(S,S,R,R)-26: $^1$H NMR (500 MHz, CD$_3$OD) δ 7.71 (t, J=5.6 Hz, 1H), 7.26-7.12 (m, 8H), 7.03 (d, J=7.3 Hz, 2H), 6.49 (s, 2H), 5.55 (ddd, J=6.8, 6.8, 15.1 Hz, 1H), 5.49 (dd, J=7.3, 15.6 Hz, 1H), 4.09 (t, J=7.1 Hz, 1H), 3.58 (ddd, J=2.9, 6.3, 6.3 Hz, 1H), 3.34-3.25 (m, 2H), 3.17-3.10 (m, 2H), 2.82 (dd, J=5.9, 14.2 Hz, 1H), 2.72-2.70 (m, 2H), 2.56 (ddd, J=5.9, 7.8, 13.7 Hz, 1H), 2.50-2.43 (m, 2H), 2.29-2.24 (m, 8H); HRMS (ES+) Calcd for [C$_{32}$H$_{41}$N$_2$O$_4$]$^{+517.3066}$. Found 517.3077.

(S,R,R,R)-26: $^1$H NMR (500 MHz, CD$_3$OD) δ 7.79 (t, 5.9 Hz, 1H), 7.26-7.13 (m, 8H), 7.05 (d, J=7.3 Hz, 2H), 6.52 (s, 2H), 5.65 (ddd, J=6.8, 6.8, 15.6 Hz, 1H), 5.57 (dd, J=7.3, 15.6 Hz, 1H), 4.14 (t, J=7.1 Hz, 1H), 3.82 (ddd, J=2.4, 5.4, 7.8 Hz, 1H), 3.45 (ddd, J=2.4, 8.8, 8.8 Hz, 1H), 3.35-3.31 (m, 1H), 3.19-3.13 (m, 1H), 3.03 (dd, J=5.9, 15.1 Hz, 1H), 2.90 (dd, J=9.3, 15.1 Hz, 1H), 2.83-2.75 (m, 2H), 2.60-2.46 (m, 3H), 2.34-2.27 (m, 8H); HRMS (ES+) Calcd for [C$_{32}$H$_{41}$N$_2$O$_4$]$^+$ 517.3066. Found 517.3059.

(S,S,R,S)-26: $^1$H NMR (500 MHz, CD$_3$OD) δ 7.69 (t, J=5.9 Hz, 1H), 7.26-7.12 (m, 8H), 6.98 (d, J=6.8 Hz, 2H), 6.45 (s, 2H), 5.54-5.48 (m, 2H), 4.06 (t, J=6.8 Hz, 1H), 3.49 (ddd, J=3.4, 5.9, 8.3 Hz, 1H), 3.29-3.25 (m, 2H), 3.12 (dd, J,=9.8, 14.2 Hz, 1H), 2.99-2.93 (m, 2H), 2.82-2.77 (m, 2H), 2.55-2.41 (m, 3H), 2.26 (s, 6H), 2.23-2.20 (m, 1H), 2.15 (ddd, J=5.4, 5.4, 14.2 Hz, 1H); HRMS (ES+) Calcd for [C$_{32}$H$_{41}$N$_2$O$_4$]$^+$517.3066. Found 517.3057.

Dihydroxy-1-(4-hydroxy-2,6-dimethyl-benzyl)-7-(1-hydroxymethyl-2-phenyl-ethylcarbamoyl)-8-phenyl-oct-4-enyl-ammonium ((S,S,S,R)-27): (S,S,S,R)-34 (5.7 mg, 0.010 mmole), EDCI.MeI (5.9 mg, 0.020 mmole), HOBT (5.4 mg, 0.040 mmole), NEt$_3$ (2.8 µL, 0.020 mmole), and phenylalanol (3.0 mg, 0.020 µmole) were dissolved in CH$_2$Cl$_2$ (200 µL) and stirred for 16 hours. The reaction was diluted EtOAc, washed with 1 N HCl (aq), water, sat. NaHCO$_3$ (aq) and brine, dried over MgSO$_4$, and concentrated under vacuum. The product was deprotected with TFA:H$_2$O:TIS (95:2.5:2.5, 800 µL) for 1 hour, then concentrated under a stream of nitrogen. The residue was dissolved in MeCN:H$_2$O (1:1, 300 µL), and the product was isolated by HPLC (25 cm semiprep C18 column, 20% to 46% MeCN:H$_2$O with 0.1% TFA over 13 minutes, 2 mL/min). The product was quantified with the same method as for 26. The procedure yielded 5.1 μmole of (S,S,S,R)-27 (51%).

(S,S,S,R)-27: $^1$H NMR (500 MHz, CD$_3$OD) δ 7.52 (d, J=8.3 Hz, 1H), 7.23-7.10 (m, 10H), 6.50 (s, 2H), 5.54 (ddd, J=6.3, 6.3, 15.6 Hz, 1H), 5.34 (dd, J=6.3, 15.6 Hz, 1H), 4.05 (t, J=6.8 Hz, 1H), 3.94-3.90 (m, 1H), 3.52 (ddd, J=3.4, 6.3, 6.3 Hz, 1H), 3.24 (ddd, J=3.4, 5.9, 9.3 Hz, 1H), 3.19 (dd, J=4.4, 10.7 Hz, 1H), 3.09 (dd, J=9.3, 14.2 Hz, 1H), 3.04 (dd, J=5.9, 10.7 Hz, 1H), 2.94 (dd, J=4.4, 13.2 Hz, 1H), 2.84-2.74 (m, 3H), 2.55 (dd, J=8.3, 14.2 Hz, 1H), 2.50 (ddd, J=4.9, 7.3, 11.7 Hz, 1H), 2.28 (s, 6H), 2.11 (t, J=6.8 Hz, 2H); HRMS (ES+) Calcd for [C$_{33}$H$_{43}$N$_2$O$_5$]$^+$547.3172. Found 547.3166.

2,6-Dihydroxy-1-(4-hydroxy-2,6-dimethyl-benzyl)-7-phenethyloxycarbonyl-8-phenyl-oct-4-enyl-ammonium ((S,S,S,R)-28): (S,S,S,R)-34 (5.7 mg, 0.010 mmole), EDCI.MeI (5.9 mg, 0.020 mmole), DMAP (2.4 mg, 0.020 mmole, and phenethyl alcohol (12 μL, 0.10 mmole) were dissolved in CH$_2$Cl$_2$ (200 μL) and stirred for 16 hours. The reaction was diluted EtOAc, washed with 1 N HCl (aq), water, sat. NaHCO$_3$ (aq) and brine, dried over MgSO$_4$, and concentrated under vacuum. The product was deprotected with TFA:H$_2$O:TIS (95:2.5:2.5, 800 μL) for 1 hour, then concentrated under a stream of nitrogen. The residue was dissolved in MeCN:H$_2$O (1:1, 300 μL), and the product was isolated by HPLC (25 cm semiprep C18 column, 30% to 60% MeCN:H$_2$O with 0.1% TFA over 15 minutes, 2 mL/min). The product was quantified with the same method as for 26. The procedure yielded 2.1 μmole of (S,S,S,R)-28 (21%).

(S,S,S,R)-28: $^1$H NMR (500 MHz, CD$_3$OD) δ 7.23-7.05 (m, 10H), 6.51 (s, 2H), 5.43 (dd, J=7.3, 15.6 Hz, 1H), 5.23 (ddd, J=7.3, 7.3, 15.6 Hz, 1H), 4.09-4.03 (m, 2H), 3.95 (ddd, J=6.3, 6.3, 11.2 Hz, 1H), 3.46 (ddd, J=2.9, 6.8, 6.8 Hz, 1H), 3.27 (ddd, J=2.9, 5.4, 8.8 Hz, 1H), 3.12 (dd, J=9.8, 14.2 Hz, 1H), 3.01 (dd, J=3.9, 13.2 Hz, 1H), 2.83-2.62 (m, 5H), 2.28 (s, 6H), 2.13 (t, J=6.8 Hz, 1H); HRMS (ES+) Calcd for [C$_{32}$H$_{40}$NO$_5$]$^+$518.2906. Found 518.2902.

7-(1-Carbamoyl-2-phenyl-ethoxycarbonyl)-2,6-dihydroxy-1-(4-hydroxy-2,6-dimethyl-benzyl)-8-phenyl-oct-4-enyl-ammonium ((S,S,S,R)-29): (S,S,S,R)-34 (5.7 mg, 0.010 mmole), EDCI.MeI (5.9 mg, 0.020 mmole), DMAP (2.4 mg, 0.020 mmole, and (S)-2-Hydroxy-3-phenyl-propionamide (33 mg, 0.20 mmole) were dissolved in CH$_2$Cl$_2$ (200 μL) with a small amount of DMF and stirred for 16 hours. The reaction was worked up, and the product was deprotected, purified, and quantified with the same procedure as for 28 to yield 2.0 μmole of (S,S,S,R)-29 (20%).

(S,S,S,R)-29: $^1$H NMR (500 MHz, CD$_3$OD) δ 7.30-7.10 (m, 8H), 6.80 (d, J=6.8 Hz, 2H), 6.50 (s, 2H), 5.57 (m, 2H), 4.97 (dd, J=4.4, 8.8 Hz, 1H), 4.21 (br s, 1H), 3.56 (ddd, J=2.9, 6.3, 6.3 Hz, 1H), 3.28 (ddd, J=2.9, 5.4, 8.8 Hz, 1H), 3.14-3.06 (m, 2H), 3.00 (dd, J=8.8, 14.2 Hz, 1H), 2.93 (q, J=9.6 Hz, 1H), 2.81 (dd, J=5.4, 14.2 Hz, 1H), 2.71-2.68 (m, 2H), 2.27 (s, 6H), 2.22 (t, J=5.6 Hz, 2H); HRMS (ES+) Calcd for [C$_{33}$H$_{41}$N$_2$O$_6$]$^+$561.2965. Found 561.2966.

Example 9

Synthesis of 2,6-Dimethyl Compound 30

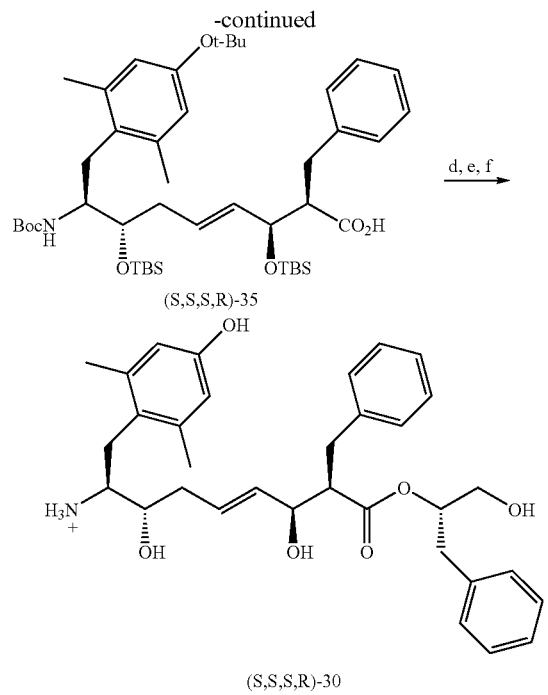

(a) Cl2(PCy3)(IMesH2)RuCHPh, CH2Cl2, 40° C; (b) TBSCl, imidazole, DMF (c) LiOH, H2O2, THF, H20, MeOH, 52%, 3 steps; (d) (S)-PhCH2(CHOH)CH2OTBS, EDCI, DMAP, CH2Cl2; (e) 48% HF (aq), MeCN; (f) 95% TFA, 23%, 3 steps.

2-Benzyl-8-tert-butoxycarbonylamino-9-(4-tert-butoxy-2,6-dimethyl-phenyl)-3,7-bis-(tert-butyl-dimethyl-silanyloxy)-non-4-enoic acid ((S,S,S,R)-35): (S,S)-32 (23 mg, 0.059 mmole) and (S,R)-33 (92 mg, 0.29 mmole) were cross metathesized by the same procedure as in the synthesis of 34 to give the cross metathesis heterodimer (26 mg, 0.039 mmole, 66%). This product was combined with TBSCl (29 mg, 0.19 mmole) and imidazole (16 mg, 0.23 mmole) in DMF (200 μL), stirred for 16 hours, then diluted with EtOAc, washed with 1 N HCl (aq), water, sat. NaHCO$_3$ (aq) and brine, dried over MgSO$_4$, and concentrated under vacuum. The residue was purified by flash chromatography (16:1 to 8:1 to 4:1 hexanes:EtOAc) to give 19 mg of di-TBS protected product (54%) and 9 mg of mono-TBS product (29%). The mono-TBS product was resubjected to give another 9 mg of di-TBS product (28 mg total, 79%). The combined di-TBS products were dissolved in 3:1 THF:MeOH (500 μL), and 30% H$_2$O$_2$ (aq) (19.6 μL, 0.19 mmole) and 1 N LiOH (aq) were added. The mixture was stirred for 5 hours, then quenched with 2N NaHSO$_3$ (aq) (186 μL), diluted with EtOAc, washed with H$_2$O and brine, dried over MgSO$_4$, filtered, and concentrated under vacuum to give 25 mg of (S,S,S,R)-35 as an oil (52% for 3 steps).

(S,S,S,R)-35: $^1$H NMR (500 MHz, CDCl$_3$) δ 7.29-7.18 (m, 5H), 6.59 (s, 2H), 5.70-5.62 (m, 1H), 5.50 (dd, J=7.3, 15.6 Hz, 1H), 4.62 (d, J=10.3 Hz, 1H), 4.16 (t, J=7.1 Hz, 1H), 3.97 (t, J=9.8 Hz, 1H), 3.85-3.83 (m, 1H), 3.04-2.20 (m, 7H), 2.27 (s, 6H), 1.27 (s, 9H), 1.24 (s, 9H), 0.96 (s, 9H), 0.90 (s, 9H), 0.15 (s, 3H), 0.14 (s, 3H), 0.03 (s, 3H), 0.02 (s, 3H), there is also an additional set of smaller peaks, believed to be from a rotamer; MS (ES+) Calcd for [C$_{45}$H$_{76}$NO$_7$Si$_2$]$^+$798.5. Found 798.7.

7-(1-Benzyl-2-hydroxy-ethoxycarbonyl)-2,6-dihydroxy-1-(4-hydroxy-2,6-dimethylbenzyl)-8-phenyl-oct-4-enyl-ammonium ((S,S,S,R)-30): (S,S,S,R)-35 (8.0 mg, 0.010 mmole), EDCI.MeI (5.9 mg, 0.020 mmole), DMAP (2.4 mg, 0.020 mmole, and (S)-1-(tert-Butyl-dimethyl-silanyloxy)-3- phenyl-propan-2-ol (5.3 mg, 0.020 mmole) were dissolved in CH$_2$Cl$_2$ (200 µL) and stirred for 16 hours. The reaction was diluted EtOAc, washed with 1 N HCl (aq), water, sat. NaHCO$_3$ (aq) and brine, dried over MgSO$_4$, and concentrated under vacuum. The product was dissolved in MeCN (200 µL) and treated with 48% HF (aq) for 16 hours, then quenched with sat. NaHCO$_3$ (aq), diluted with EtOAc, washed with sat. NaHCO$_3$ (aq), and brine, dried over MgSO$_4$, and concentrated under vacuum. The product was deprotected, purified, and quantified with the same procedure as for 28 to yield 2.3 µmole of (S,S,S,R)-30 (23%).

(S,S,S,R)-30: $^1$H NMR (500 MHz, CD$_3$OD) δ 7.25-7.12 (m, 8H), 7.03 (d, J=7.3 Hz, 2H), 6.49 (s, 2H), 5.54 (ddd, J=6.3, 6.3, 15.6 Hz, 1H), 5.47 (dd, J=6.3, 15.2 Hz, 1H), 4.9 (1H, obscured by solvent peak), 4.15 (t, J=6.8 Hz, 1H), 3.54 (ddd, J=3.4, 6.8, 6.8 Hz, 1H), 3.37 (dd, J=5.4, 11.7 Hz, 1H), 3:3 (1H, obscured by solvent peak), 3.27 (ddd, J=3.4, 5.9, 9.3 Hz, 1H), 3.11 (dd, J=9.3, 14.2 Hz, 1H), 2.98 (dd, J=4.4, 14.2 Hz, 1H), 2.85-2.79 (m, 3H), 2.76-2.67 (m, 2H), 2.27 (s, 6H), 2.19 (t, J=6.6 Hz, 2H); HRMS (ES+) Calcd for [C$_{33}$H$_{42}$NO$_6$]$^+$ 548.3012. Found 548.3030.

Example 10

Synthesis of N-terminal Allylic Alcohol Monomers

[1-(4-tert-Butoxy-benzyl)-3-diazo-2-oxo-propyl]-carbamic acid tert-butyl ester (44): To a solution of Boc-L-tyrosine(t-Bu)-OH (20.5 g, 74.2 mmol) and N-methylmorpholine (8.16 mL, 74.2 mmol) in dry THF (120 mL) at −20° C. under argon was added isobutylchloroformate (10.13 g, 9.62 mL, 74.2 mmol) over a 3 min. period. After stirring for 20 minutes, the N-methylmorpholine hydrochloride was removed by filtration. To the resulting solution was added diazomethane (120 mmol) in diethyl ether at −20° C. After the addition, the mixture was stirred for 30 min. at −20° C. and allowed to warm to room temperature overnight. The excess diazomethane was removed by bubbling a stream of argon through the reaction mixture for 1 hour, and the solvent was removed under reduced pressure. The residue was dissolved in ethyl acetate and washed with water, 0.25 M citric acid (aq), 1 N NaHCO$_3$ (aq), and brine. After drying over anhydrous MgSO$_4$, the solvent was removed at reduced pressure, and the residue was recrystallized from hexanes to afford 22.7 g (85%) of (S)-44 as a yellow solid. (R)-44 was prepared by the same procedure starting with Boc-D-tyrosine(t-Bu)-OH.

(S)-44: $^1$H NMR (500 MHz, CDCl$_3$) δ 7.08 (d, J=8.5 Hz, 2H), 6.92 (d, J=8.5 Hz, 2H), 5.18 (br s, 1H), 5.08 (br s, 1H), 4.38 (br s, 1H), 2.97 (d, J=6.5 Hz, 2H), 1.41 (s, 9H), 1.33 (s, 9H). MS (ESI) Calcd for [C$_{19}$H$_{27}$N$_3$O$_4$Na]$^+$384. Found 384.

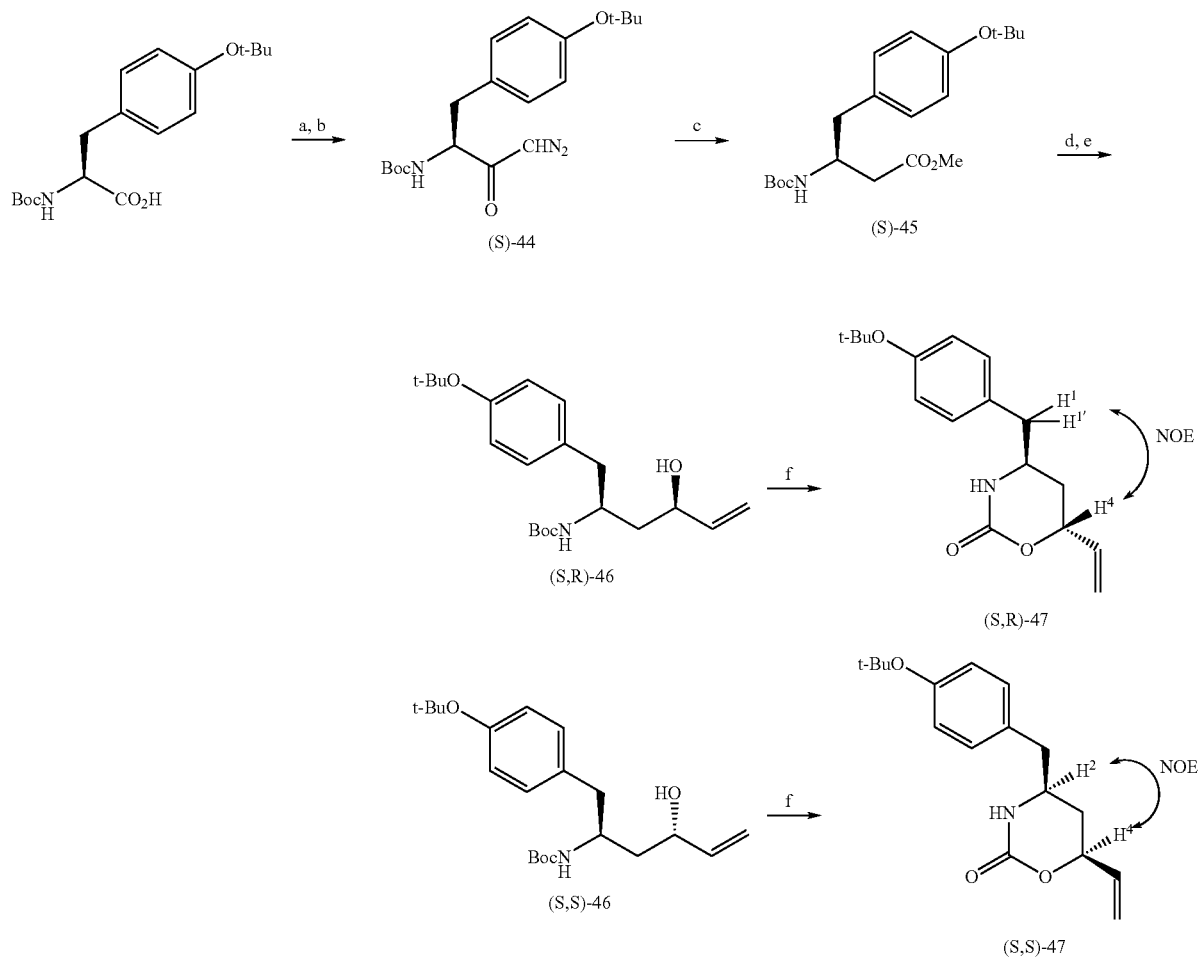

(a) ClCO2iBu, N-methylmorpholine, THF; (b) CH2N2, THF, 85% for 2 steps; (c) PhCO2Ag, NEt3, MeOH; (d) DIBAL-H, THF, 43% for 2 steps; (e) vinyl-MgBr, THF, 1.6:1 ratio of (S,R)-46 to (S,S)-46, 75%; (f) KHMDS, THF, 92-96%.

[1-(4-tert-Butoxy-benzyl)-3-oxo-propyl]-carbamic acid tert-butyl ester (45): To a solution of (s)-44 (22.7 g, 62.7 mmol) in anhydrous methanol (200 mL) was added silver benzoate (0.80 g, 3.5 mmol) in triethylamine (24 mL). The solution darkened, and rapid evolution of gas was noted. After the mixture was stirred for 30 min, additional silver benzoate (0.40 g, 1.7 mmol) in triethylamine (12 mL) was added. After an additional 45 min, celite and activated carbon were added followed by saturated NaCl solution (100 mL). After stirring for several minutes, the mixture was filtered through celite, and the filtrate was concentrated at reduced pressure. The residue was dissolved in ethyl acetate, and the resulting solution was washed with water, 1N NaHCO$_3$ (aq), 1 N HCl (aq), 1N NaHCO$_3$ (aq), and brine. After drying over Na$_2$SO$_4$, the solvent was removed at reduced pressure to afford a pale yellow oil in quantity.

To a solution of this material (11.9 g, 32.5 mmol) in toluene (78 mL) at −78° C. under argon was added DIBAL-H solution (54.2 mL, 1.5 M in toluene, 81.3 mmol) over 30 min by syringe pump. After the addition, the mixture was allowed to stir for an additional 30 min at the same temperature. Then the reaction was quenched carefully with methanol (9 mL) and allowed to warm to 0° C. Rochelle's salt (aq) 1N, 250 mL) was added to the solution, and the mixture was stirred at room temperature for 1 hour. The mixture was extracted with ether (3×100 mL), and the organic fractions were combined, washed with brine, and dried over Na$_2$SO$_4$. The solvent was removed under reduced pressure, and the residue was purified by flash chromatography (4:1 hexanes:ethyl acetate) to afford 4.7 g (43%) of (S)-45 as a colorless solid. (R)-45 was prepared by the same procedure starting with (R)-44.

(S)-45: $^1$H NMR (500 MHz, CDCl$_3$) δ 9.52 (s, 1H), 7.03 (d, J=6.5 Hz, 2H), 6.81 (d, J=7.0 Hz, 2H), 4.84 (br s, 1H), 4.21 (br s, 1H), 2.87-2.83 (m, 1H), 2.75-2.70 (m, 1H), 2.58-2.45 (m, 2H), 1.37 (s, 9H), 1.30 (s, 9H). MS (ESI) Calcd for [C$_{19}$H$_{29}$NO$_4$H]$^+$ 336. Found 336.

[1-(4-tert-Butoxy-benzyl)-3-hydroxy-pent-4-enyl]-carbamic acid tert-butyl ester (46): To a stirred solution of (S)-45 (4.64 g, 13.9 mmol) in dry THF (70 mL) at −78° C. was added dropwise vinyl magnesium bromide solution (1.0 M in THF, 50 mL, 50 mmol). The mixture was stirred for an additional 30 min. and allowed to warm up slowly to −40° C. over approximately 1 hour. The reaction was quenched with saturated NH$_4$Cl (aq) and allowed to warm to room temperature overnight. The mixture was extracted with ether (3×100 mL), and the combined organic fractions were washed with brine and dried over MgSO$_4$. The solvent was removed under reduced pressure, and the residue was purified by flash chromatography (hexanes:ethyl acetate 4:1 to hexanes:ethyl acetate 2:1) to afford 2.30 g of (S,R)-46 (46%) and 1.47 g of (S,S)-46 (29%). (R,S)-46 and (R,R)-46 were prepared by the same procedure starting with (R)-45.

(S,R)-46 $^1$H NMR (500 MHz, CDCl$_3$) δ 7.02 (d, J=7.5 Hz, 2H), 6.87 (dt, J=7.5 and 1.0 Hz, 2H), 5.81-5.72 (m, 1H), 5.16 (dd, J=17.0 and 1.5 Hz, 1H), 5.03 (d, J=10.5 Hz, 1H), 4.68 (br s, 1H), 4.15 (br s, 1H), 3.87 (br s, 1H), 2.71 (br s, 3H), 1.69-1.63 (m, 1H), 1.59-1.53 (m, 1H), 1.36 (s, 9H), 1.29 (s, 9H). MS (ESI) Calcd for [C$_{31}$H$_{33}$NO$_4$H]$^+$ 364. Found 364.

(S,S)-46' H NMR (500 MHz, CDCl$_3$) δ 7.04 (d, J=8.0 Hz, 2H), 6.90 (dd, J=8.0 and 3.5 Hz, 2H), 5.87-5.80 (m, 1H), 5.26 (d, J=17.0 Hz, 1H), 5.04 (dd, J=10.8 and 0.9 Hz, 1H), 4.62 (br s, 1H), 4.16 (br s, 1H), 4.11-4.04 (m, 1H), 3.96 (br s, 1H), 2.95-2.70 (m, 3H), 1.61-1.58 (m, 1H), 1.38 (s, 9H), 1.30 (s, 9H). MS (ESI) Calcd for [C$_{31}$H$_{33}$NO$_4$H]$^+$ 364. Found 364.

4-(4-tert-Butoxy-benzyl)-6-vinyl-[1,3]oxazinan-2-one (47): To a solution of 46 (20.0 mg, 0.056 mmol) in dry THF (1.2 mL) under N$_2$ at room temperature was added KHMDS solution (0.5 M, 0.12 mL, 0.060 mmol). After the addition, the reaction mixture was stirred for 45 min. and diluted with ether. The solution was washed with 1 N HCl (aq), H$_2$O, saturated NaHCO$_3$ (aq), and brine and dried over Na$_2$SO$_4$. The solvent as removed under reduced pressure and the residue was purified by flash chromatography (hexanes:ethyl acetate 2:1) to afford 47 as a pale yellow oil.

(S,R)-47 (12.1 mg, 96% yield)
$^1$H NMR (500 MHz, CDCl$_3$) δ 7.06 (d, J=8.0 Hz, 2H), 6.94 (dd, J=8.0 and 1.0 Hz, 2H), 5.88-5.80 (m, 1H), 5.42 (s, 1H), 5.36 (dt, J=17.0 and 1.0 Hz, 1H), 5.28 (dd, J=10.5 and 1.0 Hz, 1H), 4.93-4.88 (m, 1H), 3.68-3.63 (m, 1H), 2.79 (dd, J=13.5 and 6.0 Hz, 1H), 2.69 (dd, J=13.5 and 8.5 Hz, 1H), 1.97-1.86 (m, 2H), 1.33 (s, 9H); NOE: Irradiate, 4.90, NOE 3.64 0%, 2.79-2.69 1.4%. HRMS (ES+) Calcd for [C$_{17}$H$_{23}$NO$_3$H]$^+$ 289.1756. Found 289.1766.

(S,S)-47 (11.6 mg, 92% yield)
$^1$H NMR (500 MHz, CDCl$_3$) δ 7.06 (d, J=8.5 Hz, 2H), 6.95 (dd, J=8.0 and 2.5 Hz, 2H), 5.90-5.83 (m, 1H), 5.49 (s, 1H), 5.38 (d, J=17.0 Hz, 1H), 5.24 (d, J=11.0 Hz, 1H), 4.72-4.68 (m, 1H), 3.74-3.68 (m, 1H), 2.81 (dd, J=14.0 and 6.0 Hz, 1H), 2.66 (dt, J=14.0 and 8.5 Hz, 1H), 2.05 (dq, J=16.5 and 1.5 Hz, 1H), 1.56 (dd, J=11.0 and 1.5 Hz, 1H), 1.33 (s, 9H); NOE: Irradiate, 4.70, NOE, 3.70 2.3%, 2.81-2.66 0%. HRMS (ES+) Calcd for [C$_{17}$H$_{23}$NO$_3$H]$^+$ 289.1756. Found 289.1765.

Example 11

Synthesis of Stereodiversified 1,4-Endiols

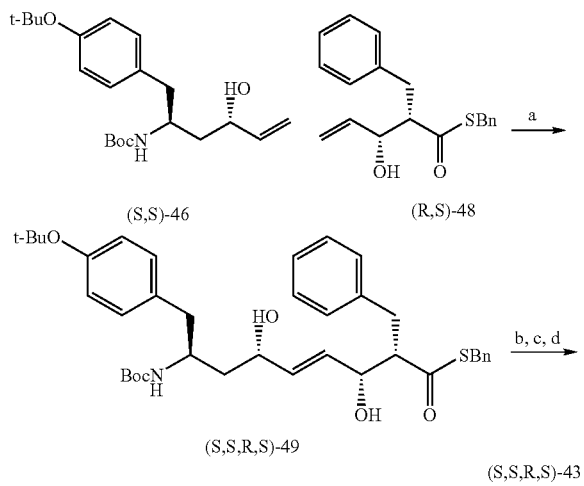

(a) Cl2(PCy3)(IMesH2)RuCHPh, CH2Cl2, 40° C., 53%; (b) LiOH, H2O2, THF, H2O, 79%; (c) HBTU, HOBt, DIPEA, NMP, Phe-NH-Rink Amide AM resin; (d) 95% TFA.

2-Benzyl-8-tert-butoxycarbonylamino-9-(4-tert-butoxy-phenyl)-3,6-dihydroxy-non-4-enethioic acid S-benzyl ester (49): 16 stereoisomers were synthesized by either of two methods:

Method A: A solution of 48 (5.0 equiv), 46 (1.0 equiv), and Cl$_2$(PCy$_3$)(IMesH$_2$)RuCHPh (0.15 equiv) in dry CH$_2$Cl$_2$ (20 mL/mmol) under argon was refluxed for 2 hours. The reaction was purified directly by flash chromatography (hexanes:ethyl acetate 2:1) to afford 49 in 30-5.6% yield on a 0.050 to 0.080 mmole scale.

Method B: To a solution of 48 (2.0 equiv), 46 (0.5 equiv), and Cl$_2$(PCy$_3$)(IMesH$_2$)RuCHPh (0.15 equiv) in dry, refluxing CH$_2$Cl$_2$ (20 mL/mmol) under argon was added 46 (0.5 equiv) in dry CH₂Cl₂ (20 mL/mmol) by syringe pump over 2 hours. After the addition, the mixture was refluxed for an additional 2 hours. The reaction was purified directly by flash chromatography (hexanes:ethyl acetate 2:1) to afford 49 in 51-81% yields on 0.075-0.10 mmol scale.

(R,R,R,S)-49: Method A 56%, Method B 81%,
¹H NMR (500 MHz, CDCl₃) δ 7.15-6.92 (m, 14H), 5.62 (dd, J=16.0 and 6.5 Hz, 1H), 5.53 (dd, J=16.0 and 6.0 Hz, 1H), 4.35 (br s, 1H), 4.25 (d, J=9.0 Hz, 1H), 3.96 (br s, 2H), 3.95 (d, J=14.5 Hz, 1H), 3.89 (d, J=14.5 Hz, 1H), 3.08-2.98 (m, 4H), 2.51 (d, J=6.5 Hz, 2H), 1.98 (br s, 1H), 1.52-1.40 (m, 2H), 1.38 (s, 9H), 1.19 (s, 9H). MS (ESI) Calcd for [C₃₈H₄₉NO₆SNa]⁺670. Found 670.

(R,R,S,R)-49: Method A 39%, Method B 53%
¹H NMR (500 MHz, CDCl₃) δ 7.15-6.98 (m, 8H), 6.92-6.85 (m, 6H), 5.92 (dd, J=15.5 and 5.5 Hz, 1H), 5.84 (dd, J=15.5 and 4.5 Hz, 1H), 4.37 (br s, 1H), 4.21-4.17 (m, 3H), 3.881-3.80 (m, 3H), 3.18-3.03 (m, 3H), 2.42 (dd, J=14.2 and 5.5 Hz, 1H), 2.35 (dd, J=14.0 and 6.5 Hz, 1H), 2.24 (br s, 1H), 1.60-1.54 (m, 1H), 1.34 (m, 10H), 1.19 (s, 9H). MS (ESI) Calcd for [C₃₈H₄₉NO₆SNa]⁺670. Found 670.

(R,R,S,S)-49: Method A 30%, Method B 51%
¹H NMR (500 MHz, CDCl₃) δ 7.18-6.90 (m, 14H), 5.67 (dd, J=15.8 and 6.0 Hz, 1H), 5.53 (dd, J=15.8 and 6.0 Hz, 1H), 4.33 (d, J=8.5 Hz, 1H), 4.30 (br s, 1H), 4.03-3.97 (m, 2H), 3.95 (d, J=14.0 Hz, 1H), 3.87 (d, J=14.0 Hz, 1H), 3.08-2.99 (m, 3H), 2.67 (br s, 1H), 2.40 (d, J=6.5 Hz, 2H), 2.13 (br s, 1H), 1.57-1.51 (m, 1H), 1.38 (m, 10H), 1.19 (s, 9H). MS (ESI) Calcd for [C₃₈H₄₉NO₆SNa]⁺670. Found 670.

(R,S,R,S)-49: Method A 30%, Method B 52%
¹H NMR (500 MHz, CDCl₃) δ 7.15-6.93 (m, 14H), 5.78 (dd, J=15.5 and 6.5 Hz, 1H), 5.66 (dd, J=15.5 and 6.0 Hz, 1H), 4.39 (br s, 1H), 4.35 (br s, 1H), 4.02 (br s, 2H), 3.85 (s, 2H), 3.18-3.11 (m, 3H), 2.62 (br s, 1H), 2.58 (d, J=5.0 Hz, 2H), 2.11 (br s, 1H), 1.59-1.52 (m, 1H), 1.40 (m, 10H), 1.20 (s, 9H). MS (ESI) Calcd for [C₃₈H₄₉NO₆SNa]⁺670. Found 670.

(R,S,S,R)-49: Method A 33%, Method B 54%
¹H NMR (500 MHz, CDCl₃) δ 7.15-6.98 (m, 10H), 6.92-6.86 (m, 4H), 5.88 (dd, J=16.5 and 5.5 Hz, 1H), 5.72 (dd, J=16.5 and 4.5 Hz, 1H), 4.31 (d, J=3.5 Hz, 1H), 4.25-4.18 (m, 3H), 3.92 (d, J=14.0 Hz, 1H), 3.85 (s, 1H), 3.84 (d, J=14.0 Hz, 1H), 3.06-2.96 (m, 3H), 2.54 (br s, 1H), 2.45-2.35 (m, 2H), 1.56-1.50 (m, 1H), 1.38 (s, 10H), 1.19 (s, 9H). MS (ESI) Calcd for [C₃₈H₄₉NO₆SNa]⁺670. Found 670.

(R,S,S,S)-49: Method A 53%, Method B 58%
¹H NMR (500 MHz, CDCl₃) δ 7.15-7.00 (m, 10H), 6.93-6.85 (m, 4H), 5.87 (dd, J=15.5 and 5.5 Hz, 1H), 5.71 (dd, J=15.5 and 4.5 Hz, 1H), 4.29 (br s, 1H), 4.20 (br s, 3H), 3.91 (d, J=14.0 Hz, 1H), 3.83 (d, J=14.0 Hz, 1H), 3.82 (br s, 1H), 3.05-2.95 (m, 3H), 2.43-2.35 (m, 3H), 1.57-1.49 (m, 1H), 1.38 (m, 10H), 1.19 (s, 9H). MS (ESI) Calcd for [C₃₈H₄₉NO₆SNa]⁺670. Found 670.

(S,R,S,S)-49: Method A 30%, Method B 62%
¹H NMR (500 MHz, CDCl₃) δ 7.15-6.97 (m, 10H), 6.91-6.86 (m, 4H), 5.85 (dd, J=15.2 and 6.0 Hz, 1H), 5.70 (dd, J=15.5 and 4.5 Hz, 1H), 4.28 (d, J=5.0 Hz, 1H), 4.20 (br s, 3H), 3.93 (d, J=14.0 Hz, 1H), 3.86 (s, 1H), 3.85 (d, J=14.0 Hz, 1H), 3.05-2.92 (m, 3H), 2.43-2.34 (m, 3H), 1.54-1.49 (m, 1H), 1.34 (m, 10H), 1.19 (s, 9H). MS (ESI) Calcd for [C₃₈H₄₉NO₆SNa]⁺670. Found 670.

(S,S,S,S)-49: Method A 40%, Method B 54%
¹H NMR (500 MHz, CDCl₃) δ 7.18-6.90 (m, 14H), 5.60 (dd, J=15.0 and 6.5 Hz, 1H), 5.49 (dd, J=15.0 and 6.5 Hz, 1H), 4.32 (br s, 1H), 4.19 (d, J=9.0 Hz, 1H), 3.96-3.93 (m, 3H), 3.88 (d, J=14.0 Hz, 1H), 3.07-2.95 (m, 4H), 2.48 (d, J=7.0 Hz, 2H), 1.75 (br s, 1H), 1.52-1.46 (m, 1H), 1.38 (m, 10H), 1.19 (s, 9H). MS (ESI) Calcd for [C₃₈H₄₉NO₆SNa]⁺670. Found 670.

2-Benzyl-8-tert-butoxycarbonylamino-9-(4-tert-butoxyphenyl)-3,6-dihydroxy-non-4-enoic acid (50): 16 stereoisomers of 50 were synthesized by the following procedure: To a solution of 0.49 (1.0 equiv) in THF (60 mL/mmol) was added 0.2 N LiOH (aq) (2.0 equiv) and 30% H₂O₂ (aq) (equal volume to LiOH (aq)). The solution was stirred for 3 h at room temperature, then acidified with 1 N HCl (aq) to pH=1 and extracted with CH₂Cl₂. The organic solution was dried over Na₂SO₄, concentrated under reduced pressure, and purified by flash chromatography to afford 50 in 64-84% yield on 0.020 to 0.030 mmol scale.

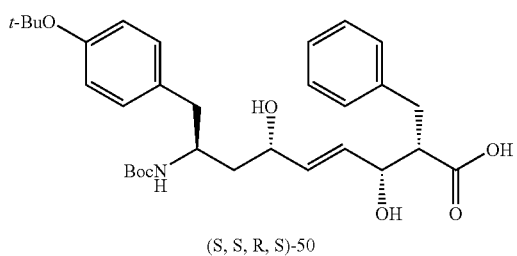

(S, S, R, S)-50

(R,R,R,S)-50: 70%
¹H NMR (500 MHz, CD₃OD) δ 7.25-7.13 (m, 5H), 6.72 (d, J=8.5 Hz, 2H), 6.86 (d, J=8.5 Hz, 2H), 5.73 (t, J=7.5 Hz, 2H), 4.20-4.18 (m, 2H), 3.92 (d, J=7.0 Hz, 1H), 2.82 (dd, J=13.0 and 4.5 Hz, 1H), 2.80-2.67 (m, 4H), 1.63-1.59 (m, 1H), 1.56-1.51 (m, 1H), 1.37 (s, 9H), 1.28 (s, 9H). MS (ESI) Calcd for [C₃₁H₄₃NO₇Na]⁺564. Found 564.

(R,R,S,S)-50: 69%
¹H NMR (500 MHz, CD₃OD) δ 7.27-6.15 (m, 5H), 7.02 (d, J=8.5 Hz, 2H), 6.75 (d, J=8.5 Hz, 2H), 5.69 (dd, J=16.0 and 7.0 Hz, 1H), 5.62 (dd, J=16.0 and 6.5 Hz, 1H), 4.19-4.11 (m, 2H), 3.77 (d, J=6.0 Hz, 1H), 2.92 (d, J=9.5 Hz, 1H), 2.74-2.65 (m, 4H), 1.73-1.67 (m, 1H), 1.64-1.59 (m, 1H), 1.37 (s, 9H), 1.27 (s, 9H). MS (ESI) Calcd for [C₃₁H₄₃NO₇Na]⁺564. Found 564.

(R,S,S,R)-50: 73%
¹H NMR (500 MHz, CD₃OD) δ 7.25-7.13 (m, 5H), 7.09 (d, J=8.0 Hz, 2H), 6.86 (d, J=8.5 Hz, 2H), 5.76-5.67 (m, 2H), 4.23 (t, J=6.5 Hz, 1H), 4.12 (d, J=7.0 Hz, 2H), 3.74 (br s, 1H), 3.05-3.00 (m, 1H), 2.88 (t, J=12.0 Hz, 1H), 2.75-2.70 (m, 2H), 2.67-2.63 (m, 1H), 1.74-1.67 (m, 1H), 1.62-1.57 (m, 1H), 1.34 (s, 9H), 1.19 (s, 9H). MS (ESI) Calcd for [C₃₁H₄₃NO₇Na]⁺564. Found 564.

(S,R,R,R)-50: 84%
¹H NMR (500 MHz, CD₃OD) δ 7.25-7.13 (m, 5H), 7.11 (d, J=8.5 Hz, 2H), 6.87 (d, J=8.5 Hz, 2H), 5.74-5.72 (m, 2H), 4.22-4.18 (m, 2H), 3.92 (t, J=2.5 Hz, 1H), 2.83 (dd, J=13.5 and 4.0 Hz, 1H), 2.78-2.66 (m, 4H), 1.64-1.53 (m, 2H), 1.37 (s, 9H), 1.28 (s, 9H). MS (ESI) Calcd for [C₃₁H₄₃NO₇Na]⁺ 564. Found 564.

(S,R,S,R)-50: 79%
¹H NMR (500 MHz, CD₃OD) δ 7.24-7.14 (m, 5H), 7.10 (d, J=8.5 Hz, 2H), 6.87 (d, J=8.5 Hz, 2H), 5.73-5.69 (m, 2H), 4.20 (t, J=6.5 Hz, 1H), 4.15 (br s, 1H), 3.90 (br s, 1H), 3.02 (dd, J=13.4 and 4.0 Hz, 1H), 2.85 (t, J=11.0 Hz, 1H), 2.72-2.60 (m, 3H), 1.61-1.57 (m, 1H), 1.58-1.49 (m, 1H), 1.34 (s, 9H), 1.19 (s, 9H). MS (ESI) Calcd for [C₃₁H₄₃NO₇Na]⁺564. Found 564.

(S,R,S,S)-50: 64%
¹H NMR (500 MHz, CD₃OD) δ 7.25-7.13 (m, 5H), 7.11 (d, J=8.5 Hz, 2H), 6.86 (d, J=8.5 Hz, 2H), 5.73 (t, J=5.0 Hz, 2H), 4.23-4.18 (m, 2H), 3.95-3.91 (m, 1H), 2.82-2.67 (m, 4H), 1.86-1.79 (m, 1H), 1.63-1.52 (m, 1H), 1.37 (s, 9H), 1.29 (s, 9H). MS (ESI) Calcd for [C₃₁H₄₃NO₇Na]⁺564. Found 564.

(S,S,R,S)-50: 79%
¹H NMR (500 MHz, CD₃OD) δ 7.27-7.15 (m, 5H), 7.02 (d, J=8.5 Hz, 2H), 6.75 (d, J=8.5 Hz, 2H), 5.69 (dd, J=15.5 and 7.0 Hz, 1H), 5.61 (dd, J=15.5 and 6.5 Hz, 1H), 4.20-4.13 (m, 2H), 3.77 (d, J=6.5 Hz, 1H), 2.92 (d, J=9.0 Hz, 1H), 2.74-2.65 (m, 4H), 1.72-1.67 (m, 1H), 1.64-1.59 (m, 1H), 1.37 (s, 9H), 1.27 (s, 9H). MS (ESI) Calcd for $[C_{31}H_{43}NO_7Na]^+$ 564. Found 564.

(S,S,S,S)-50: 68%
$^1$H NMR (500 MHz, CD$_3$OD) δ 7.25-7.13 (m, 5H), 7.09 (d, J=8.5 Hz, 2H), 6.84 (d, J=8.5 Hz, 2H), 5.71 (d, J=4.5 Hz, 2H), 4.21 (t, J=6.5 Hz, 1H), 4.15 (br s, 1H), 3.77 (br s, 1H), 2.85 (dd, J=13.0 and 4.5 Hz, 1H), 2.78-2.63 (m, 4H), 1.74-1.68 (m, 1H), 1.65-1.59 (m, 1H), 1.36 (s, 9H), 1.28 (s, 9H). MS (ESI) Calcd for $[C_{31}H_{43}NO_7Na]^+$ 564. Found 564.

7-(1-Carbamoyl-2-phenyl-ethylcarbamoyl)-3,6-dihydroxy-1-(4-hydroxy-benzyl)-8-phenyl-oct-4-enyl-ammonium (43): 16 stereoisomers of 43 were synthesized by the following procedure: To phenylalanine (6 equiv) loaded on Rink amide AM resin (0.64 mmol/g) was added 50 (1 equiv), HBTU (1 equiv), HOBT (1 equiv), and DIPEA (2 equiv) in NMP. Nitrogen was bubbled through the mixture for 90 min. The resin was washed with NMP (3×3 min), i-PrOH (3×3 min), CH$_2$Cl$_2$ (3×3 min), and Et$_2$O (3×3 min) and dried under vacuum. The product was cleaved from the resin and deprotected with TFA:TIS:H$_2$O (95:2.5:2.5) for 1.5 h, and the final product was isolated by HPLC (25 cm Beckman Ultrasphere ODS column, linear gradient of 20-100% acetonitrile/H$_2$O with 0.1% formic acid over 20 minutes, monitored by UV at 220 nm and 276 nm) to give 43 in 1-38% yield on 0.013-0.022 mmole scale. The products were quantified by HPLC based on UV absorbance at 276 nm compared to Tyr-Ot-Bu absorbance.

(R,R,R,R)-43 12%
$^1$H NMR (500 MHz, CD$_3$OD) δ 7.96 (d, J=8.0 Hz, 1H), 7.25-7.12 (m, 8H), 7.08-7.03 (m, 4H), 6.77 (d, J=8.5 Hz, 2H), 5.65 (dd, J=15.5 and 6.5 Hz, 1H), 5.56 (dd, J=15.5 and 6.0 Hz, 1H), 4.51-4.46 (m, 1H), 4.22-4.17 (m, 1H), 4.08 (d, J=6.5 Hz, 1H), 3.54-3.49 (m, 1H), 3.14 (dd, J=14.0 and 5.0 Hz, 1H), 2.87-2.68 (m, 5H), 2.59-2.54 (m, 1H), 1.77 (dt, J=18.0 and 3.5 Hz, 1H), 1.61-1.53 (m, 1H). MS (ES+) Calcd for $[C_{31}H_{37}N_3O_5H]^+$ 532.0. Found 532.3.

(R,R,R,S)-43 38%
$^1$H NMR (500 MHz, CD$_3$OD) δ 8.03 (d, J=8.0 Hz, 1H), 7.17-7.12 (m, 6H), 7.08-7.04 (m, 4H), 7.00-6.98 (m, 2H), 6.77 (d, J=8.0 Hz, 2H), 5.72 (dd, J=15.5 and 7.0 Hz, 1H), 5.58 (dd, J=15.5 and 7.0 Hz, 1H), 4.50-4.45 (m, 1H), 4.23-4.19 (m, 1H), 4.14 (t, J=7.5 Hz, 1H), 3.53 (d, J=7.5 Hz, 1H), 2.96 (dd, J=14.5 and 5.5 Hz, 1H), 2.87-2.76 (m, 4H), 2.73-2.67 (m, 2H), 1.76 (dt, J=15.0 and 3.0 Hz, 1H), 1.63-1.56 (m, 1H). HRMS (ES+) Calcd for $[C_{31}H_{37}N_3O_5H]^+$ 532.2811. Found 532.2808.

(R,R,S,R)-43 19%
$^1$H NMR (500 MHz, CD$_3$OD) δ 7.88 (d, J=7.5 Hz, 1H), 7.28-7.16 (m, 6H), 7.12-7.08 (m, 4H), 6.80 (d, J=8.5 Hz, 2H), 5.64 (dd, J=16.0 and 5.5 Hz, 1H), 5.54 (dd, J=16.0 and 5.5 Hz, 1H), 4.47 (q, J=7.5 Hz, 1H), 4.16-4.12 (m, 2H), 3.53 (q, J=8.0 Hz, 1H), 3.05 (dd, J=13.5 and 6.0 Hz, 1H), 2.95-2.66 (m, 6H), 1.80 (t, J=6.0 Hz, 1H), 1.63-1.56 (m, 1H). MS (ES+) Calcd for $[C_{31}H_{37}N_3O_5H]^+$ 532.0. Found 532.3.

(R,R,S,S)-43 11%
$^1$H NMR (500 MHz, CD$_3$OD) δ 8.54 (s, 1H), 7.16-7.12 (m, 6H), 7.04-7.01 (m, 4H), 6.97 (dd, J=8.5 and 3.5 Hz, 2H), 5.74-5.69 9m, 2H), 4.51 (q, J=5.0 Hz, 1H), 4.41 (d, J=5.5 Hz, 1H), 4.13 (t, J=7.0 Hz, 1H), 3.44 (br s, 1H), 3.04 (dd, J=14.5 and 4.5 Hz, 1H), 2.77-2.60 (m, 6H), 1.75-1.71 (m, 2H). MS (ES+) Calcd for $[C_{31}H_{37}N_3O_5H]^+$ 532.0. Found 532.4.

(R,S,R,R)-43 29%
1H NMR (500 MHz, CD$_3$OD) δ 7.29-7.17 (m, 8H), 7.11-7.06 (m, 4H), 6.78 (dt, J=7.5 and 3.0 Hz, 2H), 5.72 (dd, J=14.5 and 6.5 Hz, 1H), 5.57 (dd, J=14.5 and 1.5 Hz, 1H), 4.53 (q, J=5.0 Hz, 1H), 4.41-4.38 (m, 1H), 4.13 (t, J=5.5 Hz, 1H), 3.58 (dd, J=7.0 and 5.0 Hz, 1H), 3.19 (dd, J=14.0 and 5.0 Hz, 1H), 2.91-2.70 (m, 5H), 2.69-2.58 (m, 1H), 1.81-1.77 (m, 2H). MS (ES+) Calcd for $[C_{31}H_{37}N_3O_5H]^+$ 532.0. Found 532.4.

(R,S,R,S)-43 9%
$^1$H NMR (500 MHz, CD$_3$OD) δ 8.02 (d, J=8.5 Hz, 1H), 7.23-7.16 (m, 6H), 7.11-7.07 (m, 4H), 7.01 (dd, J=8.5 and 2.0 Hz, 1H), 6.79 (dt, J=8.3 and 3.0 Hz, 2H), 5.83 (dd, J=15.5 and 5.0 Hz, 1H), 5.63 (dd, J=16.5 and 4.5 Hz, 1H), 4.60-4.55 (m, 1H), 4.43 (d, J=5.5 Hz, 1H), 4.24 (t, J=6.5 Hz, 1H), 3.62 (t, J=6.5 Hz, 1H), 3.02 (dd, J=14.0 and 5.0 Hz, 1H), 2.91-2.70 (m, 6H), 1.80 (t, J=5.5 Hz, 2H). MS (ES+) Calcd for $[C_{31}H_{37}N_3O_5H]^+$ 532.0. Found 532.4.

(R,S,S,R)-43 24%
$^1$H NMR (500 MHz, CD$_3$OD) δ 7.87 (d, J=7.5 Hz, 1H), 7.29-7.16 (m, 6H), 7.12-7.07 (m, 6H), 6.79 (d, J=7.5 Hz, 2H), 5.63 (dd, J=15.5 and 6.5 Hz, 1H), 5.54 (dd, J=16.0 and 5.5 Hz, 1H), 4.47-4.44 (m, 1H), 4.17-4.12 (m, 2H), 3.53 (d, J=7.0 Hz, 1H), 3.05 (dd, J=14.0 and 6.5 Hz, 1H), 2.94-2.76 (m, 5H), 2.69 (q, J=5.5 Hz, 1H), 1.81-1.72 (m, 1H), 1.64-1.58 (m, 1H). HRMS (ES+) Calcd for $[C_{31}H_{37}N_3O_5H]^+$ 532.2811. Found 532.2808.

(R,S,S,S)-43 1%
$^1$H NMR (500 MHz, CD$_3$OD) δ 7.28-7.17 (m, 8H), 7.10-7.05 (m, 4H), 6.76 (d, J=8.0 Hz, 2H), 5.74 (dd, J=16.5 and 7.0 Hz, 1H), 5.53 (dd, J=156.0 and 4.5 Hz, 1H), 4.50 (q, J=5.0 Hz, 1H), 4.37 (br s, 1H), 4.13 (t, J=6.5 Hz, 1H), 3.40 (br s, 1H), 3.08 (dd, J=13.5 and 5.0 Hz, 1 H), 2.90-2.71 (m, 5H), 2.63-2.59 (m, 1H), 1.77-1.73 (m, 2H). MS (ES+) Calcd for $[C_{31}H_{37}N_3O_5H]^+$ 532.0. Found 532.4.

(S,R,R,R)-43 5%
$^1$H NMR (500 MHz, CD$_3$OD) δ 8.57 (br s, 1H), 7.29-7.17 (m, 8H), 7.10-7.05 (m, 4H), 6.76 (d, J=8.0 Hz, 2H), 5.72 (dd, J=15.5 and 7.0 Hz, 1H), 5.55 (dd, J=16.0 and 4.5 Hz, 1H), 4.50 (q, J=5.0 Hz, 1H), 4.37 (br s, 1H), 4.13 (t, J=6.5 Hz, 1H), 3.43 (br s, 1H), 3.18 (dd, J=13.5 and 5.0 Hz, 1H), 2.90-2.71 (m, 5H), 2.63-2.59 (m; 1H), 1.74-1.70 (m, 2H). MS (ES+) Calcd. for $[C_{31}H_{37}N_3O_5H]^+$ 532.0. Found 532.4.

(S,R,R,S)-43 12%
$^1$H NMR (500 MHz, CD$_3$OD) δ 8.09 (d, J=7.5 Hz, 1H), 7.252-7.17 (m, 6H), 7.11-7.02 (m, 6H), 6.75 (d, J=8.5 Hz, 2H), 5.80 (dd, J=15.5 and 7.5 Hz, 1H), 5.60 (dd, J=16.0 and 5.5 Hz, 1H), 4.55-4.50 (m, 1H), 4.23 (q, J=5.0 Hz, 1H), 4.21 (t, J=7.0 Hz, 1H), 3.58 (t, J=6.5 Hz, 1H), 3.02 (dd, J=14.0 and 5.5 Hz, 1H), 2.91 (dd, J=14.0 and 7.5 Hz, 1H), 2.86-2.76 (m, 4H), 2.72 (dd, J=14.5 and 9.0 Hz, 1H), 1.81 (t, J=5.5 Hz, 1H). MS (ES+) Calcd for $[C_{31}H_{37}N_3O_5H]^+$ 532.0. Found 532.4.

(S,R,S,R)-43 29%
$^1$H NMR (500 MHz, CD$_3$OD) δ 7.90 (d, J=8.0 Hz, 1H), 7.24-7.07 (m, 12H), 6.81 (d, J=7.5 Hz, 2H), 5.61 (dd, J=15.0 and 7.0 Hz, 1H), 5.42 (dd, J=16.5 and 6.5 Hz, 1H), 4.52 (q, J=3.0 Hz, 1H), 4.13 (t, J=6.5 Hz, 1H), 4.07-4.02 (m, 1H), 3.51 (d, J=8.5 Hz, 1H), 3.09 (dd, J=14.0 and 5.5 Hz, 1H), 2.93-2.73 (m, 5H), 2.69-2.65 (m, 1H), 1.73 (dt, J=16.5 and 3.0 Hz, 1H), 1.60-1.54 (m, 1H). MS (ES+) Calcd for $[C_{31}H_{37}N_3O_5H]^+$ 532.0. Found 532.3.

(S,R,S,S)-43 19%
$^1$H NMR (500 MHz CD$_3$OD) δ 8.11 (d, J=8.0 Hz, 1H), 7.20-7.15 (m, 6H), 7.08 (d, J=8.5 Hz, 2H), 7.05-7.10 (m, 4H), 6.76 (dd, J=8.0 and 3.0 Hz, 2H), 5.77-5.68 (m, 2H), 4.57-4.52 (m, 1H), 4.45 (dd, J=10.0 and 5.0 Hz, 1H), 4.16 (t, J=5.5 Hz, 1H), 3.58 (t, J=6.5 Hz, 1H), 3.06 (dd, J=14.5 and 5.0 Hz, 1H), 2.92 (dd, J=14.0 and 6.5 Hz, 1H), 2.85-2.72 (m, 3H), 2.67-2.61 (m, 2H), 1.82-1.79 (m, 2H). MS (ES+) Calcd for $[C_{31}H_{37}N_3O_5H]^+$ 532.0. Found 532.3.

(S,S,R,R)-43 13%

¹H NMR (500 MHz, CD₃OD) δ 7.27-7.14 (m, 8H), 7.11-7.05 (m, 4H), 6.80 (dd, J=7.0 and 2.0 Hz, 2H), 5.64 (dd, J=15.5 and 6.5 Hz, 1H), 5.54 (dd, J=16.0 and 6.5 Hz, 1H), 4.52 (q, J=5.0 Hz, 1H), 4.21-4.16 (m, 1H), 4.09 (t, J=6.5 Hz, 1H), 3.53 (d, J=8.5 Hz, 1H), 3.17 (dd, J=14.0 and 5.5 Hz, 1H), 2.89-2.71 (m, 5H), 2.62-2.56 (m, 1H), 1.77 (dt, J=14.5 and 3.5 Hz, 1H), 1.64-1.56 (m, 1H). MS (ES+) Calcd for $[C_{31}H_{37}N_3O_5H]^+$ 532.0. Found 532.4.

(S,S,R,S)-43 6%

¹H NMR (500 MHz, CD₃OD) δ 8.02 (d, J=8.0 Hz, 1H), 7.17-7.13 (m, 6H), 7.08-7.04 (m, 4H), 6.99 (dd, J=7.5 and 0.9 Hz, 2H), 6.76 (dd, J=7.0 and 1.2 Hz, 2H), 5.72 (dd, J=15.5 and 7.0 Hz, 1H), 5.58 (dd, J=15.5 and 7.0 Hz, 1H), 4.52-4.49 (m, 1H), 4.23-4.20 (m, 1H), 4.14 (t, J=7.0 Hz, 1H), 3.53-3.49 (m, 1H), 2.96 (dd, J=14.0 and 5.0 Hz, 1H), 2.83-2.66 (m, 6H), 1.79 (dt, J=14.5 and 3.0 Hz, 1H), 1.63-1.56 (m, 1H). MS (ES+) Calcd for $[C_{31}H_{37}N_3O_5H]^+$ 532.0. Found 532.4.

(S,S,S,R)-43 8%

¹H NMR (500 MHz, CD₃OD) δ 7.91 (d, J=8.0 Hz, 1H), 7.26-7.09 (m, 12H), 6.81 (d, J=7.5 Hz, 2H), 5.61 (dd, J=15.0 and 7.0 Hz, 1H), 5.44 (dd, J=15.5 and 6.0 Hz, 1H), 4.52 (q, J=3.0 Hz, 1H), 4.13 (t, J=6.5 Hz, 1H), 4.07-4.02 (m, 1H), 3.53 (d, J=9.0 Hz, 1H), 3.09 (dd, J=14.0 and 5.5 Hz, 1H), 2.93-2.73 (m, 5H), 2.69-2.65 (m, 1H), 1.73 (dt, J=18.0 and 3.0 Hz, 1H), 1.62-1.56 (m, 1H). MS (ES+) Calcd for $[C_{31}H_{37}N_3O_5H]^+$ 532.0. Found 532.4.

(S,S,S,S)-43 11%

¹H NMR (500 MHz, CD₃OD) δ 7.29-7.17 (m, 8H), 7.11-7.06 (m, 4H), 6.78 (dt, J=7.5 and 3.0 Hz, 2H), 5.72 (dd, J=14.5 and 6.5 Hz, 1H), 5.57 (dd, J=14.5 and 1.5 Hz, 1H), 4.53 (q, J=5.0 Hz, 1H), 4.41-4.38 (m, 1H), 4.13 (t, J=5.5 Hz, 1H), 3.58 (dd, J=7.0 and 5.0 Hz, 1H), 3.19 (dd, J=14.0 and 5.0 Hz, 1H), 2.91-2.70 (m, 5H), 2.69-2.58 (m, 1H), 1.81-1.77 (m, 2H). MS (ES+) Calcd for $[C_{31}H_{37}N_3O_5H]^+$ 532.0. Found 532.4.

Opioid Receptor Binding Assays

For selected compounds, $K_i$ for MOR, DOR, and KOR were determined according to the following procedure: Recombinant hMOR-1 membrane preps from stably transfected CHO cells and recombinant hDOR-1 membrane preps from stably transfected HEK-293 cells were purchased from Amersham Biosciences. Guinea pig cerebellum preparations were used for KOR assays. [Tyrosyl-3,5-³H(N)]-DAMGO (50 Ci/mmole) and [tyrosyl-2,6-³H(N)]-DPDPE (35 Ci/mmole) were purchased from PerkinElmer Life Sciences.

Compound 1

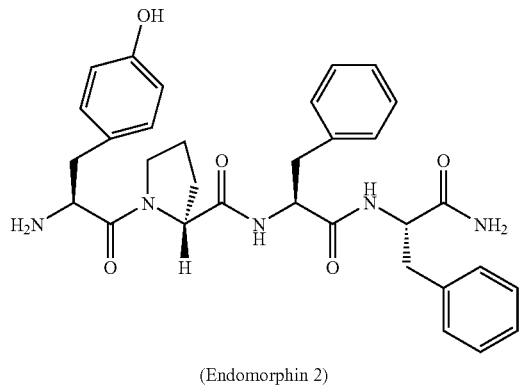

(Endomorphin 2)

and naloxone hydrochloride were purchased from SigmaAldrich.

In each microassay, an experimental compound at a given concentration was incubated with 1 nM of radioligand (3H-DAMGO for MOR, ³H-DPDPE for DOR, and ³H-U-69,593 for KOR) and about 0.04 nM opioid receptor in 200 μL of assay buffer (50 mM potassium hydrogen phosphate, pH 7.4, 5 mM MgCl₂) in a 96-well plate (Corning 3600, polystyrene with non-binding surface) for 1 hour at room temperature. Each microassay from an assay plate was filtered through an individual well of a Packard GF/B 96-well filter plate (glass fiber filter) to collect the membranes. Each well was washed twice with 200 μL of ice cold wash buffer (50 mM Tris, pH 7.4). The filter plate was allowed to dry overnight, the back was sealed, and Packard Bioscience Microscint PS scintillation fluid (75 μL) was added to each well, which was then counted for ³H for 2 minutes using a Packard Bioscience TopCount scintillation counter plate reader.

Each compound was assayed at 8 concentrations, using half-log serial dilutions. Each concentration was tested in triplicate, and the ³H cpm were averaged. The results were fit to the following equation using a non-linear regression performed by Kaleidagraph software to determine the IC₅₀ for each compound:

$$\text{cpm} = \text{min} + (\text{max}-\text{min})/(1+10^{\log[\text{compound}]-\log(IC50)})$$

where cpm=³H counts per minute for a microassay log[compound]=log₁₀ of the concentration of the compound in the microassay log(IC50)=log₁₀ of the $IC_{50}$ min=non-specific binding (verified by controls with 10 μM naloxone)

max=total binding (maximum binding, verified by blanks with no cold ligand)

The $K_i$ for each compound was calculated using the following equation:

$$K_i = IC_{50}/(1+[\text{radioligand}]/K_d)$$

Where $K_i$=the competition binding constant for the experimental compound $IC_{50}$=the experimental $IC_{50}$ for the compound

[radioligand]=concentration of radioligand (3H-DAMGO for MOR, ³H-DPDPE for DOR) used in the competition experiment. This concentration was determined experimentally by scintillation counting an aliquot of the radioligand stock solution used in the assay.

$K_d$=the binding constant for the radioligand. $K_d$ values were obtained experimentally for, ³H-DAMGO (0.29 nM) and ³H-DPDPE (0.98 nM), using the same assay conditions.

This triplicate experiment was repeated three times for the MOR and twice for the DOR and the KOR. The $K_i$ values reported are the mean value of the replicates, and the errors reported are two standard deviations (95% confidence interval) of the mean.

Example 12

Binding Affinity for MOR

TABLE 3

| Binding affinity of compounds 1-13 for MOR | | | | | |
|---|---|---|---|---|---|
| compound | $K_i$ MOR (nM)[a,b] | | | | |
| 1 | 1.2 ± 0.1 | | | | |
| | Configuration: | | | | |
| | S,S,S,R | S,S,R,R | S,R,R,R | S,R,S,R | S,S,R,S |
| 2 | 8.8 ± 0.7 | 25 ± 5 | 67 ± 38 | 160 ± 40 | 79 ± 23 |
| 6 | 98 ± 31 | 95 ± 61 | 120 ± 30 | 190 ± 20 | |
| 9 | 370 ± 150 | 74 ± 12 | 400 ± 110 | 260 ± 70 | |
| 10 | 21 ± 1 | 29 ± 8 | 53 ± 6 | | |
| 11 | 10 ± 2 | 16 ± 1 | 28 ± 5 | | |
| 12 | 20 ± 1 | 22 ± 4 | 37 ± 1 | | |
| 13 | 37 ± 8 | | | | |

[a]Competitive binding assay with ³H-DAMGO for hMOR-1 stably transfected into CHO cells.
[b]Errors represent 95% confidence interval.

TABLE 4

Binding affinity of compounds 1 and 25-30 for MOR

| compound | $K_i$ MOR (nM)[a,b] | | | | |
|---|---|---|---|---|---|
| 1 | 0.69 ± 0.18 | | | | |
| | Configuration: | | | | |
| | S,S,S,R | S,S,R,R | S,R,R,R | S,R,S,R | S,S,R,S |
| 25 | 0.17 ± 0.07 | 0.42 ± 0.09 | 1.6 ± 0.9 | 1.2 ± 0.3 | 1.2 ± 0.4 |
| 26 | 0.29 ± 0.06 | 0.37 ± 0.13 | 0.72 ± 0.26 | 0.24 ± 0.05 | 0.64 ± 0.09 |
| 27 | 0.16 ± 0.06 | | | | |
| 28 | 0.45 ± 0.05 | | | | |
| 29 | 0.24 ± 0.03 | | | | |
| 30 | 0.44 ± 0.01 | | | | |

[a]Competitive binding assay with ³H-DAMGO for hMOR-1 stably transfected into CHO cells.
[b]Errors represent 95% confidence interval.

TABLE 5

Binding of Stereodiverse Compounds 1 and stereodiverse 43 to MOR

| compound | $K_i$ MOR[b] (nM) |
|---|---|
| endo-2 (1) | 1.0 ± 0.1 |
| (S,S,R,S)-43 | 14 ± 1 |
| (S,R,R,S)-43 | 28 ± 6 |
| (S,R,S,S)-43 | 42 ± 5 |
| (S,R,S,R)-43 | 32 ± 6 |
| (R,R,S,S)-43 | 38 ± 13 |
| (R,S,R,R)-43 | 20 ± 3 |

[b]Competitive binding assay with 3H-DAMGO for hMOR-1 stably transfected into CHO cells.

Example 13

Binding Affinity for DOR

TABLE 6

Binding affinity of compounds 1-13 for DOR

| compound | $K_i$ DOR (µM)[a,b] | | | | |
|---|---|---|---|---|---|
| 1 | 12 ± 1 | | | | |
| | Configuration: | | | | |
| | S,S,S,R | S,S,R,R | S,R,R,R | S,R,S,R | S,S,R,S |
| 2 | 0.51 ± 0.01 | 1.2 ± 0.1 | 1.4 ± 0.3 | 0.85 ± 0.03 | 6.9 ± 1.3 |
| 6 | 2.2 ± 0.3 | 3.0 ± 0.1 | 3.1 ± 0.7 | 4.0 ± 0.1 | |
| 9 | 2.2 ± 0.1 | 4.3 ± 1.4 | 9.2 ± 2.1 | 10 ± 2 | |
| 10 | 3.6 ± 0.1 | 1.2 ± 0.3 | 2.9 ± 0.6 | | |
| 11 | 1.1 ± 0.1 | 0.62 ± 0.08 | 0.96 ± 0.1 | | |
| 12 | 0.68 ± 0.04 | 0.62 ± 0.07 | 0.57 ± 0.28 | | |
| 13 | 0.91 ± 0.25 | | | | |

[a]Competitive binding assay with ³H-DAMGO for hDOR-1 stably transfected into HEK-293 cells.
[b]Errors on the measurements represent two standard deviations (95% confidence).

TABLE 7

Binding affinity of compounds 1 and 25-30 for DOR

| compound | Ki DOR (nM)[a,b] | | | | |
|---|---|---|---|---|---|
| 1 | 25,000 ± 1,000 | | | | |
| | Configuration: | | | | |
| | S,S,S,R | S,S,R,R | S,R,R,R | S,R,S,R | S,S,R,S |
| 25 | 40 ± 1 | 36 ± 6 | 85 ± 13 | 46 ± 16 | 230 ± 20 |
| 26 | 99 ± 11 | 26 ± 3 | 66 ± 1 | 123 ± 8 | 120 ± 30 |
| 27 | 54 ± 8 | | | | |
| 28 | 21 ± 4 | | | | |
| 29 | 56 ± 4 | | | | |
| 30 | 17 ± 6 | | | | |

[a]Competitive binding assay with 3H-diprenorphine for hDOR-1 stably transfected into HEK-293 cells.
[b]Effors represent two standard deviations from the mean.

TABLE 8

[a]Binding affinity of Compounds 1 and stereodiverse 43 for DOR

| compound | $K_i$ DOR[c] (μM) |
|---|---|
| endo-2 (1) | 25 ± 1 |
| (S,S,R,S)-43 | 1.2 ± 0.1 |
| (S,R,R,S)-43 | 2.5 ± 3 |
| (S,R,S,S)-43 | 2.5 ± 0.3 |
| (S,R,S,R)-43 | 0.74 ± 0.04 |
| (R,R,S,S)-43 | 1.2 ± 0.1 |
| (R,S,R,R)-43 | 2.5 ± 0.3 |

[a]errors on measurements represent two standard deviations from the mean (95% confidence interval).
[c]Competitive binding assay with $^3$H-DPN for hDOR-1 stably transfected into HEK-293 cells.

Example 14

Binding Affinity for KOR

TABLE 9

Binding affinity of compounds 1-13 for KOR

| compound | $K_i$ KOR (μM)[a,b] | | | | |
|---|---|---|---|---|---|
| 1 | 10.4 ± 8.6 | | | | |
| | Configuration: | | | | |
| | S,S,S,R | S,S,R,R | S,R,R,R | S,R,S,R | S,S,R,S |
| 2 | 1.3 ± 0.5 | 1.2 ± 0.7 | 1.2 ± 0.1 | 2.9 ± 0.8 | 1.3 ± 0.1 |
| 6 | 3.9 ± 1.7 | 0.73 ± 0.27 | 1.5 ± 0.7 | 6.6 ± 3.5 | |
| 9 | 6.1 ± 3.0 | 1.6 ± 0.1 | 5.8 ± 1.8 | 1.7 ± 0.4 | |
| 10 | 1.8 ± 0.3 | 3.4 ± 0.3 | 2.8 ± 0.6 | | |
| 11 | 6.0 ± 0.7 | 2.9 ± 0.4 | 3.4 ± 1.3 | | |
| 12 | 1.05 ± 0.01 | 0.77 ± 0.13 | 0.97 ± 0.08 | | |
| 13 | 6.0 ± 2.1 | | | | |

[a]Competitive binding assay with $^3$H-U-69,593 for KOR in guinea pig cerebellum preps.
[b]Errors on the measurements represent two standard deviations (95% confidence).

TABLE 10

Binding affinity of compounds 1 and 25-30 for KOR

| compound | $K_i$ KOR (nM)[a,b] | | | | |
|---|---|---|---|---|---|
| 1 | 10,400 ± 8,600 | | | | |
| | Configuration: | | | | |
| | S,S,S,R | S,S,R,R | S,R,R,R | S,R,S,R | S,S,R,S |
| 25 | 22 ± 9 | 21 ± 4 | 25 ± 14 | 15 ± 8 | 50 ± 16 |
| 26 | 42 ± 29 | 64 ± 14 | 69 ± 20 | 51 ± 1 | 60 ± 32 |
| 27 | 69 ± 14 | | | | |
| 28 | 130 ± 70 | | | | |
| 29 | 260 ± 220 | | | | |
| 30 | 85 ± 1 | | | | |

[a]Competitive binding assay with 3H-U-69,593 for KOR in guinea pig cerebellum preparation.
[b]Errors represent two standard deviations from the mean.

TABLE 11

[a]Binding Affinity of compounds 1 and stereodiverse 43 for KOR

| compound | $K_i$ KOR[d] (μM) |
|---|---|
| endo-2 (1) | 10.4 ± 8.6 |
| (S,S,R,S)-43 | 0.45 ± 0.06 |
| (S,R,R,S)-43 | 1.2 ± 0.6 |
| (S,R,S,S)-43 | 3.1 ± 2.6 |
| (S,R,S,R)-43 | 0.29 ± 0.1 |
| (R,R,S,S)-43 | 0.88 ± 0.55 |
| (R,S,R,R)-43 | 0.27 ± 0.03 |

[a]errors on measurements represent two standard deviations from the mean (95% confidence interval).
[d]Competitive binding assay with $^3$H-U-69,593 for KOR in guinea pig cerebellum preparation.

Example 15

Selectivity of Ligands for MOR Versus DOR and KOR

TABLE 12

Selectivity of compounds 1-13 for MOR versus DOR and KOR

| Compound | $K_i$ DOR[a]/$K_i$ MOR, $K_i$ KOR[b]/$K_i$ MOR | | | | |
|---|---|---|---|---|---|
| 1 | 10,000, 9,000 | | | | |
| | Configuration: | | | | |
| | S,S,S,R | S,S,R,R | S,R,R,R | S,R,S,R | S,S,R,S |
| 2 | 57, 150 | 45, 48 | 21, 18 | 5, 18 | 86, 16 |
| 6 | 22, 40 | 31, 8 | 26, 13 | 21, 35 | |
| 9 | 6, 16 | 58, 22 | 23, 15 | 39, 7 | |
| 10 | 170, 86 | 42, 120 | 55, 53 | | |
| 11 | 110, 600 | 39, 180 | 34, 120 | | |
| 12 | 34, 53 | 28, 35 | 15, 26 | | |
| 13 | 24, 160 | | | | |

[a]Competitive binding assay with $^3$H-DPDPE for hDOR-1 stably transfected into HEK-293 cells.
[b]Competitive binding assay with $^3$H-U-69,593 for KOR in guinea pig cerebellum preparation.

TABLE 13

Selectivity of ligands compounds 1 and 25-30 for MOR versus DOR and KOR

| Compound | $K_i$ DOR[a]/$K_i$ MOR, $K_i$ KOR[b]/$K_i$ MOR | | | | |
|---|---|---|---|---|---|
| 1 | 36,000, 15,000 | | | | |
| | Configuration: | | | | |
| | S,S,S,R | S,S,R,R | S,R,R,R | S,R,S,R | S,S,R,S |
| 25 | 230, 130 | 86, 49 | 53, 16 | 38, 13 | 190, 41 |
| 26 | 340, 140 | 70, 170 | 91, 96 | 510, 210 | 190, 94 |
| 27 | 340, 430 | | | | |
| 28 | 46, 280 | | | | |
| 29 | 230, 1,100 | | | | |
| 30 | 39, 190 | | | | |

[a]Competitive binding assay with $^3$H-DPDPE for hDOR-1 stably transfected into HEK-293 cells.
[b]Competitive binding assay with $^3$H-U-69,593 for KOR in guinea pig cerebellum preparation.

TABLE 14

[a,b,c]Selectivity of stereodiverse compounds 1 and stereodiverse 43 for MOR versus DOR and KOR

| compound | ($K_i$DOR/$K_i$MOR) | ($K_i$KOR/$K_i$MOR) |
|---|---|---|
| endo-2 (1) | 25,000 | 10,000 |
| (S,S,R,S)-43 | 82 | 32 |
| (S,R,R,S)-43 | 89 | 42 |
| (S,R,S,S)-43 | 60 | 74 |
| (S,R,S,R)-43 | 23 | 9 |
| (R,R,S,S)-43 | 30 | 23 |
| (R,S,R,R)-43 | 125 | 14 |

Competitive binding assay with $^3$H-DAMGO for hMOR-1 stably transfected into CHO cells. Competitive binding assay with $^3$H-DPN for hDOR-1 stably transfected into HEK-293 cells. Competitive binding assay with $^3$H-U-69,593 for KOR in guinea pig cerebellum preparation.

Example 16

Binding of 2 to MOR

Compounds 2 and compound 1 (Endomorphin-2) were screened at 10 μM for [15,16-$^3$H]-diprenorphine displacement from hMOR-1 stably transfected into CHO cells with endomorphin-2 (1) as a control. Specific binding is defined by the difference between compound 1 and a blank. The results are shown in FIG. 1.

Example 17

Binding of 43 to MOR

Compounds 1 and stereodiverse 43 were screened for MOR affinity at 1 μM concentration in a competitive binding assay with $^3$H-DAMGO. The stereoisomers of 43 showed varying degrees of affinity for MOR, displacing 28-90% of $^3$H-DAMGO from MOR FIG. 2. shows the results of a competitive binding assay of compound 43 with 3H-DAMGO (1.3 nM) for hMOR-1 stably transfected into CHO cells. Specific binding was defined by the difference in radioligand bound between assays with no ligand (blank) and with 10 mM naloxone. Error bars represent 2 standard deviations from the mean (95% confidence interval) on triplicate measurements.

Example 18

MOR Activation

MOR GTP-Y—S assay was run in the same 200 μL, 96 well format as the binding assay. Each microassay contained experimental compound, 0.04 nM GTP-γ-$^{35}$S, 9 μM GDP, and about 0.02 nM MOR (from stably transfected CHO cells), in assay buffer (50 mM Tris-HCl, 3 mM MgCl$_2$, 0.2 mM EGTA, 100 mM NaCl, pH 7.4). The assays were incubated for two to three hours at room temperature, then filtered onto a filter plate. The plate was dried; scintillation fluid was added, and the wells were counted for $^{35}$S. Blank assays were run to determine non-specific binding. DAMGO, 1, 25-30, and stereodiverse 43 were each assayed at 10 μM in quadruplicate. The results were averaged; the non-specific counts were subtracted, and the resulting value was expressed as a percent of the value obtained for DAMGO. The error reported is two standard deviations from the mean of the quadruplicate experiment. The values were compared using one way Anova with Tukey's post-hoc analysis. The results are shown in Tables 15 and 16 below.

TABLE 15

MOR activation with compounds 1 and 25-30

| compound | % GTP-γ-$^{35}$S bound[a,b] | | | | |
|---|---|---|---|---|---|
| 1 | 100 ± 6 | | | | |
| | Configuration: | | | | |
| | S,S,S,R | S,R,S,R | S,S,R,R | S,R,R,R | S,S,R,S |
| 25 | 35 ± 5 | 14 ± 3 | 75 ± 11 | 43 ± 9 | 32 ± 5 |
| 26 | 40 ± 3 | 49 ± 4 | 48 ± 9 | 27 ± 9 | 52 ± 6 |
| 27 | 44 ± 6 | | | | |
| 28 | 47 ± 5 | | | | |

TABLE 15-continued

MOR activation with compounds 1 and 25-30

| 29 | 79 ± 5 |
| 30 | 62 ± 4 |

[a] Specific binding of GTP-g-$^{35}$S by G-proteins in CHO membrane preparations stably transfected with hMOR-1, in the presence of GDP and 1 or 25-30 (10 mM), expressed as a percentage of DAMGO induced GTP-g-$^{35}$S specific binding.
[b] Errors represent two standard deviations from the mean.

TABLE 16

MOR activation with compounds 1 and stereodiverse 43.

| compound | % GTP-γ-S bound[e] |
|---|---|
| endo-2 (1) | 100 ± 6 |
| (S,S,R,S)-43 | 25 ± 5 |
| (S,R,R,S)-43 | 48 ± 8 |
| (S,R,S,S)-43 | 57 ± 12 |
| (S,R,S,R)-43 | 37 ± 7 |
| (R,R,S,S)-43 | 30 ± 6 |
| (R,S,R,R)-43 | 68 ± 10 |

[e] Specific binding of GTP-γ-$^{35}$S by G-proteins in CHO membrane preparations stably transfected with hMOR-1, in the presence of GDP and 1 or 43 (10 μM), expressed as a percentage of DAMGO induced GTP-γ-$^{35}$S specific binding.

Figure 3:
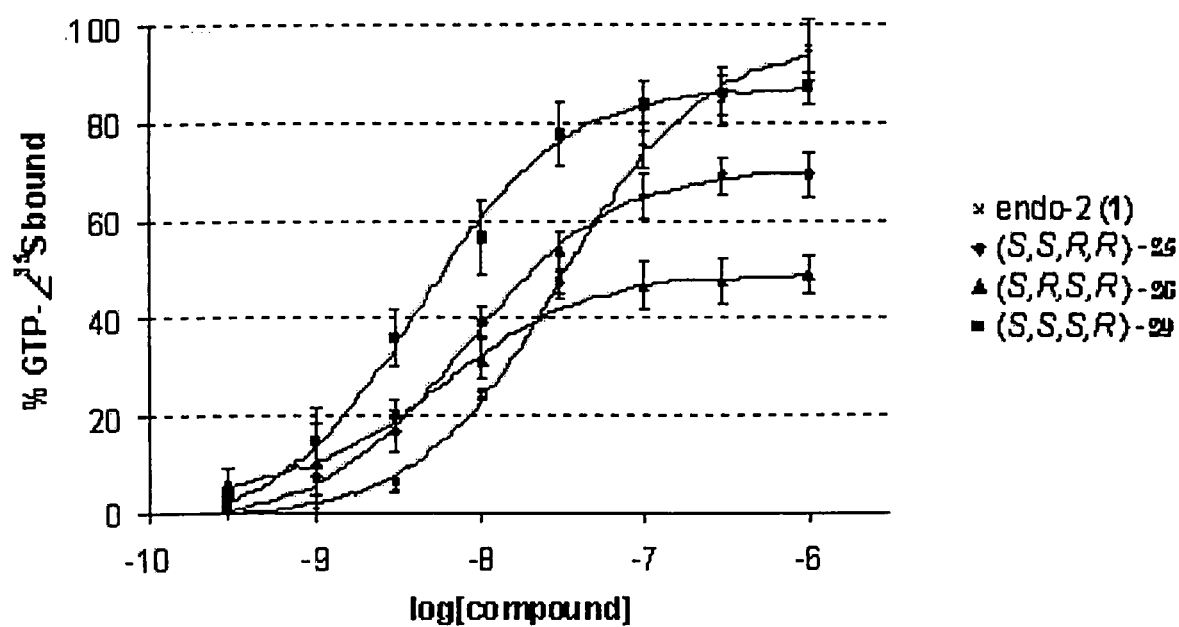
FIG. 3 depicts a graph used in the determination of $EC_{50}$ values for Compounds 1, (S,S,R,R)-25, (S,R,S,R)-26, and (S,S,S,R)-29 using non-linear regression.

Compounds 1, (S,S,R,R)-25, (S,R,S,R)-26, and (S,S,S,R)-29 were assayed at eight concentrations (half-log dilutions) in triplicate. The $EC_{50}$ value was calculated using a non-linear regression, and the error reported is the standard error on the regression value. The results are shown in FIG. 3.

Figure 4:
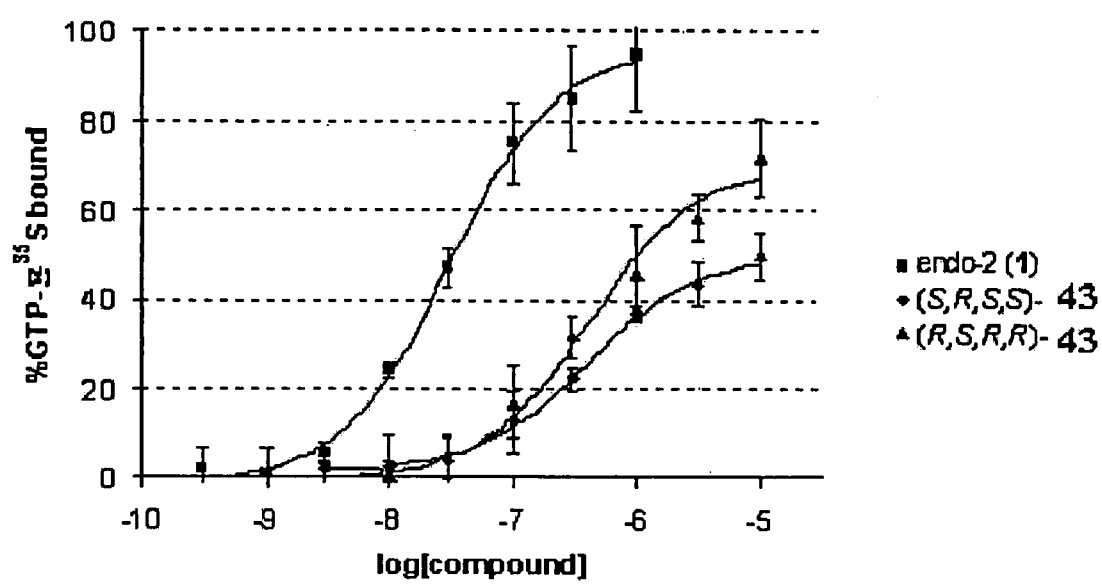
FIG. 4 depicts a graph used in the determination of $EC_{50}$ values for Compounds 1, (R,S,R,R)-43 and (S,R,S,S)-43 using non-linear regression.

Additionally, (R,S,R,R)-43 and (S,R,S,S)-43, were assayed at eight concentrations (half-log dilutions) in triplicate. The $EC_{50}$ value was calculated using a non-linear regression, and the error reported is the standard error on the regression value. The results are shown in FIG. 4.

All references cited herein, whether in print, electronic, computer readable storage media or other form, are expressly incorporated by reference in their entirety, including but not limited to, abstracts, articles, journals, publications, texts, treatises, internet web sites, databases, patents, and patent publications.

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A compound of the formula (I):

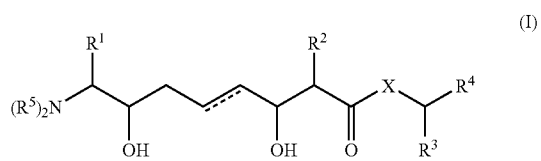

(I)

wherein,
each $R^1$, $R^2$, and $R^3$ are independently alkyl substituted with aryl or heteroaryl, each of which is optionally substituted with 1-5 substituents selected from $OR^6$, CN, $NO_2$, $NHR^7$, $N(R^7)_2$, halo, $CONHR^7$, $CON(R^7)_2$, $CO_2R^8$, or $C_1$ alkyl;
X is O, or S;
$R^4$ is H, $CON(R^7)_2$, $CONHR^7$, $CH_2OH$, $CH(OH)$ $CH=CH_2$, or $C(O)NHCHR^{10}CO_2H$;
each $R^5$ is independently H, alkyl, alkenyl, aryl, heteroaryl, acyl, $P^1$, or $C(O)CHR^{10}NH_2$;
each $R^6$ is independently H, alkyl, or $P^3$;
each $R^7$ is independently H, alkyl, acyl, or $P^2$;
each $R^8$ is independently H, alkyl, aralkyl, or heteroaralkyl;
each $R^{10}$ is independently an amino acid side chain;
each $P^1$ and $P^2$ is independently a nitrogen protecting group; and
each $P^3$ is independently an oxygen protecting group;
or pharmaceutically acceptable salts thereof.

2. The compound of claim 1, wherein:
X is O;
$R^1$ is alkyl substituted with aryl, which is optionally substituted with 1-5 substituents selected from $OR^6$, CN, $NO_2$, $NHR^7$, $N(R^7)_2$, halo, $CONHR^7$, $CON(R^7)_2$, $CO_2R^8$, or $C_{1-6}$ alkyl;
$R^4$ is H, $CON(R^7)_2$, $C(O)NHCHR^{10}CO_2H$, or $CH_2OH$;
each $R^5$ is independently H, alkyl, acyl, $P^1$, or $C(O)CHR^{10}NH_2$;
each $R^6$ is independently H, alkyl, or $P^3$;
each $R^7$ is independently H, alkyl, acyl, or $P^2$;
each $R^8$ is independently H, alkyl, aralkyl, or heteroaralkyl;
each $R^{10}$ is independently an amino acid side chain;
each $P^1$ and $P^2$ is independently a nitrogen protecting group; and
each $P^3$ is independently an oxygen protecting group.

3. The compound of claim 1, wherein:
X is O;
$R^1$ is alkyl substituted with aryl, which is optionally substituted with 1-5 substituents selected from $OR^6$, CN, $NO_2$, halo, or $C_{1-6}$ alkyl;
$R^4$ is H, $CONHR^7$, or $CH_2OH$;
each $R^5$ is independently H or alkyl;
each $R^6$ is independently H or alkyl;
$R^7$ is H, alkyl, or $P^2$; and
$P^2$ is a nitrogen protecting group.

4. The compound of claim 1, wherein:
X is O;
$R^1$ is alkyl substituted with aryl, which is optionally substituted with 1-5 substituents selected from OH or $C_{1-6}$ alkyl; and
$R_4$ is H, $CONH_2$, or $CH_2OH$.

5. The compound of claim 1, wherein:
X is O;
$R^1$ is $C_1$ alkyl substituted with phenyl, which is substituted at the 2- and 6-positions with Me and is substituted at the 4-position with OH; and
$R^4$ is H, $CONH_2$, or $CH_2OH$.

6. The compound of claim 1 having the formula (II):

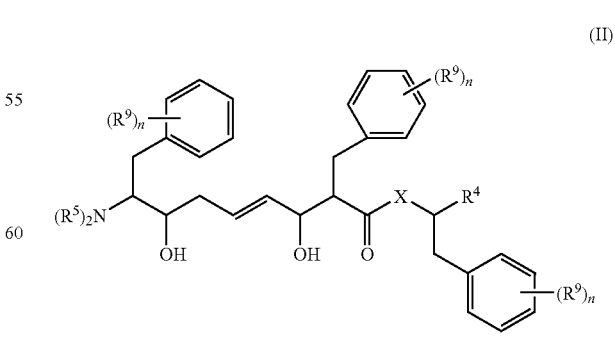

(II)

wherein,
X is O;

$R^4$ is H, $CON(R^7)_2$, $CONHR^7$, $CH_2OH$, or $C(O)NHCHR^{10}CO_2H$;
each $R^5$ is independently H, alkyl, acyl, $P^1$, or $C(O)CHR^{10}NH_2$;
each $R^6$ is independently H, alkyl, or $P^3$;
each $R^7$ is independently H, alkyl, acyl, or $P^2$;
each $R^8$ is independently H, alkyl, aralkyl, or heteroaralkyl;
each $R^9$ is independently $OR^6$, CN, $NO_2$, $NHR^7$, $N(R^7)_2$, halo, $CONHR^7$, $CON(R^7)_2$, $CO_2R^8$, or $C_1$ alkyl;
each $R^{10}$ is independently an amino acid side chain;
each n is independently 0, 1, 2, 3, 4, or 5;
each $P^1$ and $P^2$ is independently a nitrogen protecting group; and
each $P^3$ is independently an oxygen protecting group.

7. The compound of claim 6, wherein:
$R^4$ is H, $CON(R^7)_2$, $CONHR^7$, or $CH_2OH$;
each $R^5$ is independently H, alkyl, or acyl;
each $R^6$ is independently H or alkyl;
each $R^7$ is independently H or alkyl;
each $R^9$ is independently $OR^6$, CN, $NO_2$, halo, or $C_{1-6}$ alkyl; and
each n is independently 0 1, 2, or 3.

8. The compound of claim 6, wherein:
$P^1$ is a BOC or Fmoc;
$P^2$ is a solid support; and
$P^3$ is t-Bu, Bn, Me, or Ac.

9. The compound of claim 6, wherein:
$R^4$ is H, $CON(R^7)_2$, $CONHR^7$, or $CH_2OH$; each $R^5$ is independently H, alkyl, acyl, or $P^1$;
each $R^6$ is H or $P^3$;
each $R^7$ is independently H or $P^2$;
each $R^9$ is independently $OR^6$ or $C_{1-6}$ alkyl;
each n is independently 0, 1, or 2;
$P^1$ is a BOC;
$P^2$ is a solid support; and
$P^3$ is t-Bu.

10. The compound of claim 6, wherein:
$R^4$ is H, $CONH_2$, or $CH_2OH$;
each $R^5$ is independently H, $P^1$, or $C(O)CHR^{10}NH_2$; each $R^6$ is H or alkyl
each $R^9$ is $C_{1-6}$ alkyl or $OR^6$;
each $R^{10}$ is independently an amino acid side chain;
each n is independently 1, 2, or 3; and
$P^1$ is a nitrogen protecting group.

11. The compound of claim 1 that is formula (III):

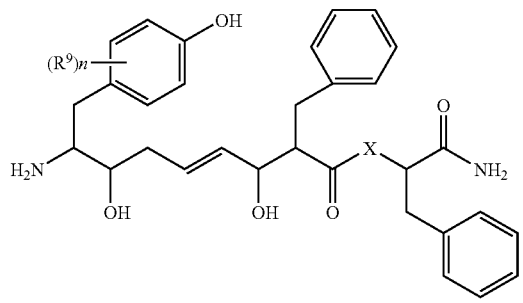
(III)

wherein,
X is O;
$R^9$ is $C_{1-6}$ alkyl; and
n is 2.

12. The compound of claim 1 that is formula (IV):

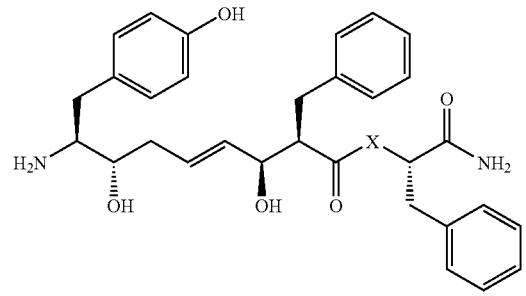
(IV)

wherein X is O.

13. The compound of claim 1 having the formula (V):

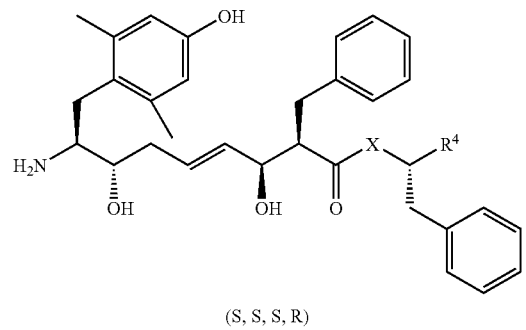
(V)

(S, S, S, R)

wherein
X is O; and
$R^4$ is $CONH_2$, H, or $CH_2OH$.

14. A method of making a compound of the formula (XIV):

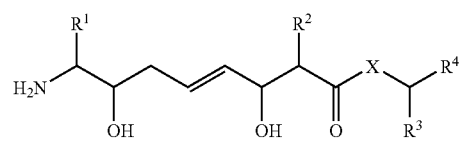
(XIV)

comprising coupling compounds of formulas (XI) and (XIII),

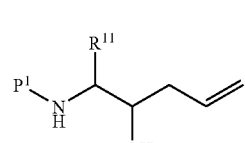
(XI)

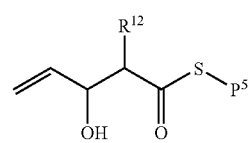
(XIII)

with a ruthenium catalyst;

treating the resulting compound with peroxide and base under conditions sufficient to hydrolyze the thioester;

amidation or esterification of the resulting acid; and treatment of the resulting compound with a deprotecting agent sufficient to remove protecting groups, giving a compound of the formula (XIV);

wherein, each $R^1$, $R^2$, and $R^3$ is independently alkyl substituted with aryl or heteroaryl, each of which is optionally substituted with 1-5 substituents selected from $OR^6$, CN, $NO_2$, $NHR^7$, $N(R^7)_2$, halo, $CONHR^7$, $CON(R^7)_2$, $CO_2R^8$, or $C_{1-6}$ alkyl;

X is O;

$R^4$ is H, $CON(R^7)_2$, $CONHR^7$, $CH_2OH$, or $CH(OH)CH=CH_2$;

each $R^6$ is independently H, alkyl, or $P^3$;

each $R^7$ is independently H, alkyl, acyl, or $P^4$;

each $R^8$ is independently H, alkyl, aralkyl, or heteroaralkyl;

each $R^{11}$ and $R^{12}$ are independently alkyl substituted with aryl or heteroaryl, each of which is optionally substituted with 1-5 substituents selected from $OR^{16}$, CN, $NO_2$, $NHR^{17}$, $N(R^{17})_2$, halo, $CONHR^{17}$, $CON(R^{17})_2$, $CO_2R^{18}$, or $C_{1-6}$ alkyl;

each $R^{16}$ is independently H, alkyl, or $P^3$;

each $R^{17}$ is independently H, alkyl, acyl, or $P^4$;

each $R^{18}$ is independently H, alkyl, aralkyl, or heteroaralkyl; each $P^1$ and $P^4$ is independently a nitrogen protecting group; each $P^3$ is independently an oxygen protecting group; and $P^5$ is a sulfur protecting group.

15. A method of making a compound of formula (XVII):

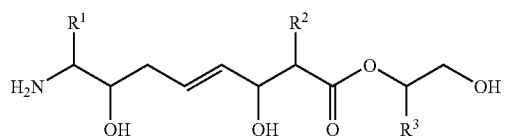

(XVII)

comprising coupling compounds of formulas (XI) and (XIII)

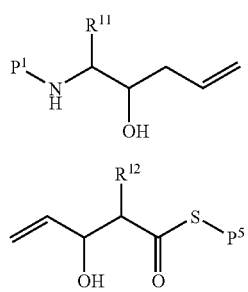

with a ruthenium catalyst;

treating the resulting compound with peroxide and base under conditions sufficient to hydrolyze the thioester; and reacting the free hydroxyls with an oxygen protecting group to give a compound of formula (XVIII)

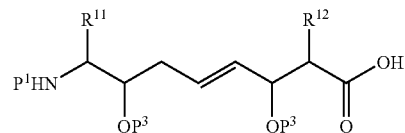

(XVIII)

coupling the compound of formula (XVIII) with an alcohol of formula $R^{13}(CHOH)CHOR^{16}$; and treating the resulting compound with a deprotecting agent sufficient to remove protecting groups to give a compound of formula (XVII);

wherein, each $R^1$, $R^2$, and $R^3$ is independently alkyl substituted with aryl or heteroaryl, each of which is optionally substituted with 1-5 substituents selected from $OR^6$, CN, $NO_2$, $NHR^7$, $N(R^7)_2$, halo, $CONHR^7$, $CON(R^7)_2$, $CO_2R^8$, or $C_{1-6}$ alkyl;

each $R^6$ is independently H, alkyl, or $P^3$;

each $R^7$ is independently H, alkyl, acyl, or $P^4$;

each $R^8$ is independently H, alkyl, aralkyl, or heteroaralkyl;

each $R^{11}$, $R^{12}$, and $R^{13}$ is independently alkyl substituted with aryl or heteroaryl, each of which is optionally substituted with 1-5 substituents selected from $OR^{16}$, CN, $NO_2$, $NHR^{17}$, $N(R^{17})_2$, halo, $CONHR^{17}$, $CON(R^{17})_2$ $CO_2R^{18}$, or $C_{1-6}$ alkyl;

each $R^{16}$ is independently H, alkyl, or $P^3$;

each $R^{17}$ is independently H, alkyl, acyl, or $P^4$;

each $R^{18}$ is independently H, alkyl, aralkyl, or heteroaralkyl;

each $P^1$ and $P^4$ is independently a nitrogen protecting group;

each $P^3$ is independently an oxygen protecting group; and $P^5$ is a sulfur protecting group.

16. A composition comprising a compound of formula (I) in claim 1 and a pharmaceutically acceptable carrier.

17. A compound of formula (XIX):

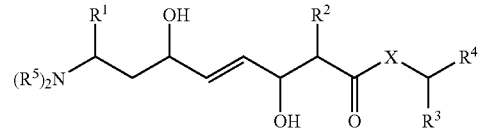

(XIX)

wherein, each $R^1$, $R^2$, and $R^3$ is independently alkyl substituted with aryl or heteroaryl, each of which is optionally substituted with 1-5 substituents selected from $OR^6$, CN, $NO_2$, $NHR^7$, $N(R^7)_2$, halo, $CONHR^7$, $CON(R^7)_2$, $CO_2R^8$, or $C_{1-6}$ alkyl;

X is O, or S;

$R^4$ is H, $CON(R^7)_2$, $CONHR^7$, $CH_2OH$, $CH(OH)CH=CH2$, or $C(O)NHCHR^{10}CO_2H$; each $R^5$ is independently H, alkyl, alkenyl, aryl, heteroaryl, acyl, $P^1$, or $C(O)CHR^{10}NH_2$;

each $R^6$ is independently H, alkyl, or $P^3$;

each $R^7$ is independently H, alkyl, acyl, or $P^2$;

each $R^8$ is independently H, alkyl, aralkyl, or heteroaralkyl;

each $R^{10}$ is independently an amino acid side chain;

each $P^1$ and $P^2$ is independently a nitrogen protecting group;

each $P^3$ is independently an oxygen protecting group; and or pharmaceutically acceptable salts thereof.

18. The compound of claim 17 wherein:

X is O;

$R^1$ is alkyl substituted with aryl, which is optionally substituted with 1-5 substituents selected from $OR^6$, CN, $NO_2$, $NHR^7$, $N(R^7)_2$, halo, $CONHR^7$, $CON(R^7)_2$, $CO_2R^8$, or $C_{1-6}$ alkyl;

$R^4$ is H, $CON(R^7)_2$, $C(O)NHCHR^{10}CO_2H$, or $CH_2OH$; and each $R^5$ is independently H, alkyl, acyl, $P^1$, or $C(O)CHR^{10}NH_2$;

each $R^{10}$ is independently an amino acid side chain.

19. The compound of claim 17, wherein:

X is O;

$R^1$ is alkyl substituted with aryl, which is optionally substituted with 1-5 substituents selected from $OR^6$, CN, $NO_2$, halo, or $C_{1-6}$ alkyl;

$R^4$ is H, $CONHR^7$, or $CH_2OH$;

each $R^5$ is independently H or alkyl;

each $R^6$ is independently H or alkyl; and $R^7$ is H, alkyl, or $P^2$.

20. The compound of claim 17, wherein:

X is O;

$R^1$ is alkyl substituted with aryl, which is optionally substituted with 1-5 substituents selected from OH or $C_{1-6}$ alkyl; and $R^4$ is H, $CONH_2$, or $CH_2OH$.

21. The compound of claim 17, wherein:

X is O;

$R^1$ is $C_1$ alkyl substituted with phenyl, which is substituted at the 2- and 6-positions with Me and is substituted at the 4-position with OH; and $R^4$ is H, $CONH_2$, or $CH_2OH$.

22. The compound of claim 17 having the formula (XX):

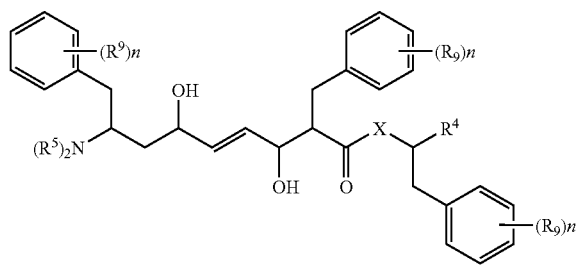

(XX)

wherein,

X is O;

$R^4$ is H, $CON(R^7)_2$, $CONHR^7$, $CH_2OH$, or $C(O)NHCHR^{10}CO_2H$; each $R^5$ is independently H, alkyl, acyl, $P^1$, or $C(O)CHR^{10}NH_2$; each $R^6$ is independently H, alkyl, or $P^3$;

each $R^7$ is independently H, alkyl, acyl; or $P^2$;

each $R^8$ is independently H, alkyl, aralkyl, or heteroaralkyl;

each $R^9$ is independently $OR^6$, CN, $NO_2$, $NHR^7$, $N(R^7)_2$, halo, $CONHR^7$, $CON(R^7)_2$, $CO_2R^8$, or $C_{1-6}$ alkyl;

each $R^{10}$ is independently an amino acid side chain;

each n is independently 0, 1, 2, 3, 4, or 5;

each $P^1$ and $P^2$ is independently a nitrogen protecting group; and each $P^3$ is independently an oxygen protecting group.

23. The compound of claim 22, wherein:

$R^4$ is H, $CON(R^7)_2$, $CONHR^7$, or $CH_2OH$;

each $R^5$ is independently H, alkyl, or acyl; each $R^6$ is independently H or alkyl;

each $R^7$ is independently H or alkyl;

each $R^9$ is independently $OR^6$, CN, $NO_2$, halo, or $C_{1-6}$ alkyl; and each n is independently 0 1, 2, or 3.

24. The compound of claim 22, wherein:

$R^4$ is H, $CON(R^7)_2$, $CONHR^7$, or $CH_2OH$;

each $R^5$ is independently H, alkyl, acyl, or $P^1$; each $R^6$ is independently H or $P^3$;

each $R^7$ is independently H or $P^2$;

each $R^9$ is independently $OR^6$ or $C_{1-6}$ alkyl; each n is independently 0 or 1;

$P^1$ is a BOC;

$P^2$ is a solid support; and $P^3$ is t-Bu.

25. The compound of claim 22, wherein:

$R^4$ is H, $CONH_2$, or $CH_2OH$;

each $R^5$ is independently H, $P^1$, or $C(O)CHR^{10}NH_2$; each $R^6$ is H or alkyl each $R^9$ is $C_{1-6}$ alkyl or $OR^6$;

each $R^{10}$ is independently an amino acid side chain; each n is independently 1, 2, or 3; and $P^1$ is a nitrogen protecting group.

26. The compound of claim 17 having the formula (XXI):

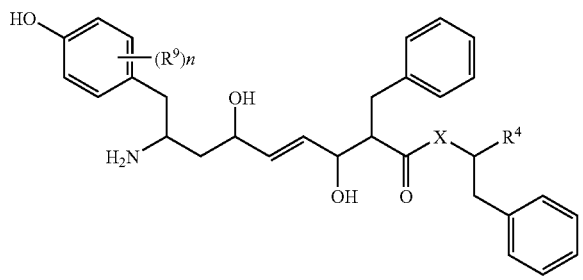

(XXI)

wherein,

X is O;

$R^4$ is H, $CONH_2$, or $CH_2OH$;

$R^9$ is $C_{1-6}$ alkyl; and n is 2.

27. A composition comprising a compound of formula (XIX) in claim 17 or pharmaceutically acceptable salts thereof and a pharmaceutically acceptable carrier.

28. A method of activating a mu opioid receptor (MOR) in a subject comprising administering a compound of formula (I) in claim 1 or a compound of formula (XIX) in claim 17 or pharmaceutically acceptable salts thereof.

29. A method of activating a mu opioid receptor (MOR), in a subject comprising administering a composition comprising a compound of formula (I) in claim 1 or a compound of formula (XIX) in claim 17 or pharmaceutically acceptable salts thereof.

30. A method of treating pain in a subject, comprising administering to the subject a compound of formula (I) in claim 1 or of formula (XIX) in claim 17 or pharmaceutically acceptable salts thereof.

31. A library of compounds of formula (I) in claim 1 or formula (XIX) in claim 17.

* * * * *

UNITED STATES PATENT AND TRADEMARK OFFICE
CERTIFICATE OF CORRECTION

PATENT NO.       : 7,759,514 B2
APPLICATION NO.  : 11/807927
DATED            : July 20, 2010
INVENTOR(S)      : Bryce A. Harrison et al.

It is certified that error appears in the above-identified patent and that said Letters Patent is hereby corrected as shown below:

On the cover page of the patent, before the "Notice" section, please insert the Assignee information as follows:

--Assignee:    President and Fellows of Harvard College, Cambridge, MA (US)--

Signed and Sealed this
Nineteenth Day of July, 2011

David J. Kappos
*Director of the United States Patent and Trademark Office*